US006462178B1

(12) United States Patent
Wong

(10) Patent No.: US 6,462,178 B1
(45) Date of Patent: Oct. 8, 2002

(54) G PROTEIN

(75) Inventor: Yung Hou Wong, Kowloon (HK)

(73) Assignee: Yong Hou Wong, Hong Kong (HK)

( * ) Notice: Subject to any disclaimer, the term of this patent is extended or adjusted under 35 U.S.C. 154(b) by 0 days.

(21) Appl. No.: 09/442,349

(22) Filed: Nov. 17, 1999

(51) Int. Cl.[7] .............................................. C07K 14/00
(52) U.S. Cl. ...................................................... 530/350
(58) Field of Search ........................... 435/195, 5, 325, 435/6, 69.1, 183, 172.1; 536/23.5, 23.1, 23.2; 530/350

(56) References Cited

FOREIGN PATENT DOCUMENTS

WO          WO98/16557         4/1998

OTHER PUBLICATIONS

Venkatakrishnan et al., "Identification of Determinants in the Alpha–Subunit of G–q Required for Phospholipase C Activation", Journal of Biological Chemistry, vol. 271, No. 9, pp. 5066–5072, 1996.*
PCT, International Search Report, PCT/GB00/04347, 5 pages, Apr. 23, 2001; Netherlands.
Conklin et al, Carboxyl–Terminal Mutations of $G_{q\alpha}$ and $G_{s\alpha}$ That Alter the Fideltiy of Receptor Activation, Molecular Pharmacology, 50:885–890, 1996; United States.
Joshi, et al, Chimeric $G\alpha_q$ mutants harboring the last five carboxy–terminal residues of $G\alpha_{i2}$ or $G\alpha_o$ are resistant to pertussis toxin–catalyzed ADP–ribosylation, FEBS Letters 441 (1998) 67–70, 1998.
Tsu et al, Role of Amino– and Carboxyl–Terminal Regions of $G_{\alpha z}$ in the Recognition of $G_i$–Coupled Receptors, Molecular Pharmacology, 52:38–45, 1997, United States.
Amatruda III, et al, $G\alpha 16$, a G protein $\alpha$ subunit specifically expressed in hematopoietic cells, Biochemistry, vol. 88, pp 5587–5591, Jul., 1991, United States.
Parmentier et al, The G Protein–Coupling Profile of Metabotropic Glutamate Receptors, as Determined with Exogenous G Proteins, Is Independent of Their Ligand Recognition Domain, Molecular Pharmacology, 53:778–786, 1998, United States.
Kozasa, et al, Isolation and characterization of the human $G_s\alpha$ gene, Biochemistry, vol. 85, pp 2081–2085, Apr. 1988; United States.
Gagnon et al, Identification of $G_{z\alpha}$ as a Pertussis Toxin–Insensitive G Protein in Human Platelets and Megakaryocytes, Blood, vol. 78, No. 5, pp 1247–1253, Sep. 11, 1991; United States.
Kang et al, Effects of Expression of Mammalian $G\alpha$ and Hybrid Mammalian–Yeast $G\alpha$ Proteins on the Yeast Pheromone Response Signal Transduction Pathway, Molecular and Cellular Biology, pp 2582–2590, Jun. 1990, United States.
Coward et al, Chimeric G Proteins Allow a High–Throughput Signaling Assay of $G_i$–Coupled Receptors, Analytical Biochemistry 270, 242–248, 1999, United States.
Lambright et al, Structural determinants for activation of the $\alpha$–subunit of a heterotrimeric G protein, Nature, vol. 369, pp 621–628, Jun. 1994, United States.

* cited by examiner

*Primary Examiner*—Karen Cochrane Carlson
(74) *Attorney, Agent, or Firm*—Dority & Manning, PA

(57) ABSTRACT

The present invention concerns novel G protein chimeras, nucleotide sequences encoding same, host cells transformed or transfected with same, methods of determining GPCR response to a molecule, and kits for same.

17 Claims, 11 Drawing Sheets

N-Terminus

```
                               αN                    β1
Gz   1-39  ---------MGCRQSSE..E...RSRR.D.H.RSESQRQ.R.I.....
G16  1-48  MARSLTWRCCPWCLTEDEKAAARVDQEINRILLEQKKQDRGELKLLLL

30z16      ---------MGCRQSSEEKEAARRSRRIDRHLRSESQRQRREI.....
```

C-Terminus

```
                          α4
Gz  288-316  ..EYK.QNTYE...V-YIQRQFEDLNRNKE----------
G16 295-334  FPSFQGPKQDAEAAKRFILDMYTRMYTGCVDGPEGSKKGA

16z25        ████████████████████████████████████████
16z44        ████████████████████████████████████NRNK
16z66        ███████KGQNTYEEAAV-YIQRQFEDLNRNKE--------

β6              α5
Gz  317-355  -TKEIY..F......S..QF..DA.T.VIIQNN.KY.G.C
G16 335-374  RSRRLFSHYTCATDTQNIRKVFKDVRDSVLARYLDEINLL

16z25        ████████████████████SNIQFVFDAVTDVIIQNNLKYIGLC
16z44        ETKEIYSHFTCATDTSNIQFVFDAVTDVIIQNNLKYIGLC
16z66        -TKEIYSHFTCATDTSNIQFVFDAVTDVIIQNNLKYIGLC
```

Figure 3

SEQUENCE LISTING

<160> NUMBER OF SEQ ID NOS: 116

<210> SEQ ID NO 1
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 1

Met Ala Arg Ser Leu Thr Trp Arg Cys Cys Pro Trp Cys Leu Thr Glu
 1               5                  10                  15

Asp Glu Lys Ala Ala Ala Arg Val Asp Gln Glu Ile Asn Arg Ile Leu
             20                  25                  30

Leu Glu Gln Lys Lys Gln Asp Arg Gly Glu Leu Lys Leu Leu Leu
         35                  40                  45

Gly Pro Gly Glu Ser Gly Lys Ser Thr Phe Ile Lys Gln Met Arg Ile
 50                  55                  60

Ile His Gly Ala Gly Tyr Ser Glu Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
    210                 215                 220

```
Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Ser Asn Ile
            340                 345                 350

Gln Phe Val Phe Asp Ala Val Thr Asp Val Ile Ile Gln Asn Asn Leu
        355                 360                 365

Lys Tyr Ile Gly Leu Cys
    370

<210> SEQ ID NO 2
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 2

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205
```

```
Val Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Asn Arg Asn Lys Glu Thr
                325                 330                 335

Lys Glu Ile Tyr Ser His Phe Thr Cys Ala Thr Asp Thr Ser Asn Ile
            340                 345                 350

Gln Phe Val Phe Asp Ala Val Thr Asp Val Ile Ile Gln Asn Asn Leu
        355                 360                 365

Lys Tyr Ile Gly Leu Cys
    370

<210> SEQ ID NO 3
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 3

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
```

-continued

Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Glu Asn Ile
            340                 345                 350

Arg Arg Val Phe Asn Asp Cys Arg Asp Ile Ile Gln Arg Met His Leu
        355                 360                 365

Arg Gln Tyr Glu Leu Leu
    370

<210> SEQ ID NO 4
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 4

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

-continued

```
Val Tyr Tyr Leu Ser His Leu Glu Arg Ile Thr Glu Glu Gly Tyr Val
            165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
            210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
            245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
            290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Ala Ser Gly Asp Gly Arg
            325                 330                 335

His Tyr Cys Tyr Pro His Phe Thr Cys Ala Val Asp Thr Glu Asn Ile
            340                 345                 350

Arg Arg Val Phe Asn Asp Cys Arg Asp Ile Ile Gln Arg Met His Leu
            355                 360                 365

Arg Gln Tyr Glu Leu Leu
            370

<210> SEQ ID NO 5
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 5

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
            85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
            115                 120                 125

Lys Arg Tyr Ala Ala Ala Met Gln Trp Leu Trp Arg Asp Ala Gly Ile
    130                 135                 140
```

```
Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Gly Tyr Val
            165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
            210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
            245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
            290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
            325                 330                 335

Arg Arg Leu Phe Ser His Tyr Thr Cys Ala Thr Asp Thr Cys Asn Ile
            340                 345                 350

Gln Phe Val Phe Asp Ala Val Thr Asp Val Ile Ile Gln Asn Asn Leu
            355                 360                 365

Lys Tyr Ile Gly Leu Cys
    370

<210> SEQ ID NO 6
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 6

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
```

-continued

```
                115                 120                 125

Lys Arg Tyr Ala Ala Met Gln Trp Leu Trp Arg Asp Ala Gly Ile
        130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
            245                 250                 255

Leu Phe Gly Thr Ile Leu Glu Leu Pro Trp Phe Lys Ser Thr Ser Val
        260                 265                 270

Ile Leu Phe Leu Asn Lys Thr Asp Ile Leu Glu Glu Lys Ile Pro Thr
    275                 280                 285

Ser His Leu Ala Thr Tyr Phe Pro Ser Phe Gln Gly Pro Lys Gln Asp
290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
            325                 330                 335

Arg Arg Leu Phe Ser His Tyr Thr Cys Ala Thr Asp Thr Lys Asn Ile
        340                 345                 350

Gln Phe Val Phe Asp Ala Val Thr Asp Val Ile Ile Gln Asn Asn Leu
            355                 360                 365

Lys Tyr Ile Gly Leu Cys
        370

<210> SEQ ID NO 7
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 7

Met Ala Arg Ser Leu Thr Trp Arg Cys Cys Pro Trp Cys Leu Thr Glu
1               5                   10                  15

Asp Glu Lys Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95
```

```
Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
            115                 120                 125

Lys Arg Tyr Ala Ala Met Gln Trp Leu Trp Arg Asp Ala Gly Ile
        130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
            210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Asn Asn Ile
            340                 345                 350

Gln Phe Val Phe Asp Ala Val Thr Asp Val Ile Ile Gln Asn Asn Leu
        355                 360                 365

Lys Tyr Ile Gly Leu Cys
        370

<210> SEQ ID NO 8
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 8

Met Ala Arg Ser Leu Thr Trp Arg Cys Cys Pro Trp Cys Leu Thr Glu
1               5                   10                  15

Asp Glu Lys Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80
```

```
Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
            115                 120                 125

Lys Arg Tyr Ala Ala Met Gln Trp Leu Trp Arg Asp Ala Gly Ile
        130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
        210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Ser Asn Ile
            340                 345                 350

Gln Phe Val Phe Glu Ala Val Thr Asp Val Ile Ile Gln Asn Asn Leu
        355                 360                 365

Lys Tyr Ile Gly Leu Cys
    370

<210> SEQ ID NO 9
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 9

Met Ala Arg Ser Leu Thr Trp Arg Cys Cys Pro Trp Cys Leu Thr Glu
  1               5                  10                  15

Asp Glu Lys Ala Ala Ala Arg Val Asp Gln Glu Ile Asn Arg Ile Leu
             20                  25                  30

Leu Glu Gln Lys Lys Gln Asp Arg Gly Glu Leu Lys Leu Leu Leu
         35                  40                  45

Gly Pro Gly Glu Ser Gly Lys Ser Thr Phe Ile Lys Gln Met Arg Ile
```

```
            50                  55                  60
Ile His Gly Ala Gly Tyr Ser Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
                100                 105                 110

Ala Ser Leu Val Met Ser Gln Asp Pro Tyr Lys Val Thr Thr Phe Glu
                115                 120                 125

Lys Arg Tyr Ala Ala Met Gln Trp Leu Trp Arg Asp Ala Gly Ile
130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
                180                 185                 190

Asn Glu Tyr Cys Phe Ser Val Gln Lys Thr Asn Leu Arg Ile Val Asp
                195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
                260                 265                 270

Ile Leu Phe Leu Asn Lys Thr Asp Ile Leu Glu Glu Lys Ile Pro Thr
                275                 280                 285

Ser His Leu Ala Thr Tyr Phe Pro Ser Phe Gln Gly Pro Lys Gln Asp
                290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Ser Asn Ile
                340                 345                 350

Gln Phe Val Phe Asn Ala Val Thr Asp Val Ile Ile Gln Asn Asn Leu
                355                 360                 365

Lys Tyr Ile Gly Leu Cys
                370

<210> SEQ ID NO 10
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 10

Met Ala Arg Ser Leu Thr Trp Arg Cys Cys Pro Trp Cys Leu Thr Glu
 1               5                  10                  15

Asp Glu Lys Ala Ala Ala Arg Val Asp Gln Glu Ile Asn Arg Ile Leu
                20                  25                  30
```

```
Leu Glu Gln Lys Lys Gln Asp Arg Gly Glu Leu Lys Leu Leu Leu Leu
                35                  40                  45

Gly Pro Gly Glu Ser Gly Lys Ser Thr Phe Ile Lys Gln Met Arg Ile
 50                  55                  60

Ile His Gly Ala Gly Tyr Ser Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
                100                 105                 110

Ala Ser Leu Val Met Ser Gln Asp Pro Tyr Lys Val Thr Thr Phe Glu
            115                 120                 125

Lys Arg Tyr Ala Ala Met Gln Trp Leu Trp Arg Asp Ala Gly Ile
130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
                180                 185                 190

Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
            210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
                260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
            290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Ser Asn Ile
                340                 345                 350

Gln Phe Val Phe Gln Ala Val Thr Asp Val Ile Ile Gln Asn Asn Leu
            355                 360                 365

Lys Tyr Ile Gly Leu Cys
    370

<210> SEQ ID NO 11
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 11

Met Ala Arg Ser Leu Thr Trp Arg Cys Cys Pro Trp Cys Leu Thr Glu
 1               5                  10                  15
```

-continued

```
Asp Glu Lys Ala Ala Arg Val Asp Gln Glu Ile Asn Arg Ile Leu
         20                  25                  30
Leu Glu Gln Lys Lys Gln Asp Arg Gly Glu Leu Lys Leu Leu Leu
         35                  40                  45
Gly Pro Gly Glu Ser Gly Lys Ser Thr Phe Ile Lys Gln Met Arg Ile
 50                  55                  60
Ile His Gly Ala Gly Tyr Ser Glu Glu Arg Lys Gly Phe Arg Pro
 65                  70                  75                  80
Leu Val Tyr Gln Asn Ile Phe Val Ser Met Arg Ala Met Ile Glu Ala
                     85                  90                  95
Met Glu Arg Leu Gln Ile Pro Phe Ser Arg Pro Glu Ser Lys His His
             100                 105                 110
Ala Ser Leu Val Met Ser Gln Asp Pro Tyr Lys Val Thr Thr Phe Glu
             115                 120                 125
Lys Arg Tyr Ala Ala Ala Met Gln Trp Leu Trp Arg Asp Ala Gly Ile
             130                 135                 140
Arg Ala Cys Tyr Glu Arg Arg Arg Glu Phe His Leu Leu Asp Ser Ala
145                 150                 155                 160
Val Tyr Tyr Leu Ser His Leu Glu Arg Ile Thr Glu Glu Gly Tyr Val
                 165                 170                 175
Pro Thr Ala Gln Asp Val Leu Arg Ser Arg Met Pro Thr Thr Gly Ile
             180                 185                 190
Asn Glu Tyr Cys Phe Ser Val Gln Lys Thr Asn Leu Arg Ile Val Asp
             195                 200                 205
Val Gly Gly Gln Lys Ser Glu Arg Lys Lys Trp Ile His Cys Phe Glu
         210                 215                 220
Asn Val Ile Ala Leu Ile Tyr Leu Ala Ser Leu Ser Glu Tyr Asp Gln
225                 230                 235                 240
Cys Leu Glu Glu Asn Asn Gln Glu Asn Arg Met Lys Glu Ser Leu Ala
                 245                 250                 255
Leu Phe Gly Thr Ile Leu Glu Leu Pro Trp Phe Lys Ser Thr Ser Val
             260                 265                 270
Ile Leu Phe Leu Asn Lys Thr Asp Ile Leu Glu Glu Lys Ile Pro Thr
             275                 280                 285
Ser His Leu Ala Thr Tyr Phe Pro Ser Phe Gln Gly Pro Lys Gln Asp
         290                 295                 300
Ala Glu Ala Ala Lys Arg Phe Ile Leu Asp Met Tyr Thr Arg Met Tyr
305                 310                 315                 320
Thr Gly Cys Val Asp Gly Pro Glu Gly Ser Lys Lys Gly Ala Arg Ser
                 325                 330                 335
Arg Arg Leu Phe Ser His Tyr Thr Cys Ala Thr Asp Thr Cys Asn Ile
             340                 345                 350
Gln Phe Val Phe Glu Ala Val Thr Asp Val Ile Ile Gln Asn Asn Leu
             355                 360                 365
Lys Tyr Ile Gly Leu Cys
             370
```

<210> SEQ ID NO 12
<211> LENGTH: 374
<212> TYPE: PRT
<213> ORGANISM: Artificial Sequence
<220> FEATURE:
<223> OTHER INFORMATION: Description of Artificial Sequence: G protein chimera

```
<400> SEQUENCE: 12

Met Ala Arg Ser Leu Thr Trp Arg Cys Cys Pro Trp Cys Leu Thr Glu
  1               5                  10                  15

Asp Glu Lys Ala Ala Arg Val Asp Gln Glu Ile Asn Arg Ile Leu
             20                  25                  30

Leu Glu Gln Lys Lys Gln Asp Arg Gly Glu Leu Lys Leu Leu Leu
         35                  40                  45

Gly Pro Gly Glu Ser Gly Lys Ser Thr Phe Ile Lys Gln Met Arg Ile
 50                  55                  60

Ile His Gly Ala Gly Tyr Ser Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
             100                 105                 110

Ala Ser Leu Val Met Ser Gln Asp Pro Tyr Lys Val Thr Thr Phe Glu
         115                 120                 125

Lys Arg Tyr Ala Ala Met Gln Trp Leu Trp Arg Asp Ala Gly Ile
130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
                 165                 170                 175

Pro Thr Ala Gln Asp Val Leu Arg Ser Arg Met Pro Thr Thr Gly Ile
             180                 185                 190

Asn Glu Tyr Cys Phe Ser Val Gln Lys Thr Asn Leu Arg Ile Val Asp
             195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                 245                 250                 255

Leu Phe Gly Thr Ile Leu Glu Leu Pro Trp Phe Lys Ser Thr Ser Val
             260                 265                 270

Ile Leu Phe Leu Asn Lys Thr Asp Ile Leu Glu Glu Lys Ile Pro Thr
             275                 280                 285

Ser His Leu Ala Thr Tyr Phe Pro Ser Phe Gln Gly Pro Lys Gln Asp
290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                 325                 330                 335

Arg Arg Leu Phe Ser His Tyr Thr Cys Ala Thr Asp Thr Cys Asn Ile
             340                 345                 350

Gln Phe Val Phe Asn Ala Val Thr Asp Val Ile Ile Gln Asn Asn Leu
             355                 360                 365

Lys Tyr Ile Gly Leu Cys
    370

<210> SEQ ID NO 13
<211> LENGTH: 374
<212> TYPE: PRT
<213> ORGANISM: Artificial Sequence
```

```
<220> FEATURE:
<223> OTHER INFORMATION: Description of Artificial Sequence: G protein
      chimera

<400> SEQUENCE: 13

Met Ala Arg Ser Leu Thr Trp Arg Cys Cys Pro Trp Cys Leu Thr Glu
  1               5                  10                  15

Asp Glu Lys Ala Ala Arg Val Asp Gln Glu Ile Asn Arg Ile Leu
             20                  25                  30

Leu Glu Gln Lys Lys Gln Asp Arg Gly Glu Leu Lys Leu Leu Leu
         35                  40                  45

Gly Pro Gly Glu Ser Gly Lys Ser Thr Phe Ile Lys Gln Met Arg Ile
 50                  55                  60

Ile His Gly Ala Gly Tyr Ser Glu Glu Arg Lys Gly Phe Arg Pro
 65                  70                  75                  80

Leu Val Tyr Gln Asn Ile Phe Val Ser Met Arg Ala Met Ile Glu Ala
                     85                  90                  95

Met Glu Arg Leu Gln Ile Pro Phe Ser Arg Pro Glu Ser Lys His His
                100                 105                 110

Ala Ser Leu Val Met Ser Gln Asp Pro Tyr Lys Val Thr Thr Phe Glu
                115                 120                 125

Lys Arg Tyr Ala Ala Met Gln Trp Leu Trp Arg Asp Ala Gly Ile
130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
                180                 185                 190

Asn Glu Tyr Cys Phe Ser Val Gln Lys Thr Asn Leu Arg Ile Val Asp
                195                 200                 205

Val Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
                260                 265                 270

Ile Leu Phe Leu Asn Lys Thr Asp Ile Leu Glu Glu Lys Ile Pro Thr
                275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Cys Asn Ile
                340                 345                 350

Gln Phe Val Phe Gln Ala Val Thr Asp Val Ile Ile Gln Asn Asn Leu
                355                 360                 365

Lys Tyr Ile Gly Leu Cys
    370
```

-continued

```
<210> SEQ ID NO 14
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 14
```

Met Ala Arg Ser Leu Thr Trp Arg Cys Cys Pro Trp Cys Leu Thr Glu
 1               5                  10                  15

Asp Glu Lys Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Lys Asn Ile
            340                 345                 350

Gln Phe Val Phe Glu Ala Val Thr Asp Val Ile Ile Gln Asn Asn Leu
        355                 360                 365

```
Lys Tyr Ile Gly Leu Cys
    370

<210> SEQ ID NO 15
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 15

Met Ala Arg Ser Leu Thr Trp Arg Cys Cys Pro Trp Cys Leu Thr Glu
  1               5                  10                  15

Asp Glu Lys Ala Ala Arg Val Asp Gln Glu Ile Asn Arg Ile Leu
             20                  25                  30

Leu Glu Gln Lys Lys Gln Asp Arg Gly Glu Leu Lys Leu Leu Leu
         35                  40                  45

Gly Pro Gly Glu Ser Gly Lys Ser Thr Phe Ile Lys Gln Met Arg Ile
 50                  55                  60

Ile His Gly Ala Gly Tyr Ser Glu Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Lys Asn Ile
            340                 345                 350
```

```
Gln Phe Val Phe Asn Ala Val Thr Asp Val Ile Ile Gln Asn Asn Leu
            355                 360                 365
Lys Tyr Ile Gly Leu Cys
        370
```

<210> SEQ ID NO 16
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 16

```
Met Ala Arg Ser Leu Thr Trp Arg Cys Cys Pro Trp Cys Leu Thr Glu
  1               5                  10                  15
Asp Glu Lys Ala Ala Arg Val Asp Gln Glu Ile Asn Arg Ile Leu
             20                  25                  30
Leu Glu Gln Lys Lys Gln Asp Arg Gly Glu Leu Lys Leu Leu Leu
         35                  40                  45
Gly Pro Gly Glu Ser Gly Lys Ser Thr Phe Ile Lys Gln Met Arg Ile
     50                  55                  60
Ile His Gly Ala Gly Tyr Ser Glu Glu Gly Arg Lys Gly Phe Arg Pro
 65                  70                  75                  80
Leu Val Tyr Gln Asn Ile Phe Val Ser Met Arg Ala Met Ile Glu Ala
                 85                  90                  95
Met Glu Arg Leu Gln Ile Pro Phe Ser Arg Pro Glu Ser Lys His His
            100                 105                 110
Ala Ser Leu Val Met Ser Gln Asp Pro Tyr Lys Val Thr Thr Phe Glu
        115                 120                 125
Lys Arg Tyr Ala Ala Ala Met Gln Trp Leu Trp Arg Asp Ala Gly Ile
    130                 135                 140
Arg Ala Cys Tyr Glu Arg Arg Arg Glu Phe His Leu Leu Asp Ser Ala
145                 150                 155                 160
Val Tyr Tyr Leu Ser His Leu Glu Arg Ile Thr Glu Glu Gly Tyr Val
                165                 170                 175
Pro Thr Ala Gln Asp Val Leu Arg Ser Arg Met Pro Thr Thr Gly Ile
            180                 185                 190
Asn Glu Tyr Cys Phe Ser Val Gln Lys Thr Asn Leu Arg Ile Val Asp
        195                 200                 205
Val Gly Gly Gln Lys Ser Glu Arg Lys Lys Trp Ile His Cys Phe Glu
    210                 215                 220
Asn Val Ile Ala Leu Ile Tyr Leu Ala Ser Leu Ser Glu Tyr Asp Gln
225                 230                 235                 240
Cys Leu Glu Glu Asn Asn Gln Glu Asn Arg Met Lys Glu Ser Leu Ala
                245                 250                 255
Leu Phe Gly Thr Ile Leu Glu Leu Pro Trp Phe Lys Ser Thr Ser Val
            260                 265                 270
Ile Leu Phe Leu Asn Lys Thr Asp Ile Leu Glu Glu Lys Ile Pro Thr
        275                 280                 285
Ser His Leu Ala Thr Tyr Phe Pro Ser Phe Gln Gly Pro Lys Gln Asp
    290                 295                 300
Ala Glu Ala Ala Lys Arg Phe Ile Leu Asp Met Tyr Thr Arg Met Tyr
305                 310                 315                 320
Thr Gly Cys Val Asp Gly Pro Glu Gly Ser Lys Lys Gly Ala Arg Ser
```

```
                     325                 330                 335
Arg Arg Leu Phe Ser His Tyr Thr Cys Ala Thr Asp Thr Lys Asn Ile
                340                 345                 350

Gln Phe Val Phe Gln Ala Val Thr Asp Val Ile Ile Gln Asn Asn Leu
            355                 360                 365

Lys Tyr Ile Gly Leu Cys
        370

<210> SEQ ID NO 17
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 17

Met Ala Arg Ser Leu Thr Trp Arg Cys Cys Pro Trp Cys Leu Thr Glu
  1               5                  10                  15

Asp Glu Lys Ala Ala Ala Arg Val Asp Gln Glu Ile Asn Arg Ile Leu
             20                  25                  30

Leu Glu Gln Lys Lys Gln Asp Arg Gly Glu Leu Lys Leu Leu Leu Leu
         35                  40                  45

Gly Pro Gly Glu Ser Gly Lys Ser Thr Phe Ile Lys Gln Met Arg Ile
     50                  55                  60

Ile His Gly Ala Gly Tyr Ser Glu Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300
```

```
Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
            325                 330                 335

Arg Arg Leu Phe Ser His Tyr Thr Cys Ala Thr Asp Thr Asn Asn Ile
            340                 345                 350

Gln Phe Val Phe Glu Ala Val Thr Asp Val Ile Ile Gln Asn Asn Leu
            355                 360                 365

Lys Tyr Ile Gly Leu Cys
            370

<210> SEQ ID NO 18
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 18

Met Ala Arg Ser Leu Thr Trp Arg Cys Cys Pro Trp Cys Leu Thr Glu
1               5                   10                  15

Asp Glu Lys Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
            35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65              70                  75                  80

Leu Val Tyr Gln Asn Ile Phe Val Ser Met Arg Ala Met Ile Glu Ala
            85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
            115                 120                 125

Lys Arg Tyr Ala Ala Ala Met Gln Trp Leu Trp Arg Asp Ala Gly Ile
130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
            245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
            275                 280                 285
```

```
Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Asn Asn Ile
                340                 345                 350

Gln Phe Val Phe Asn Ala Val Thr Asp Val Ile Ile Gln Asn Asn Leu
                355                 360                 365

Lys Tyr Ile Gly Leu Cys
    370

<210> SEQ ID NO 19
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 19

Met Ala Arg Ser Leu Thr Trp Arg Cys Cys Pro Trp Cys Leu Thr Glu
  1               5                  10                  15

Asp Glu Lys Ala Ala Ala Arg Val Asp Gln Glu Ile Asn Arg Ile Leu
                 20                  25                  30

Leu Glu Gln Lys Lys Gln Asp Arg Gly Glu Leu Lys Leu Leu Leu Leu
             35                  40                  45

Gly Pro Gly Glu Ser Gly Lys Ser Thr Phe Ile Lys Gln Met Arg Ile
 50                  55                  60

Ile His Gly Ala Gly Tyr Ser Glu Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
```

-continued

```
                260                 265                 270
Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Asn Asn Ile
            340                 345                 350

Gln Phe Val Phe Gln Ala Val Thr Asp Val Ile Ile Gln Asn Asn Leu
            355                 360                 365

Lys Tyr Ile Gly Leu Cys
    370

<210> SEQ ID NO 20
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 20

Met Ala Arg Ser Leu Thr Trp Arg Cys Cys Pro Trp Cys Leu Thr Glu
  1               5                  10                  15

Asp Glu Lys Ala Ala Ala Arg Val Asp Gln Glu Ile Asn Arg Ile Leu
                 20                  25                  30

Leu Glu Gln Lys Lys Gln Asp Arg Gly Glu Leu Lys Leu Leu Leu Leu
             35                  40                  45

Gly Pro Gly Glu Ser Gly Lys Ser Thr Phe Ile Lys Gln Met Arg Ile
         50                  55                  60

Ile His Gly Ala Gly Tyr Ser Glu Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
                100                 105                 110

Ala Ser Leu Val Met Ser Gln Asp Pro Tyr Lys Val Thr Thr Phe Glu
            115                 120                 125

Lys Arg Tyr Ala Ala Ala Met Gln Trp Leu Trp Arg Asp Ala Gly Ile
        130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
225                 230                 235                 240
```

```
Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Asn Arg Asn Lys Glu Thr
                325                 330                 335

Lys Glu Ile Tyr Ser His Phe Thr Cys Ala Thr Asp Thr Cys Asn Ile
            340                 345                 350

Gln Phe Val Phe Asp Ala Val Thr Asp Val Ile Ile Gln Asn Asn Leu
        355                 360                 365

Lys Tyr Ile Gly Leu Cys
370

<210> SEQ ID NO 21
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 21

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
    210                 215                 220
```

```
Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Asn Arg Asn Lys Glu Thr
                325                 330                 335

Lys Glu Ile Tyr Ser His Phe Thr Cys Ala Thr Asp Thr Lys Asn Ile
                340                 345                 350

Gln Phe Val Phe Asp Ala Val Thr Asp Val Ile Ile Gln Asn Asn Leu
            355                 360                 365

Lys Tyr Ile Gly Leu Cys
        370
```

<210> SEQ ID NO 22
<211> LENGTH: 374
<212> TYPE: PRT
<213> ORGANISM: Artificial Sequence
<220> FEATURE:
<223> OTHER INFORMATION: Description of Artificial Sequence: G protein chimera

<400> SEQUENCE: 22

```
Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
```

-continued

```
                195                 200                     205
Val Gly Gly Gln Lys Ser Glu Arg Lys Lys Trp Ile His Cys Phe Glu
210                 215                     220

Asn Val Ile Ala Leu Ile Tyr Leu Ala Ser Leu Ser Glu Tyr Asp Gln
225                 230                     235                 240

Cys Leu Glu Glu Asn Asn Gln Glu Asn Arg Met Lys Glu Ser Leu Ala
                245                     250                 255

Leu Phe Gly Thr Ile Leu Glu Leu Pro Trp Phe Lys Ser Thr Ser Val
                260                     265                 270

Ile Leu Phe Leu Asn Lys Thr Asp Ile Leu Glu Glu Lys Ile Pro Thr
                275                     280                 285

Ser His Leu Ala Thr Tyr Phe Pro Ser Phe Gln Gly Pro Lys Gln Asp
290                 295                     300

Ala Glu Ala Ala Lys Arg Phe Ile Leu Asp Met Tyr Thr Arg Met Tyr
305                 310                     315                 320

Thr Gly Cys Val Asp Gly Pro Glu Gly Ser Asn Arg Asn Lys Glu Thr
                325                     330                 335

Lys Glu Ile Tyr Ser His Phe Thr Cys Ala Thr Asp Thr Asn Asn Ile
                340                     345                 350

Gln Phe Val Phe Asp Ala Val Thr Asp Val Ile Ile Gln Asn Asn Leu
                355                     360                 365

Lys Tyr Ile Gly Leu Cys
370

<210> SEQ ID NO 23
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 23

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
                20                  25                  30

Leu Glu Gln Lys Lys Gln Asp Arg Gly Glu Leu Lys Leu Leu Leu Leu
            35                  40                  45

Gly Pro Gly Glu Ser Gly Lys Ser Thr Phe Ile Lys Gln Met Arg Ile
        50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
                100                 105                 110

Ala Ser Leu Val Met Ser Gln Asp Pro Tyr Lys Val Thr Thr Phe Glu
            115                 120                 125

Lys Arg Tyr Ala Ala Ala Met Gln Trp Leu Trp Arg Asp Ala Gly Ile
130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175
```

-continued

```
Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
            290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Asn Arg Asn Lys Glu Thr
                325                 330                 335

Lys Glu Ile Tyr Ser His Phe Thr Cys Ala Thr Asp Thr Ser Asn Ile
            340                 345                 350

Gln Phe Val Phe Glu Ala Val Thr Asp Val Ile Ile Gln Asn Asn Leu
            355                 360                 365

Lys Tyr Ile Gly Leu Cys
370

<210> SEQ ID NO 24
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 24

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160
```

```
Val Tyr Tyr Leu Ser His Leu Glu Arg Ile Thr Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
            210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
                260                 265                 270

Ile Leu Phe Leu Asn Lys Thr Asp Ile Leu Glu Lys Ile Pro Thr
                275                 280                 285

Ser His Leu Ala Thr Tyr Phe Pro Ser Phe Gln Gly Pro Lys Gln Asp
            290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Asn Arg Asn Lys Glu Thr
                325                 330                 335

Lys Glu Ile Tyr Ser His Phe Thr Cys Ala Thr Asp Thr Ser Asn Ile
                340                 345                 350

Gln Phe Val Phe Asn Ala Val Thr Asp Val Ile Ile Gln Asn Asn Leu
            355                 360                 365

Lys Tyr Ile Gly Leu Cys
    370

<210> SEQ ID NO 25
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 25

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
```

-continued

```
            130                 135                 140
Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
                180                 185                 190

Asn Glu Tyr Cys Phe Ser Val Gln Lys Thr Asn Leu Arg Ile Val Asp
                195                 200                 205

Val Gly Gly Gln Lys Ser Glu Arg Lys Lys Trp Ile His Cys Phe Glu
                210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
                260                 265                 270

Ile Leu Phe Leu Asn Lys Thr Asp Ile Leu Glu Glu Lys Ile Pro Thr
                275                 280                 285

Ser His Leu Ala Thr Tyr Phe Pro Ser Phe Gln Gly Pro Lys Gln Asp
                290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Asn Arg Asn Lys Glu Thr
                325                 330                 335

Lys Glu Ile Tyr Ser His Phe Thr Cys Ala Thr Asp Thr Ser Asn Ile
                340                 345                 350

Gln Phe Val Phe Gln Ala Val Thr Asp Val Ile Ile Gln Asn Asn Leu
                355                 360                 365

Lys Tyr Ile Gly Leu Cys
                370
```

<210> SEQ ID NO 26
<211> LENGTH: 374
<212> TYPE: PRT
<213> ORGANISM: Artificial Sequence
<220> FEATURE:
<223> OTHER INFORMATION: Description of Artificial Sequence: G protein chimera

<400> SEQUENCE: 26

```
Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
                20                  25                  30

Leu Glu Gln Lys Lys Gln Asp Arg Gly Glu Leu Lys Leu Leu Leu Leu
            35                  40                  45

Gly Pro Gly Glu Ser Gly Lys Ser Thr Phe Ile Lys Gln Met Arg Ile
        50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
                100                 105                 110
```

```
Ala Ser Leu Val Met Ser Gln Asp Pro Tyr Lys Val Thr Thr Phe Glu
        115                 120                 125

Lys Arg Tyr Ala Ala Met Gln Trp Leu Trp Arg Asp Ala Gly Ile
130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
                195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
275                 280                 285

Ser His Leu Ala Thr Tyr Phe Pro Ser Phe Gln Gly Pro Lys Gln Asp
290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Asn Arg Asn Lys Glu Thr
                325                 330                 335

Lys Glu Ile Tyr Ser His Phe Thr Cys Ala Thr Asp Thr Cys Asn Ile
                340                 345                 350

Gln Phe Val Phe Glu Ala Val Thr Asp Val Ile Ile Gln Asn Asn Leu
            355                 360                 365

Lys Tyr Ile Gly Leu Cys
        370

<210> SEQ ID NO 27
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 27

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95
```

```
Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
            115                 120                 125

Lys Arg Tyr Ala Ala Ala Met Gln Trp Leu Trp Arg Asp Ala Gly Ile
            130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
            210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
            245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
            290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Asn Arg Asn Lys Glu Thr
            325                 330                 335

Lys Glu Ile Tyr Ser His Phe Thr Cys Ala Thr Asp Thr Cys Asn Ile
            340                 345                 350

Gln Phe Val Phe Asn Ala Val Thr Asp Val Ile Ile Gln Asn Asn Leu
            355                 360                 365

Lys Tyr Ile Gly Leu Cys
    370

<210> SEQ ID NO 28
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 28

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
```

```
            65                  70                  75                  80
Leu Val Tyr Gln Asn Ile Phe Val Ser Met Arg Ala Met Ile Glu Ala
                    85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
            115                 120                 125

Lys Arg Tyr Ala Ala Ala Met Gln Trp Leu Trp Arg Asp Ala Gly Ile
        130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
                195                 200                 205

Val Gly Gly Gln Lys Ser Glu Arg Lys Lys Trp Ile His Cys Phe Glu
        210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Asn Arg Asn Lys Glu Thr
                325                 330                 335

Lys Glu Ile Tyr Ser His Phe Thr Cys Ala Thr Asp Thr Cys Asn Ile
            340                 345                 350

Gln Phe Val Phe Gln Ala Val Thr Asp Val Ile Ile Gln Asn Asn Leu
                355                 360                 365

Lys Tyr Ile Gly Leu Cys
        370

<210> SEQ ID NO 29
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 29

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45
```

-continued

```
Gly Pro Gly Glu Ser Gly Lys Ser Thr Phe Ile Lys Gln Met Arg Ile
         50                  55                  60

Ile His Gly Ala Gly Tyr Ser Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Asn Arg Asn Lys Glu Thr
                325                 330                 335

Lys Glu Ile Tyr Ser His Phe Thr Cys Ala Thr Asp Thr Lys Asn Ile
            340                 345                 350

Gln Phe Val Phe Glu Ala Val Thr Asp Val Ile Ile Gln Asn Asn Leu
        355                 360                 365

Lys Tyr Ile Gly Leu Cys
370
```

<210> SEQ ID NO 30
<211> LENGTH: 374
<212> TYPE: PRT
<213> ORGANISM: Artificial Sequence
<220> FEATURE:
<223> OTHER INFORMATION: Description of Artificial Sequence: G protein chimera

<400> SEQUENCE: 30

```
Met Ala Arg Ser Leu Thr Trp Arg Cys Cys Pro Trp Cys Leu Thr Glu
 1               5                  10                  15

Asp Glu Lys Ala Ala Ala Arg Val Asp Gln Glu Ile Asn Arg Ile Leu
            20                  25                  30
```

```
Leu Glu Gln Lys Lys Gln Asp Arg Gly Glu Leu Lys Leu Leu Leu
         35                  40                  45
Gly Pro Gly Glu Ser Gly Lys Ser Thr Phe Ile Lys Gln Met Arg Ile
 50                  55                  60
Ile His Gly Ala Gly Tyr Ser Glu Glu Arg Lys Gly Phe Arg Pro
 65                  70                  75                  80
Leu Val Tyr Gln Asn Ile Phe Val Ser Met Arg Ala Met Ile Glu Ala
                 85                  90                  95
Met Glu Arg Leu Gln Ile Pro Phe Ser Arg Pro Glu Ser Lys His His
             100                 105                 110
Ala Ser Leu Val Met Ser Gln Asp Pro Tyr Lys Val Thr Thr Phe Glu
         115                 120                 125
Lys Arg Tyr Ala Ala Ala Met Gln Trp Leu Trp Arg Asp Ala Gly Ile
 130                 135                 140
Arg Ala Cys Tyr Glu Arg Arg Arg Glu Phe His Leu Leu Asp Ser Ala
145                 150                 155                 160
Val Tyr Tyr Leu Ser His Leu Glu Arg Ile Thr Glu Glu Gly Tyr Val
                 165                 170                 175
Pro Thr Ala Gln Asp Val Leu Arg Ser Arg Met Pro Thr Thr Gly Ile
             180                 185                 190
Asn Glu Tyr Cys Phe Ser Val Gln Lys Thr Asn Leu Arg Ile Val Asp
         195                 200                 205
Val Gly Gly Gln Lys Ser Glu Arg Lys Lys Trp Ile His Cys Phe Glu
 210                 215                 220
Asn Val Ile Ala Leu Ile Tyr Leu Ala Ser Leu Ser Glu Tyr Asp Gln
225                 230                 235                 240
Cys Leu Glu Glu Asn Asn Gln Glu Asn Arg Met Lys Glu Ser Leu Ala
                 245                 250                 255
Leu Phe Gly Thr Ile Leu Glu Leu Pro Trp Phe Lys Ser Thr Ser Val
             260                 265                 270
Ile Leu Phe Leu Asn Lys Thr Asp Ile Leu Glu Glu Lys Ile Pro Thr
         275                 280                 285
Ser His Leu Ala Thr Tyr Phe Pro Ser Phe Gln Gly Pro Lys Gln Asp
 290                 295                 300
Ala Glu Ala Ala Lys Arg Phe Ile Leu Asp Met Tyr Thr Arg Met Tyr
305                 310                 315                 320
Thr Gly Cys Val Asp Gly Pro Glu Gly Ser Asn Arg Asn Lys Glu Thr
                 325                 330                 335
Lys Glu Ile Tyr Ser His Phe Thr Cys Ala Thr Asp Thr Lys Asn Ile
             340                 345                 350
Gln Phe Val Phe Asn Ala Val Thr Asp Val Ile Ile Gln Asn Asn Leu
         355                 360                 365
Lys Tyr Ile Gly Leu Cys
 370

<210> SEQ ID NO 31
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 31

Met Ala Arg Ser Leu Thr Trp Arg Cys Cys Pro Trp Cys Leu Thr Glu
```

```
              1               5                      10                       15
Asp Glu Lys Ala Ala Arg Val Asp Gln Glu Ile Asn Arg Ile Leu
                    20                  25                  30

Leu Glu Gln Lys Gln Asp Arg Gly Glu Leu Lys Leu Leu Leu
            35                  40                  45

Gly Pro Gly Glu Ser Gly Lys Ser Thr Phe Ile Lys Gln Met Arg Ile
        50                  55                  60

Ile His Gly Ala Gly Tyr Ser Glu Glu Arg Lys Gly Phe Arg Pro
65                  70                  75                  80

Leu Val Tyr Gln Asn Ile Phe Val Ser Met Arg Ala Met Ile Glu Ala
                    85                  90                  95

Met Glu Arg Leu Gln Ile Pro Phe Ser Arg Pro Glu Ser Lys His His
                100                 105                 110

Ala Ser Leu Val Met Ser Gln Asp Pro Tyr Lys Val Thr Thr Phe Glu
            115                 120                 125

Lys Arg Tyr Ala Ala Ala Met Gln Trp Leu Trp Arg Asp Ala Gly Ile
        130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Asn Arg Asn Lys Glu Thr
                325                 330                 335

Lys Glu Ile Tyr Ser His Phe Thr Cys Ala Thr Asp Thr Lys Asn Ile
            340                 345                 350

Gln Phe Val Phe Gln Ala Val Thr Asp Val Ile Ile Gln Asn Asn Leu
        355                 360                 365

Lys Tyr Ile Gly Leu Cys
        370
```

<210> SEQ ID NO 32
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 32

```
Met Ala Arg Ser Leu Thr Trp Arg Cys Cys Pro Trp Cys Leu Thr Glu
 1               5                  10                  15
Asp Glu Lys Ala Ala Arg Val Asp Gln Glu Ile Asn Arg Ile Leu
             20                  25                  30
Leu Glu Gln Lys Lys Gln Asp Arg Gly Glu Leu Lys Leu Leu Leu
         35                  40                  45
Gly Pro Gly Glu Ser Gly Lys Ser Thr Phe Ile Lys Gln Met Arg Ile
 50                  55                  60
Ile His Gly Ala Gly Tyr Ser Glu Glu Arg Lys Gly Phe Arg Pro
 65                  70                  75                  80
Leu Val Tyr Gln Asn Ile Phe Val Ser Met Arg Ala Met Ile Glu Ala
                 85                  90                  95
Met Glu Arg Leu Gln Ile Pro Phe Ser Arg Pro Glu Ser Lys His His
            100                 105                 110
Ala Ser Leu Val Met Ser Gln Asp Pro Tyr Lys Val Thr Thr Phe Glu
        115                 120                 125
Lys Arg Tyr Ala Ala Ala Met Gln Trp Leu Trp Arg Asp Ala Gly Ile
    130                 135                 140
Arg Ala Cys Tyr Glu Arg Arg Glu Phe His Leu Leu Asp Ser Ala
145                 150                 155                 160
Val Tyr Tyr Leu Ser His Leu Glu Arg Ile Thr Glu Glu Gly Tyr Val
                165                 170                 175
Pro Thr Ala Gln Asp Val Leu Arg Ser Arg Met Pro Thr Thr Gly Ile
            180                 185                 190
Asn Glu Tyr Cys Phe Ser Val Gln Lys Thr Asn Leu Arg Ile Val Asp
        195                 200                 205
Val Gly Gly Gln Lys Ser Glu Arg Lys Lys Trp Ile His Cys Phe Glu
    210                 215                 220
Asn Val Ile Ala Leu Ile Tyr Leu Ala Ser Leu Ser Glu Tyr Asp Gln
225                 230                 235                 240
Cys Leu Glu Glu Asn Asn Gln Glu Asn Arg Met Lys Glu Ser Leu Ala
                245                 250                 255
Leu Phe Gly Thr Ile Leu Glu Leu Pro Trp Phe Lys Ser Thr Ser Val
            260                 265                 270
Ile Leu Phe Leu Asn Lys Thr Asp Ile Leu Glu Glu Lys Ile Pro Thr
        275                 280                 285
Ser His Leu Ala Thr Tyr Phe Pro Ser Phe Gln Gly Pro Lys Gln Asp
    290                 295                 300
Ala Glu Ala Ala Lys Arg Phe Ile Leu Asp Met Tyr Thr Arg Met Tyr
305                 310                 315                 320
Thr Gly Cys Val Asp Gly Pro Glu Gly Ser Asn Arg Asn Lys Glu Thr
                325                 330                 335
Lys Glu Ile Tyr Ser His Phe Thr Cys Ala Thr Asp Thr Asn Asn Ile
            340                 345                 350
Gln Phe Val Phe Glu Ala Val Thr Asp Val Ile Ile Gln Asn Asn Leu
        355                 360                 365
Lys Tyr Ile Gly Leu Cys
    370
```

<210> SEQ ID NO 33
<211> LENGTH: 374
<212> TYPE: PRT

```
<213> ORGANISM: Artificial Sequence
<220> FEATURE:
<223> OTHER INFORMATION: Description of Artificial Sequence: G protein
      chimera

<400> SEQUENCE: 33

Met Ala Arg Ser Leu Thr Trp Arg Cys Cys Pro Trp Cys Leu Thr Glu
 1               5                  10                  15

Asp Glu Lys Ala Ala Arg Val Asp Gln Glu Ile Asn Arg Ile Leu
             20                  25                  30

Leu Glu Gln Lys Lys Gln Asp Arg Gly Glu Leu Lys Leu Leu Leu
             35                  40                  45

Gly Pro Gly Glu Ser Gly Lys Ser Thr Phe Ile Lys Gln Met Arg Ile
 50                  55                  60

Ile His Gly Ala Gly Tyr Ser Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
                100                 105                 110

Ala Ser Leu Val Met Ser Gln Asp Pro Tyr Lys Val Thr Thr Phe Glu
            115                 120                 125

Lys Arg Tyr Ala Ala Ala Met Gln Trp Leu Trp Arg Asp Ala Gly Ile
130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
                180                 185                 190

Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
                260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
            290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Asn Arg Asn Lys Glu Thr
                325                 330                 335

Lys Glu Ile Tyr Ser His Phe Thr Cys Ala Thr Asp Thr Asn Asn Ile
            340                 345                 350

Gln Phe Val Phe Asn Ala Val Thr Asp Val Ile Ile Gln Asn Asn Leu
            355                 360                 365

Lys Tyr Ile Gly Leu Cys
    370
```

```
<210> SEQ ID NO 34
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 34
```

```
Met Ala Arg Ser Leu Thr Trp Arg Cys Cys Pro Trp Cys Leu Thr Glu
 1               5                  10                  15

Asp Glu Lys Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu
        35                  40                  45

Gly Pro Gly Glu Ser Gly Lys Ser Thr Phe Ile Lys Gln Met Arg Ile
50                  55                  60

Ile His Gly Ala Gly Tyr Ser Glu Glu Arg Lys Gly Phe Arg Pro
65              70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Asn Arg Asn Lys Glu Thr
                325                 330                 335

Lys Glu Ile Tyr Ser His Phe Thr Cys Ala Thr Asp Thr Asn Asn Ile
            340                 345                 350

Gln Phe Val Phe Gln Ala Val Thr Asp Val Ile Ile Gln Asn Asn Leu
        355                 360                 365
```

Lys Tyr Ile Gly Leu Cys
    370

<210> SEQ ID NO 35
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 35

Met Ala Arg Ser Leu Thr Trp Arg Cys Cys Pro Trp Cys Leu Thr Glu
 1               5                  10                  15

Asp Glu Lys Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu
        35                  40                  45

Gly Pro Gly Glu Ser Gly Lys Ser Thr Phe Ile Lys Gln Met Arg Ile
 50                  55                  60

Ile His Gly Ala Gly Tyr Ser Glu Glu Arg Lys Gly Phe Arg Pro
65                  70                  75                  80

Leu Val Tyr Gln Asn Ile Phe Val Ser Met Arg Ala Met Ile Glu Ala
                    85                  90                  95

Met Glu Arg Leu Gln Ile Pro Phe Ser Arg Pro Glu Ser Lys His His
                100                 105                 110

Ala Ser Leu Val Met Ser Gln Asp Pro Tyr Lys Val Thr Thr Phe Glu
            115                 120                 125

Lys Arg Tyr Ala Ala Ala Met Gln Trp Leu Trp Arg Asp Ala Gly Ile
130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Asp Asn Ile

-continued

```
                    340                 345                 350
Arg Arg Val Phe Asn Asp Cys Arg Asp Ile Ile Gln Arg Met His Leu
            355                 360                 365
Arg Gln Tyr Glu Leu Leu
        370

<210> SEQ ID NO 36
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 36

Met Ala Arg Ser Leu Thr Trp Arg Cys Cys Pro Trp Cys Leu Thr Glu
  1               5                  10                  15

Asp Glu Lys Ala Ala Arg Val Asp Gln Glu Ile Asn Arg Ile Leu
             20                  25                  30

Leu Glu Gln Lys Lys Gln Asp Arg Gly Glu Leu Lys Leu Leu Leu
         35                  40                  45

Gly Pro Gly Glu Ser Gly Lys Ser Thr Phe Ile Lys Gln Met Arg Ile
 50                  55                  60

Ile His Gly Ala Gly Tyr Ser Glu Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320
```

```
Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Glu Asn Ile
            340                 345                 350

Arg Arg Val Phe Gln Asp Cys Arg Asp Ile Ile Gln Arg Met His Leu
            355                 360                 365

Arg Gln Tyr Glu Leu Leu
    370

<210> SEQ ID NO 37
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 37

Met Ala Arg Ser Leu Thr Trp Arg Cys Cys Pro Trp Cys Leu Thr Glu
  1               5                  10                  15

Asp Glu Lys Ala Ala Ala Arg Val Asp Gln Glu Ile Asn Arg Ile Leu
             20                  25                  30

Leu Glu Gln Lys Lys Gln Asp Arg Gly Glu Leu Lys Leu Leu Leu Leu
         35                  40                  45

Gly Pro Gly Glu Ser Gly Lys Ser Thr Phe Ile Lys Gln Met Arg Ile
     50                  55                  60

Ile His Gly Ala Gly Tyr Ser Glu Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
                100                 105                 110

Ala Ser Leu Val Met Ser Gln Asp Pro Tyr Lys Val Thr Thr Phe Glu
            115                 120                 125

Lys Arg Tyr Ala Ala Ala Met Gln Trp Leu Trp Arg Asp Ala Gly Ile
        130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300
```

```
Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
            325                 330                 335

Arg Arg Leu Phe Ser His Tyr Thr Cys Ala Thr Asp Thr Glu Asn Ile
            340                 345                 350

Arg Arg Val Phe Asp Asp Cys Arg Asp Ile Ile Gln Arg Met His Leu
            355                 360                 365

Arg Gln Tyr Glu Leu Leu
        370
```

<210> SEQ ID NO 38
<211> LENGTH: 374
<212> TYPE: PRT
<213> ORGANISM: Artificial Sequence
<220> FEATURE:
<223> OTHER INFORMATION: Description of Artificial Sequence: G protein chimera

<400> SEQUENCE: 38

```
Met Ala Arg Ser Leu Thr Trp Arg Cys Cys Pro Trp Cys Leu Thr Glu
 1               5                  10                  15

Asp Glu Lys Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Met Gln Trp Leu Trp Arg Asp Ala Gly Ile
130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
```

```
              275                 280                 285
Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Glu Asn Ile
            340                 345                 350

Arg Arg Val Phe Glu Asp Cys Arg Asp Ile Ile Gln Arg Met His Leu
        355                 360                 365

Arg Gln Tyr Glu Leu Leu
    370

<210> SEQ ID NO 39
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 39

Met Ala Arg Ser Leu Thr Trp Arg Cys Cys Pro Trp Cys Leu Thr Glu
  1               5                  10                  15

Asp Glu Lys Ala Ala Arg Val Asp Gln Glu Ile Asn Arg Ile Leu
             20                  25                  30

Leu Glu Gln Lys Lys Gln Asp Arg Gly Glu Leu Lys Leu Leu Leu
         35                  40                  45

Gly Pro Gly Glu Ser Gly Lys Ser Thr Phe Ile Lys Gln Met Arg Ile
     50                  55                  60

Ile His Gly Ala Gly Tyr Ser Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255
```

```
Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
            290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Glu Asn Ile
            340                 345                 350

Arg Arg Val Phe Asn Asp Cys Arg Asp Ile Ile Asn Arg Met His Leu
            355                 360                 365

Arg Gln Tyr Glu Leu Leu
        370
```

<210> SEQ ID NO 40
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 40

```
Met Ala Arg Ser Leu Thr Trp Arg Cys Cys Pro Trp Cys Leu Thr Glu
  1               5                  10                  15

Asp Glu Lys Ala Ala Arg Val Asp Gln Glu Ile Asn Arg Ile Leu
             20                  25                  30

Leu Glu Gln Lys Lys Gln Asp Arg Gly Glu Leu Lys Leu Leu Leu
         35                  40                  45

Gly Pro Gly Glu Ser Gly Lys Ser Thr Phe Ile Lys Gln Met Arg Ile
 50                  55                  60

Ile His Gly Ala Gly Tyr Ser Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
            115                 120                 125

Lys Arg Tyr Ala Ala Ala Met Gln Trp Leu Trp Arg Asp Ala Gly Ile
            130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
            210                 215                 220

Asn Val Ile Ala Leu Ile Tyr Leu Ala Ser Leu Ser Glu Tyr Asp Gln
225                 230                 235                 240
```

-continued

```
Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Glu Asn Ile
            340                 345                 350

Arg Arg Val Phe Asn Asp Cys Arg Asp Ile Ile Asp Arg Met His Leu
        355                 360                 365

Arg Gln Tyr Glu Leu Leu
    370

<210> SEQ ID NO 41
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 41

Met Ala Arg Ser Leu Thr Trp Arg Cys Cys Pro Trp Cys Leu Thr Glu
  1               5                  10                  15

Asp Glu Lys Ala Ala Ala Arg Val Asp Gln Glu Ile Asn Arg Ile Leu
                 20                  25                  30

Leu Glu Gln Lys Lys Gln Asp Arg Gly Glu Leu Lys Leu Leu Leu Leu
             35                  40                  45

Gly Pro Gly Glu Ser Gly Lys Ser Thr Phe Ile Lys Gln Met Arg Ile
         50                  55                  60

Ile His Gly Ala Gly Tyr Ser Glu Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
                100                 105                 110

Ala Ser Leu Val Met Ser Gln Asp Pro Tyr Lys Val Thr Thr Phe Glu
            115                 120                 125

Lys Arg Tyr Ala Ala Ala Met Gln Trp Leu Trp Arg Asp Ala Gly Ile
        130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
```

-continued

```
                 210                 215                 220
Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
                260                 265                 270

Ile Leu Phe Leu Asn Lys Thr Asp Ile Leu Glu Glu Lys Ile Pro Thr
                275                 280                 285

Ser His Leu Ala Thr Tyr Phe Pro Ser Phe Gln Gly Pro Lys Gln Asp
                290                 295                 300

Ala Glu Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Glu Asn Ile
                340                 345                 350

Arg Arg Val Phe Asn Asp Cys Arg Asp Ile Ile Glu Arg Met His Leu
                355                 360                 365

Arg Gln Tyr Glu Leu Leu
    370
```

<210> SEQ ID NO 42
<211> LENGTH: 374
<212> TYPE: PRT
<213> ORGANISM: Artificial Sequence
<220> FEATURE:
<223> OTHER INFORMATION: Description of Artificial Sequence: G protein chimera

<400> SEQUENCE: 42

```
Met Ala Arg Ser Leu Thr Trp Arg Cys Cys Pro Trp Cys Leu Thr Glu
1               5                   10                  15

Asp Glu Lys Ala Ala Arg Val Asp Gln Glu Ile Asn Arg Ile Leu
                20                  25                  30

Leu Glu Gln Lys Lys Gln Asp Arg Gly Glu Leu Lys Leu Leu Leu Leu
            35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
                100                 105                 110

Ala Ser Leu Val Met Ser Gln Asp Pro Tyr Lys Val Thr Thr Phe Glu
            115                 120                 125

Lys Arg Tyr Ala Ala Ala Met Gln Trp Leu Trp Arg Asp Ala Gly Ile
130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190
```

```
Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
            210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
            245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
            290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
            325                 330                 335

Arg Arg Leu Phe Ser His Tyr Thr Cys Ala Thr Asp Thr Asp Asn Ile
            340                 345                 350

Arg Arg Val Phe Gln Asp Cys Arg Asp Ile Ile Gln Arg Met His Leu
            355                 360                 365

Arg Gln Tyr Glu Leu Leu
    370

<210> SEQ ID NO 43
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 43

Met Ala Arg Ser Leu Thr Trp Arg Cys Cys Pro Trp Cys Leu Thr Glu
 1               5                  10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
            35                  40                  45

Gly Pro Gly Glu Ser Gly Lys Ser Thr Phe Ile Lys Gln Met Arg Ile
        50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
            115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175
```

-continued

```
Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Asp Asn Ile
            340                 345                 350

Arg Arg Val Phe Asp Asp Cys Arg Asp Ile Ile Gln Arg Met His Leu
        355                 360                 365

Arg Gln Tyr Glu Leu Leu
    370

<210> SEQ ID NO 44
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 44

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
```

-continued

```
            145                 150                 155                 160
Val Tyr Tyr Leu Ser His Leu Glu Arg Ile Thr Glu Glu Gly Tyr Val
                    165                 170                 175

Pro Thr Ala Gln Asp Val Leu Arg Ser Arg Met Pro Thr Thr Gly Ile
                180                 185                 190

Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
        210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
                260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
        290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Asp Asn Ile
                340                 345                 350

Arg Arg Val Phe Glu Asp Cys Arg Asp Ile Ile Gln Arg Met His Leu
            355                 360                 365

Arg Gln Tyr Glu Leu Leu
    370

<210> SEQ ID NO 45
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 45

Met Ala Arg Ser Leu Thr Trp Arg Cys Cys Pro Trp Cys Leu Thr Glu
  1               5                  10                  15

Asp Glu Lys Ala Ala Ala Arg Val Asp Gln Glu Ile Asn Arg Ile Leu
                 20                  25                  30

Leu Glu Gln Lys Lys Gln Asp Arg Gly Glu Leu Lys Leu Leu Leu Leu
             35                  40                  45

Gly Pro Gly Glu Ser Gly Lys Ser Thr Phe Ile Lys Gln Met Arg Ile
         50                  55                  60

Ile His Gly Ala Gly Tyr Ser Glu Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
                100                 105                 110

Ala Ser Leu Val Met Ser Gln Asp Pro Tyr Lys Val Thr Thr Phe Glu
            115                 120                 125
```

-continued

```
Lys Arg Tyr Ala Ala Ala Met Gln Trp Leu Trp Arg Asp Ala Gly Ile
    130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
                195                 200                 205

Val Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
    275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Asp Asn Ile
            340                 345                 350

Arg Arg Val Phe Asn Asp Cys Arg Asp Ile Ile Asn Arg Met His Leu
    355                 360                 365

Arg Gln Tyr Glu Leu Leu
    370
```

<210> SEQ ID NO 46
<211> LENGTH: 374
<212> TYPE: PRT
<213> ORGANISM: Artificial Sequence
<220> FEATURE:
<223> OTHER INFORMATION: Description of Artificial Sequence: G protein chimera

<400> SEQUENCE: 46

```
Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
                20                  25                  30

Leu Glu Gln Lys Lys Gln Asp Arg Gly Glu Leu Lys Leu Leu Leu Leu
            35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110
```

```
Ala Ser Leu Val Met Ser Gln Asp Pro Tyr Lys Val Thr Thr Phe Glu
        115                 120                 125

Lys Arg Tyr Ala Ala Met Gln Trp Leu Trp Arg Asp Ala Gly Ile
    130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Asp Asn Ile
            340                 345                 350

Arg Arg Val Phe Asn Asp Cys Arg Asp Ile Ile Asp Arg Met His Leu
        355                 360                 365

Arg Gln Tyr Glu Leu Leu
    370

<210> SEQ ID NO 47
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 47

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
                20                  25                  30

Leu Glu Gln Lys Lys Gln Asp Arg Gly Glu Leu Lys Leu Leu Leu Leu
            35                  40                  45

Gly Pro Gly Glu Ser Gly Lys Ser Thr Phe Ile Lys Gln Met Arg Ile
        50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
```

```
                        85                  90                  95
Met Glu Arg Leu Gln Ile Pro Phe Ser Arg Pro Glu Ser Lys His His
                100                 105                 110

Ala Ser Leu Val Met Ser Gln Asp Pro Tyr Lys Val Thr Thr Phe Glu
        115                 120                 125

Lys Arg Tyr Ala Ala Met Gln Trp Leu Trp Arg Asp Ala Gly Ile
    130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
                195                 200                 205

Val Gly Gly Gln Lys Ser Glu Arg Lys Lys Trp Ile His Cys Phe Glu
            210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
                260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Asp Asn Ile
            340                 345                 350

Arg Arg Val Phe Asn Asp Cys Arg Asp Ile Ile Glu Arg Met His Leu
            355                 360                 365

Arg Gln Tyr Glu Leu Leu
    370

<210> SEQ ID NO 48
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 48

Met Ala Arg Ser Leu Thr Trp Arg Cys Cys Pro Trp Cys Leu Thr Glu
 1               5                  10                  15

Asp Glu Lys Ala Ala Ala Arg Val Asp Gln Glu Ile Asn Arg Ile Leu
                20                  25                  30

Leu Glu Gln Lys Lys Gln Asp Arg Gly Glu Leu Lys Leu Leu Leu Leu
            35                  40                  45

Gly Pro Gly Glu Ser Gly Lys Ser Thr Phe Ile Lys Gln Met Arg Ile
        50                  55                  60
```

```
Ile His Gly Ala Gly Tyr Ser Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
            115                 120                 125

Lys Arg Tyr Ala Ala Met Gln Trp Leu Trp Arg Asp Ala Gly Ile
130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
            210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
            290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Glu Asn Ile
            340                 345                 350

Arg Arg Val Phe Gln Asp Cys Arg Asp Ile Ile Asn Arg Met His Leu
            355                 360                 365

Arg Gln Tyr Glu Leu Leu
    370

<210> SEQ ID NO 49
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 49

Met Ala Arg Ser Leu Thr Trp Arg Cys Cys Pro Trp Cys Leu Thr Glu
  1               5                  10                  15

Asp Glu Lys Ala Ala Ala Arg Val Asp Gln Glu Ile Asn Arg Ile Leu
                 20                  25                  30

Leu Glu Gln Lys Lys Gln Asp Arg Gly Glu Leu Lys Leu Leu Leu Leu
             35                  40                  45
```

-continued

```
Gly Pro Gly Glu Ser Gly Lys Ser Thr Phe Ile Lys Gln Met Arg Ile
         50                  55                  60

Ile His Gly Ala Gly Tyr Ser Glu Glu Arg Lys Gly Phe Arg Pro
 65                  70                  75                  80

Leu Val Tyr Gln Asn Ile Phe Val Ser Met Arg Ala Met Ile Glu Ala
                     85                  90                  95

Met Glu Arg Leu Gln Ile Pro Phe Ser Arg Pro Glu Ser Lys His His
                100                 105                 110

Ala Ser Leu Val Met Ser Gln Asp Pro Tyr Lys Val Thr Thr Phe Glu
            115                 120                 125

Lys Arg Tyr Ala Ala Met Gln Trp Leu Trp Arg Asp Ala Gly Ile
130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
                195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
                275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Glu Asn Ile
            340                 345                 350

Arg Arg Val Phe Gln Asp Cys Arg Asp Ile Ile Asp Arg Met His Leu
                355                 360                 365

Arg Gln Tyr Glu Leu Leu
    370
```

<210> SEQ ID NO 50
<211> LENGTH: 374
<212> TYPE: PRT
<213> ORGANISM: Artificial Sequence
<220> FEATURE:
<223> OTHER INFORMATION: Description of Artificial Sequence: G protein chimera

<400> SEQUENCE: 50

```
Met Ala Arg Ser Leu Thr Trp Arg Cys Cys Pro Trp Cys Leu Thr Glu
 1               5                  10                  15

Asp Glu Lys Ala Ala Ala Arg Val Asp Gln Glu Ile Asn Arg Ile Leu
```

```
                  20                  25                  30
Leu Glu Gln Lys Lys Gln Asp Arg Gly Glu Leu Lys Leu Leu Leu
            35                  40                  45
Gly Pro Gly Glu Ser Gly Lys Ser Thr Phe Ile Lys Gln Met Arg Ile
 50                  55                  60
Ile His Gly Ala Gly Tyr Ser Glu Glu Arg Lys Gly Phe Arg Pro
 65                  70                  75                  80
Leu Val Tyr Gln Asn Ile Phe Val Ser Met Arg Ala Met Ile Glu Ala
                85                  90                  95
Met Glu Arg Leu Gln Ile Pro Phe Ser Arg Pro Glu Ser Lys His His
            100                 105                 110
Ala Ser Leu Val Met Ser Gln Asp Pro Tyr Lys Val Thr Thr Phe Glu
            115                 120                 125
Lys Arg Tyr Ala Ala Ala Met Gln Trp Leu Trp Arg Asp Ala Gly Ile
            130                 135                 140
Arg Ala Cys Tyr Glu Arg Arg Arg Glu Phe His Leu Leu Asp Ser Ala
145                 150                 155                 160
Val Tyr Tyr Leu Ser His Leu Glu Arg Ile Thr Glu Glu Gly Tyr Val
                165                 170                 175
Pro Thr Ala Gln Asp Val Leu Arg Ser Arg Met Pro Thr Thr Gly Ile
            180                 185                 190
Asn Glu Tyr Cys Phe Ser Val Gln Lys Thr Asn Leu Arg Ile Val Asp
            195                 200                 205
Val Gly Gly Gln Lys Ser Glu Arg Lys Lys Trp Ile His Cys Phe Glu
            210                 215                 220
Asn Val Ile Ala Leu Ile Tyr Leu Ala Ser Leu Ser Glu Tyr Asp Gln
225                 230                 235                 240
Cys Leu Glu Glu Asn Asn Gln Glu Asn Arg Met Lys Glu Ser Leu Ala
                245                 250                 255
Leu Phe Gly Thr Ile Leu Glu Leu Pro Trp Phe Lys Ser Thr Ser Val
            260                 265                 270
Ile Leu Phe Leu Asn Lys Thr Asp Ile Leu Glu Glu Lys Ile Pro Thr
            275                 280                 285
Ser His Leu Ala Thr Tyr Phe Pro Ser Phe Gln Gly Pro Lys Gln Asp
            290                 295                 300
Ala Glu Ala Ala Lys Arg Phe Ile Leu Asp Met Tyr Thr Arg Met Tyr
305                 310                 315                 320
Thr Gly Cys Val Asp Gly Pro Glu Gly Ser Lys Lys Gly Ala Arg Ser
                325                 330                 335
Arg Arg Leu Phe Ser His Tyr Thr Cys Ala Thr Asp Thr Glu Asn Ile
            340                 345                 350
Arg Arg Val Phe Gln Asp Cys Arg Asp Ile Ile Glu Arg Met His Leu
            355                 360                 365
Arg Gln Tyr Glu Leu Leu
            370

<210> SEQ ID NO 51
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 51
```

```
Met Ala Arg Ser Leu Thr Trp Arg Cys Cys Pro Trp Cys Leu Thr Glu
 1               5                  10                  15

Asp Glu Lys Ala Ala Ala Arg Val Asp Gln Glu Ile Asn Arg Ile Leu
                20                  25                  30

Leu Glu Gln Lys Lys Gln Asp Arg Gly Glu Leu Lys Leu Leu Leu Leu
            35                  40                  45

Gly Pro Gly Glu Ser Gly Lys Ser Thr Phe Ile Lys Gln Met Arg Ile
 50                  55                  60

Ile His Gly Ala Gly Tyr Ser Glu Glu Glu Arg Lys Gly Phe Arg Pro
 65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
               100                 105                 110

Ala Ser Leu Val Met Ser Gln Asp Pro Tyr Lys Val Thr Thr Phe Glu
            115                 120                 125

Lys Arg Tyr Ala Ala Ala Met Gln Trp Leu Trp Arg Asp Ala Gly Ile
130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
            245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Glu Asn Ile
            340                 345                 350

Arg Arg Val Phe Asp Asp Cys Arg Asp Ile Ile Asn Arg Met His Leu
            355                 360                 365

Arg Gln Tyr Glu Leu Leu
370

<210> SEQ ID NO 52
<211> LENGTH: 374
<212> TYPE: PRT
<213> ORGANISM: Artificial Sequence
<220> FEATURE:
<223> OTHER INFORMATION: Description of Artificial Sequence: G protein
``` chimera

<400> SEQUENCE: 52

Met Ala Arg Ser Leu Thr Trp Arg Cys Cys Pro Trp Cys Leu Thr Glu
1               5                   10                  15

Asp Glu Lys Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Glu Asn Ile
            340                 345                 350

Arg Arg Val Phe Asp Asp Cys Arg Asp Ile Ile Asp Arg Met His Leu
        355                 360                 365

Arg Gln Tyr Glu Leu Leu
    370

<210> SEQ ID NO 53
<211> LENGTH: 374

```
<212> TYPE: PRT
<213> ORGANISM: Artificial Sequence
<220> FEATURE:
<223> OTHER INFORMATION: Description of Artificial Sequence: G protein
      chimera

<400> SEQUENCE: 53

Met Ala Arg Ser Leu Thr Trp Arg Cys Cys Pro Trp Cys Leu Thr Glu
 1               5                  10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
 50                  55                  60

Ile His Gly Ala Gly Tyr Ser Glu Glu Arg Lys Gly Phe Arg Pro
 65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Glu Asn Ile
            340                 345                 350

Arg Arg Val Phe Asp Asp Cys Arg Asp Ile Ile Glu Arg Met His Leu
        355                 360                 365

Arg Gln Tyr Glu Leu Leu
    370
```

```
<210> SEQ ID NO 54
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 54

Met Ala Arg Ser Leu Thr Trp Arg Cys Cys Pro Trp Cys Leu Thr Glu
 1               5                   10                  15

Asp Glu Lys Ala Ala Ala Arg Val Asp Gln Glu Ile Asn Arg Ile Leu
                20                  25                  30

Leu Glu Gln Lys Lys Gln Asp Arg Gly Glu Leu Lys Leu Leu Leu Leu
            35                  40                  45

Gly Pro Gly Glu Ser Gly Lys Ser Thr Phe Ile Lys Gln Met Arg Ile
 50                  55                  60

Ile His Gly Ala Gly Tyr Ser Glu Glu Arg Lys Gly Phe Arg Pro
 65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Glu Asn Ile
            340                 345                 350

Arg Arg Val Phe Glu Asp Cys Arg Asp Ile Ile Asn Arg Met His Leu
```

Arg Gln Tyr Glu Leu Leu
        370

<210> SEQ ID NO 55
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 55

Met Ala Arg Ser Leu Thr Trp Arg Cys Cys Pro Trp Cys Leu Thr Glu
 1               5                  10                  15

Asp Glu Lys Ala Ala Arg Val Asp Gln Glu Ile Asn Arg Ile Leu
                20                  25                  30

Leu Glu Gln Lys Lys Gln Asp Arg Gly Glu Leu Lys Leu Leu Leu
            35                  40                  45

Gly Pro Gly Glu Ser Gly Lys Ser Thr Phe Ile Lys Gln Met Arg Ile
        50                  55                  60

Ile His Gly Ala Gly Tyr Ser Glu Glu Glu Arg Lys Gly Phe Arg Pro
 65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

```
Arg Arg Leu Phe Ser His Tyr Thr Cys Ala Thr Asp Thr Glu Asn Ile
            340                 345                 350

Arg Arg Val Phe Glu Asp Cys Arg Asp Ile Ile Asp Arg Met His Leu
            355                 360                 365

Arg Gln Tyr Glu Leu Leu
            370

<210> SEQ ID NO 56
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 56

Met Ala Arg Ser Leu Thr Trp Arg Cys Cys Pro Trp Cys Leu Thr Glu
  1               5                  10                  15

Asp Glu Lys Ala Ala Arg Val Asp Gln Glu Ile Asn Arg Ile Leu
                 20                  25                  30

Leu Glu Gln Lys Lys Gln Asp Arg Gly Glu Leu Lys Leu Leu Leu
             35                  40                  45

Gly Pro Gly Glu Ser Gly Lys Ser Thr Phe Ile Lys Gln Met Arg Ile
     50                  55                  60

Ile His Gly Ala Gly Tyr Ser Glu Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
            115                 120                 125

Lys Arg Tyr Ala Ala Ala Met Gln Trp Leu Trp Arg Asp Ala Gly Ile
            130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
        210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
            245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
            290                 295                 300

Ala Glu Ala Ala Lys Arg Phe Ile Leu Asp Met Tyr Thr Arg Met Tyr
305                 310                 315                 320
```

```
Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Glu Asn Ile
            340                 345                 350

Arg Arg Val Phe Glu Asp Cys Arg Asp Ile Ile Glu Arg Met His Leu
            355                 360                 365

Arg Gln Tyr Glu Leu Leu
        370
```

<210> SEQ ID NO 57
<211> LENGTH: 374
<212> TYPE: PRT
<213> ORGANISM: Artificial Sequence
<220> FEATURE:
<223> OTHER INFORMATION: Description of Artificial Sequence: G protein chimera

<400> SEQUENCE: 57

```
Met Ala Arg Ser Leu Thr Trp Arg Cys Cys Pro Trp Cys Leu Thr Glu
  1               5                  10                  15

Asp Glu Lys Ala Ala Ala Arg Val Asp Gln Glu Ile Asn Arg Ile Leu
             20                  25                  30

Leu Glu Gln Lys Lys Gln Asp Arg Gly Glu Leu Lys Leu Leu Leu Leu
         35                  40                  45

Gly Pro Gly Glu Ser Gly Lys Ser Thr Phe Ile Lys Gln Met Arg Ile
     50                  55                  60

Ile His Gly Ala Gly Tyr Ser Glu Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
```

```
                290                 295                 300
Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
            325                 330                 335

Arg Arg Leu Phe Ser His Tyr Thr Cys Ala Thr Asp Thr Asp Asn Ile
                340                 345                 350

Arg Arg Val Phe Gln Asp Cys Arg Asp Ile Ile Asn Arg Met His Leu
        355                 360                 365

Arg Gln Tyr Glu Leu Leu
    370

<210> SEQ ID NO 58
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 58

Met Ala Arg Ser Leu Thr Trp Arg Cys Cys Pro Trp Cys Leu Thr Glu
1               5                   10                  15

Asp Glu Lys Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu
        35                  40                  45

Gly Pro Gly Glu Ser Gly Lys Ser Thr Phe Ile Lys Gln Met Arg Ile
50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270
```

```
Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
        290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Asp Asn Ile
                340                 345                 350

Arg Arg Val Phe Asp Asp Cys Arg Asp Ile Ile Asn Arg Met His Leu
                355                 360                 365

Arg Gln Tyr Glu Leu Leu
        370

<210> SEQ ID NO 59
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 59

Met Ala Arg Ser Leu Thr Trp Arg Cys Cys Pro Trp Cys Leu Thr Glu
 1               5                  10                  15

Asp Glu Lys Ala Ala Arg Val Asp Gln Glu Ile Asn Arg Ile Leu
                20                  25                  30

Leu Glu Gln Lys Lys Gln Asp Arg Gly Glu Leu Lys Leu Leu Leu Leu
            35                  40                  45

Gly Pro Gly Glu Ser Gly Lys Ser Thr Phe Ile Lys Gln Met Arg Ile
 50                  55                  60

Ile His Gly Ala Gly Tyr Ser Glu Glu Glu Arg Lys Gly Phe Arg Pro
 65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255
```

```
Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Asp Asn Ile
            340                 345                 350

Arg Arg Val Phe Glu Asp Cys Arg Asp Ile Ile Asn Arg Met His Leu
            355                 360                 365

Arg Gln Tyr Glu Leu Leu
            370

<210> SEQ ID NO 60
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 60

Met Ala Arg Ser Leu Thr Trp Arg Cys Cys Pro Trp Cys Leu Thr Glu
  1               5                  10                  15

Asp Glu Lys Ala Ala Arg Val Asp Gln Glu Ile Asn Arg Ile Leu
             20                  25                  30

Leu Glu Gln Lys Lys Gln Asp Arg Gly Glu Leu Lys Leu Leu Leu Leu
             35                  40                  45

Gly Pro Gly Glu Ser Gly Lys Ser Thr Phe Ile Lys Gln Met Arg Ile
     50                  55                  60

Ile His Gly Ala Gly Tyr Ser Glu Glu Glu Arg Lys Gly Phe Arg Pro
 65              70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
```

```
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Asp Asn Ile
            340                 345                 350

Arg Arg Val Phe Asp Asp Cys Arg Asp Ile Ile Asp Arg Met His Leu
        355                 360                 365

Arg Gln Tyr Glu Leu Leu
    370

<210> SEQ ID NO 61
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 61

Met Ala Arg Ser Leu Thr Trp Arg Cys Cys Pro Trp Cys Leu Thr Glu
  1               5                  10                  15

Asp Glu Lys Ala Ala Arg Val Asp Gln Glu Ile Asn Arg Ile Leu
                20                  25                  30

Leu Glu Gln Lys Lys Gln Asp Arg Gly Glu Leu Lys Leu Leu Leu
        35                  40                  45

Gly Pro Gly Glu Ser Gly Lys Ser Thr Phe Ile Lys Gln Met Arg Ile
 50                  55                  60

Ile His Gly Ala Gly Tyr Ser Glu Glu Glu Arg Lys Gly Phe Arg Pro
 65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205
```

-continued

```
Val Gly Gly Gln Lys Ser Glu Arg Lys Lys Trp Ile His Cys Phe Glu
        210                 215                 220
Asn Val Ile Ala Leu Ile Tyr Leu Ala Ser Leu Ser Glu Tyr Asp Gln
225                 230                 235                 240
Cys Leu Glu Glu Asn Asn Gln Glu Asn Arg Met Lys Glu Ser Leu Ala
                245                 250                 255
Leu Phe Gly Thr Ile Leu Glu Leu Pro Trp Phe Lys Ser Thr Ser Val
            260                 265                 270
Ile Leu Phe Leu Asn Lys Thr Asp Ile Leu Glu Glu Lys Ile Pro Thr
        275                 280                 285
Ser His Leu Ala Thr Tyr Phe Pro Ser Phe Gln Gly Pro Lys Gln Asp
    290                 295                 300
Ala Glu Ala Ala Lys Arg Phe Ile Leu Asp Met Tyr Thr Arg Met Tyr
305                 310                 315                 320
Thr Gly Cys Val Asp Gly Pro Glu Gly Ser Lys Lys Gly Ala Arg Ser
                325                 330                 335
Arg Arg Leu Phe Ser His Tyr Thr Cys Ala Thr Asp Thr Asp Asn Ile
            340                 345                 350
Arg Arg Val Phe Asp Asp Cys Arg Asp Ile Ile Glu Arg Met His Leu
        355                 360                 365
Arg Gln Tyr Glu Leu Leu
        370
```

<210> SEQ ID NO 62
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 62

```
Met Ala Arg Ser Leu Thr Trp Arg Cys Cys Pro Trp Cys Leu Thr Glu
  1               5                  10                  15
Asp Glu Lys Ala Ala Ala Arg Val Asp Gln Glu Ile Asn Arg Ile Leu
                20                  25                  30
Leu Glu Gln Lys Lys Gln Asp Arg Gly Glu Leu Lys Leu Leu Leu Leu
            35                  40                  45
Gly Pro Gly Glu Ser Gly Lys Ser Thr Phe Ile Lys Gln Met Arg Ile
    50                  55                  60
Ile His Gly Ala Gly Tyr Ser Glu Glu Glu Arg Lys Gly Phe Arg Pro
65                  70                  75                  80
Leu Val Tyr Gln Asn Ile Phe Val Ser Met Arg Ala Met Ile Glu Ala
                85                  90                  95
Met Glu Arg Leu Gln Ile Pro Phe Ser Arg Pro Glu Ser Lys His His
                100                 105                 110
Ala Ser Leu Val Met Ser Gln Asp Pro Tyr Lys Val Thr Thr Phe Glu
            115                 120                 125
Lys Arg Tyr Ala Ala Ala Met Gln Trp Leu Trp Arg Asp Ala Gly Ile
        130                 135                 140
Arg Ala Cys Tyr Glu Arg Arg Arg Glu Phe His Leu Leu Asp Ser Ala
145                 150                 155                 160
Val Tyr Tyr Leu Ser His Leu Glu Arg Ile Thr Glu Glu Gly Tyr Val
                165                 170                 175
Pro Thr Ala Gln Asp Val Leu Arg Ser Arg Met Pro Thr Thr Gly Ile
            180                 185                 190
```

```
Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Asp Asn Ile
            340                 345                 350

Arg Arg Val Phe Glu Asp Cys Arg Asp Ile Ile Asp Arg Met His Leu
        355                 360                 365

Arg Gln Tyr Glu Leu Leu
        370

<210> SEQ ID NO 63
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 63

Met Ala Arg Ser Leu Thr Trp Arg Cys Cys Pro Trp Cys Leu Thr Glu
 1               5                  10                  15

Asp Glu Lys Ala Ala Ala Arg Val Asp Gln Glu Ile Asn Arg Ile Leu
                20                  25                  30

Leu Glu Gln Lys Lys Gln Asp Arg Gly Glu Leu Lys Leu Leu Leu Leu
            35                  40                  45

Gly Pro Gly Glu Ser Gly Lys Ser Thr Phe Ile Lys Gln Met Arg Ile
        50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
```

```
                        165                 170                 175
Pro Thr Ala Gln Asp Val Leu Arg Ser Arg Met Pro Thr Thr Gly Ile
                180                 185                 190

Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
                260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
        290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Asp Asn Ile
                340                 345                 350

Arg Arg Val Phe Glu Asp Cys Arg Asp Ile Ile Glu Arg Met His Leu
            355                 360                 365

Arg Gln Tyr Glu Leu Leu
    370

<210> SEQ ID NO 64
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 64

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140
```

```
Arg Ala Cys Tyr Glu Arg Arg Glu Phe His Leu Asp Ser Ala
145                 150                 155                 160

Val Tyr Tyr Leu Ser His Leu Glu Arg Ile Thr Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Ala Ser Gly Asp Gly Arg
                325                 330                 335

His Tyr Cys Tyr Pro His Phe Thr Cys Ala Val Asp Thr Asp Asn Ile
            340                 345                 350

Arg Arg Val Phe Asn Asp Cys Arg Asp Ile Ile Gln Arg Met His Leu
        355                 360                 365

Arg Gln Tyr Glu Leu Leu
    370

<210> SEQ ID NO 65
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 65

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125
```

```
Lys Arg Tyr Ala Ala Ala Met Gln Trp Leu Trp Arg Asp Ala Gly Ile
    130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Gly Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Ala Ser Gly Asp Gly Arg
                325                 330                 335

His Tyr Cys Tyr Pro His Phe Thr Cys Ala Val Asp Thr Glu Asn Ile
            340                 345                 350

Arg Arg Val Phe Gln Asp Cys Arg Asp Ile Ile Gln Arg Met His Leu
        355                 360                 365

Arg Gln Tyr Glu Leu Leu
    370

<210> SEQ ID NO 66
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 66

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
```

```
              100                 105                 110
Ala Ser Leu Val Met Ser Gln Asp Pro Tyr Lys Val Thr Thr Phe Glu
            115                 120                 125

Lys Arg Tyr Ala Ala Met Gln Trp Leu Trp Arg Asp Ala Gly Ile
130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Ala Ser Gly Asp Gly Arg
                325                 330                 335

His Tyr Cys Tyr Pro His Phe Thr Cys Ala Val Asp Thr Glu Asn Ile
                340                 345                 350

Arg Arg Val Phe Asp Asp Cys Arg Asp Ile Ile Gln Arg Met His Leu
            355                 360                 365

Arg Gln Tyr Glu Leu Leu
    370

<210> SEQ ID NO 67
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 67

Met Ala Arg Ser Leu Thr Trp Arg Cys Cys Pro Trp Cys Leu Thr Glu
1               5                   10                  15

Asp Glu Lys Ala Ala Arg Val Asp Gln Glu Ile Asn Arg Ile Leu
                20                  25                  30

Leu Glu Gln Lys Lys Gln Asp Arg Gly Glu Leu Lys Leu Leu Leu
            35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80
```

-continued

```
Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
            115                 120                 125

Lys Arg Tyr Ala Ala Met Gln Trp Leu Trp Arg Asp Ala Gly Ile
130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Ala Ser Gly Asp Gly Arg
                325                 330                 335

His Tyr Cys Tyr Pro His Phe Thr Cys Ala Val Asp Thr Glu Asn Ile
            340                 345                 350

Arg Arg Val Phe Glu Asp Cys Arg Asp Ile Ile Gln Arg Met His Leu
            355                 360                 365

Arg Gln Tyr Glu Leu Leu
    370
```

<210> SEQ ID NO 68
<211> LENGTH: 374
<212> TYPE: PRT
<213> ORGANISM: Artificial Sequence
<220> FEATURE:
<223> OTHER INFORMATION: Description of Artificial Sequence: G protein chimera

<400> SEQUENCE: 68

```
Met Ala Arg Ser Leu Thr Trp Arg Cys Cys Pro Trp Cys Leu Thr Glu
 1               5                  10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60
```

Ile His Gly Ala Gly Tyr Ser Glu Glu Arg Lys Gly Phe Arg Pro
65                  70                  75                  80

Leu Val Tyr Gln Asn Ile Phe Val Ser Met Arg Ala Met Ile Glu Ala
            85                  90                  95

Met Glu Arg Leu Gln Ile Pro Phe Ser Arg Pro Glu Ser Lys His His
        100                 105                 110

Ala Ser Leu Val Met Ser Gln Asp Pro Tyr Lys Val Thr Thr Phe Glu
        115                 120                 125

Lys Arg Tyr Ala Ala Met Gln Trp Leu Trp Arg Asp Ala Gly Ile
130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
        210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
        290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Ala Ser Gly Asp Gly Arg
                325                 330                 335

His Tyr Cys Tyr Pro His Phe Thr Cys Ala Val Asp Thr Glu Asn Ile
            340                 345                 350

Arg Arg Val Phe Asn Asp Cys Arg Asp Ile Ile Asn Arg Met His Leu
        355                 360                 365

Arg Gln Tyr Glu Leu Leu
    370

<210> SEQ ID NO 69
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 69

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu

```
                35                   40                    45
Gly Pro Gly Glu Ser Gly Lys Ser Thr Phe Ile Lys Gln Met Arg Ile
         50                   55                   60
Ile His Gly Ala Gly Tyr Ser Glu Glu Arg Lys Gly Phe Arg Pro
 65                   70                   75                   80
Leu Val Tyr Gln Asn Ile Phe Val Ser Met Arg Ala Met Ile Glu Ala
                 85                   90                   95
Met Glu Arg Leu Gln Ile Pro Phe Ser Arg Pro Glu Ser Lys His His
             100                 105                 110
Ala Ser Leu Val Met Ser Gln Asp Pro Tyr Lys Val Thr Thr Phe Glu
         115                 120                 125
Lys Arg Tyr Ala Ala Met Gln Trp Leu Trp Arg Asp Ala Gly Ile
130                 135                 140
Arg Ala Cys Tyr Glu Arg Arg Glu Phe His Leu Leu Asp Ser Ala
145                 150                 155                 160
Val Tyr Tyr Leu Ser His Leu Glu Arg Ile Thr Glu Glu Gly Tyr Val
                 165                 170                 175
Pro Thr Ala Gln Asp Val Leu Arg Ser Arg Met Pro Thr Gly Ile
             180                 185                 190
Asn Glu Tyr Cys Phe Ser Val Gln Lys Thr Asn Leu Arg Ile Val Asp
             195                 200                 205
Val Gly Gly Gln Lys Ser Glu Arg Lys Lys Trp Ile His Cys Phe Glu
210                 215                 220
Asn Val Ile Ala Leu Ile Tyr Leu Ala Ser Leu Ser Glu Tyr Asp Gln
225                 230                 235                 240
Cys Leu Glu Glu Asn Asn Gln Glu Asn Arg Met Lys Glu Ser Leu Ala
                 245                 250                 255
Leu Phe Gly Thr Ile Leu Glu Leu Pro Trp Phe Lys Ser Thr Ser Val
             260                 265                 270
Ile Leu Phe Leu Asn Lys Thr Asp Ile Leu Glu Glu Lys Ile Pro Thr
             275                 280                 285
Ser His Leu Ala Thr Tyr Phe Pro Ser Phe Gln Gly Pro Lys Gln Asp
         290                 295                 300
Ala Glu Ala Ala Lys Arg Phe Ile Leu Asp Met Tyr Thr Arg Met Tyr
305                 310                 315                 320
Thr Gly Cys Val Asp Gly Pro Glu Gly Ser Ala Ser Gly Asp Gly Arg
                 325                 330                 335
His Tyr Cys Tyr Pro His Phe Thr Cys Ala Val Asp Thr Glu Asn Ile
             340                 345                 350
Arg Arg Val Phe Asn Asp Cys Arg Asp Ile Ile Asp Arg Met His Leu
             355                 360                 365
Arg Gln Tyr Glu Leu Leu
    370

<210> SEQ ID NO 70
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 70

Met Ala Arg Ser Leu Thr Trp Arg Cys Cys Pro Trp Cys Leu Thr Glu
 1               5                  10                  15
```

```
Asp Glu Lys Ala Ala Arg Val Asp Gln Glu Ile Asn Arg Ile Leu
             20                  25                  30

Leu Glu Gln Lys Lys Gln Asp Arg Gly Glu Leu Lys Leu Leu Leu
         35                  40                  45

Gly Pro Gly Glu Ser Gly Lys Ser Thr Phe Ile Lys Gln Met Arg Ile
 50                  55                  60

Ile His Gly Ala Gly Tyr Ser Glu Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
             100                 105                 110

Ala Ser Leu Val Met Ser Gln Asp Pro Tyr Lys Val Thr Thr Phe Glu
         115                 120                 125

Lys Arg Tyr Ala Ala Met Gln Trp Leu Trp Arg Asp Ala Gly Ile
130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Gly Tyr Val
                 165                 170                 175

Pro Thr Ala Gln Asp Val Leu Arg Ser Arg Met Pro Thr Thr Gly Ile
             180                 185                 190

Asn Glu Tyr Cys Phe Ser Val Gln Lys Thr Asn Leu Arg Ile Val Asp
         195                 200                 205

Val Gly Gly Gln Lys Ser Glu Arg Lys Lys Trp Ile His Cys Phe Glu
     210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                 245                 250                 255

Leu Phe Gly Thr Ile Leu Glu Leu Pro Trp Phe Lys Ser Thr Ser Val
             260                 265                 270

Ile Leu Phe Leu Asn Lys Thr Asp Ile Leu Glu Glu Lys Ile Pro Thr
         275                 280                 285

Ser His Leu Ala Thr Tyr Phe Pro Ser Phe Gln Gly Pro Lys Gln Asp
     290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Ala Ser Gly Asp Gly Arg
                 325                 330                 335

His Tyr Cys Tyr Pro His Phe Thr Cys Ala Val Asp Thr Glu Asn Ile
             340                 345                 350

Arg Arg Val Phe Asn Asp Cys Arg Asp Ile Ile Glu Arg Met His Leu
         355                 360                 365

Arg Gln Tyr Glu Leu Leu
     370

<210> SEQ ID NO 71
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 71
```

-continued

```
Met Ala Arg Ser Leu Thr Trp Arg Cys Cys Pro Trp Cys Leu Thr Glu
 1               5                  10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Ala Ser Gly Asp Gly Arg
                325                 330                 335

His Tyr Cys Tyr Pro His Phe Thr Cys Ala Val Asp Thr Asp Asn Ile
            340                 345                 350

Arg Arg Val Phe Gln Asp Cys Arg Asp Ile Ile Gln Arg Met His Leu
        355                 360                 365

Arg Gln Tyr Glu Leu Leu
    370
```

<210> SEQ ID NO 72
<211> LENGTH: 374
<212> TYPE: PRT
<213> ORGANISM: Artificial Sequence
<220> FEATURE:

-continued

<223> OTHER INFORMATION: Description of Artificial Sequence: G protein chimera

<400> SEQUENCE: 72

```
Met Ala Arg Ser Leu Thr Trp Arg Cys Cys Pro Trp Cys Leu Thr Glu
 1               5                  10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
 50                  55                  60

Ile His Gly Ala Gly Tyr Ser Glu Glu Arg Lys Gly Phe Arg Pro
 65                  70                  75                  80

Leu Val Tyr Gln Asn Ile Phe Val Ser Met Arg Ala Met Ile Glu Ala
            85                  90                  95

Met Glu Arg Leu Gln Ile Pro Phe Ser Arg Pro Glu Ser Lys His His
        100                 105                 110

Ala Ser Leu Val Met Ser Gln Asp Pro Tyr Lys Val Thr Thr Phe Glu
    115                 120                 125

Lys Arg Tyr Ala Ala Ala Met Gln Trp Leu Trp Arg Asp Ala Gly Ile
130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Ala Ser Gly Asp Gly Arg
                325                 330                 335

His Tyr Cys Tyr Pro His Phe Thr Cys Ala Val Asp Thr Asp Asn Ile
            340                 345                 350

Arg Arg Val Phe Asp Asp Cys Arg Asp Ile Ile Gln Arg Met His Leu
        355                 360                 365

Arg Gln Tyr Glu Leu Leu
    370
```

<210> SEQ ID NO 73

-continued

```
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 73
```

Met Ala Arg Ser Leu Thr Trp Arg Cys Cys Pro Trp Cys Leu Thr Glu
 1               5                  10                  15

Asp Glu Lys Ala Ala Arg Val Asp Gln Glu Ile Asn Arg Ile Leu
             20                  25                  30

Leu Glu Gln Lys Lys Gln Asp Arg Gly Glu Leu Lys Leu Leu Leu
         35                  40                  45

Gly Pro Gly Glu Ser Gly Lys Ser Thr Phe Ile Lys Gln Met Arg Ile
 50                  55                  60

Ile His Gly Ala Gly Tyr Ser Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
             100                 105                 110

Ala Ser Leu Val Met Ser Gln Asp Pro Tyr Lys Val Thr Thr Phe Glu
             115                 120                 125

Lys Arg Tyr Ala Ala Ala Met Gln Trp Leu Trp Arg Asp Ala Gly Ile
 130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                 165                 170                 175

Pro Thr Ala Gln Asp Val Leu Arg Ser Arg Met Pro Thr Thr Gly Ile
             180                 185                 190

Asn Glu Tyr Cys Phe Ser Val Gln Lys Thr Asn Leu Arg Ile Val Asp
             195                 200                 205

Val Gly Gly Gln Lys Ser Glu Arg Lys Lys Trp Ile His Cys Phe Glu
 210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                 245                 250                 255

Leu Phe Gly Thr Ile Leu Glu Leu Pro Trp Phe Lys Ser Thr Ser Val
             260                 265                 270

Ile Leu Phe Leu Asn Lys Thr Asp Ile Leu Glu Glu Lys Ile Pro Thr
             275                 280                 285

Ser His Leu Ala Thr Tyr Phe Pro Ser Phe Gln Gly Pro Lys Gln Asp
         290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Ala Ser Gly Asp Gly Arg
                 325                 330                 335

His Tyr Cys Tyr Pro His Phe Cys Ala Val Asp Thr Asp Asn Ile
             340                 345                 350

Arg Arg Val Phe Glu Asp Cys Arg Asp Ile Ile Glu Arg Met His Leu
             355                 360                 365

Arg Gln Tyr Glu Leu Leu

370

<210> SEQ ID NO 74
<211> LENGTH: 374
<212> TYPE: PRT
<213> ORGANISM: Artificial Sequence
<220> FEATURE:
<223> OTHER INFORMATION: Description of Artificial Sequence: G protein chimera

<400> SEQUENCE: 74

Met Ala Arg Ser Leu Thr Trp Arg Cys Cys Pro Trp Cys Leu Thr Glu
 1               5                  10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Ala Ser Gly Asp Gly Arg
                325                 330                 335

His Tyr Cys Tyr Pro His Phe Thr Cys Ala Val Asp Thr Asp Asn Ile
            340                 345                 350

```
Arg Arg Val Phe Asn Asp Cys Arg Asp Ile Ile Asn Arg Met His Leu
        355                 360                 365

Arg Gln Tyr Glu Leu Leu
    370
```

<210> SEQ ID NO 75
<211> LENGTH: 374
<212> TYPE: PRT
<213> ORGANISM: Artificial Sequence
<220> FEATURE:
<223> OTHER INFORMATION: Description of Artificial Sequence: G protein chimera

<400> SEQUENCE: 75

```
Met Ala Arg Ser Leu Thr Trp Arg Cys Cys Pro Trp Cys Leu Thr Glu
  1               5                  10                  15

Asp Glu Lys Ala Ala Ala Arg Val Asp Gln Glu Ile Asn Arg Ile Leu
                 20                  25                  30

Leu Glu Gln Lys Lys Gln Asp Arg Gly Glu Leu Lys Leu Leu Leu Leu
             35                  40                  45

Gly Pro Gly Glu Ser Gly Lys Ser Thr Phe Ile Lys Gln Met Arg Ile
 50                  55                  60

Ile His Gly Ala Gly Tyr Ser Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Ala Ser Gly Asp Gly Arg
                325                 330                 335
```

His Tyr Cys Tyr Pro His Phe Thr Cys Ala Val Asp Thr Asp Asn Ile
            340                 345                 350

Arg Arg Val Phe Asn Asp Cys Arg Asp Ile Ile Asp Arg Met His Leu
        355                 360                 365

Arg Gln Tyr Glu Leu Leu
    370

<210> SEQ ID NO 76
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 76

Met Ala Arg Ser Leu Thr Trp Arg Cys Cys Pro Trp Cys Leu Thr Glu
  1               5                  10                  15

Asp Glu Lys Ala Ala Ala Arg Val Asp Gln Glu Ile Asn Arg Ile Leu
             20                  25                  30

Leu Glu Gln Lys Lys Gln Asp Arg Gly Glu Leu Lys Leu Leu Leu Leu
         35                  40                  45

Gly Pro Gly Glu Ser Gly Lys Ser Thr Phe Ile Lys Gln Met Arg Ile
     50                  55                  60

Ile His Gly Ala Gly Tyr Ser Glu Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr

```
                305                 310                 315                 320
Thr Gly Cys Val Asp Gly Pro Glu Gly Ser Ala Ser Gly Asp Gly Arg
                325                 330                 335

His Tyr Cys Tyr Pro His Phe Thr Cys Ala Val Asp Thr Asp Asn Ile
            340                 345                 350

Arg Arg Val Phe Asn Asp Cys Arg Asp Ile Ile Glu Arg Met His Leu
        355                 360                 365

Arg Gln Tyr Glu Leu Leu
    370

<210> SEQ ID NO 77
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 77

Met Ala Arg Ser Leu Thr Trp Arg Cys Cys Pro Trp Cys Leu Thr Glu
  1               5                  10                  15

Asp Glu Lys Ala Ala Ala Arg Val Asp Gln Glu Ile Asn Arg Ile Leu
                20                  25                  30

Leu Glu Gln Lys Lys Gln Asp Arg Gly Glu Leu Lys Leu Leu Leu Leu
            35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
                100                 105                 110

Ala Ser Leu Val Met Ser Gln Asp Pro Tyr Lys Val Thr Thr Phe Glu
            115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
    195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
    275                 280                 285
```

```
Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Ala Ser Gly Asp Gly Arg
                325                 330                 335

His Tyr Cys Tyr Pro His Phe Thr Cys Ala Val Asp Thr Glu Asn Ile
                340                 345                 350

Arg Arg Val Phe Gln Asp Cys Arg Asp Ile Ile Asn Arg Met His Leu
            355                 360                 365

Arg Gln Tyr Glu Leu Leu
        370

<210> SEQ ID NO 78
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 78

Met Ala Arg Ser Leu Thr Trp Arg Cys Cys Pro Trp Cys Leu Thr Glu
  1               5                  10                  15

Asp Glu Lys Ala Ala Ala Arg Val Asp Gln Glu Ile Asn Arg Ile Leu
                20                  25                  30

Leu Glu Gln Lys Lys Gln Asp Arg Gly Glu Leu Lys Leu Leu Leu Leu
            35                  40                  45

Gly Pro Gly Glu Ser Gly Lys Ser Thr Phe Ile Lys Gln Met Arg Ile
 50                  55                  60

Ile His Gly Ala Gly Tyr Ser Glu Glu Glu Arg Lys Gly Phe Arg Pro
 65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270
```

-continued

```
Ile Leu Phe Leu Asn Lys Thr Asp Ile Leu Glu Glu Lys Ile Pro Thr
            275                 280                 285
Ser His Leu Ala Thr Tyr Phe Pro Ser Phe Gln Gly Pro Lys Gln Asp
        290                 295                 300
Ala Glu Ala Ala Lys Arg Phe Ile Leu Asp Met Tyr Thr Arg Met Tyr
305                 310                 315                 320
Thr Gly Cys Val Asp Gly Pro Glu Gly Ser Ala Ser Gly Asp Gly Arg
                325                 330                 335
His Tyr Cys Tyr Pro His Phe Thr Cys Ala Val Asp Thr Glu Asn Ile
            340                 345                 350
Arg Arg Val Phe Gln Asp Cys Arg Asp Ile Ile Asp Arg Met His Leu
        355                 360                 365
Arg Gln Tyr Glu Leu Leu
    370

<210> SEQ ID NO 79
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 79

Met Ala Arg Ser Leu Thr Trp Arg Cys Cys Pro Trp Cys Leu Thr Glu
1               5                   10                  15
Asp Glu Lys Ala Ala Ala Arg Val Asp Gln Glu Ile Asn Arg Ile Leu
            20                  25                  30
Leu Glu Gln Lys Lys Gln Asp Arg Gly Glu Leu Lys Leu Leu Leu Leu
        35                  40                  45
Gly Pro Gly Glu Ser Gly Lys Ser Thr Phe Ile Lys Gln Met Arg Ile
    50                  55                  60
Ile His Gly Ala Gly Tyr Ser Glu Glu Glu Arg Lys Gly Phe Arg Pro
65                  70                  75                  80
Leu Val Tyr Gln Asn Ile Phe Val Ser Met Arg Ala Met Ile Glu Ala
                85                  90                  95
Met Glu Arg Leu Gln Ile Pro Phe Ser Arg Pro Glu Ser Lys His His
            100                 105                 110
Ala Ser Leu Val Met Ser Gln Asp Pro Tyr Lys Val Thr Thr Phe Glu
        115                 120                 125
Lys Arg Tyr Ala Ala Ala Met Gln Trp Leu Trp Arg Asp Ala Gly Ile
    130                 135                 140
Arg Ala Cys Tyr Glu Arg Arg Arg Glu Phe His Leu Leu Asp Ser Ala
145                 150                 155                 160
Val Tyr Tyr Leu Ser His Leu Glu Arg Ile Thr Glu Glu Gly Tyr Val
                165                 170                 175
Pro Thr Ala Gln Asp Val Leu Arg Ser Arg Met Pro Thr Thr Gly Ile
            180                 185                 190
Asn Glu Tyr Cys Phe Ser Val Gln Lys Thr Asn Leu Arg Ile Val Asp
        195                 200                 205
Val Gly Gly Gln Lys Ser Glu Arg Lys Lys Trp Ile His Cys Phe Glu
    210                 215                 220
Asn Val Ile Ala Leu Ile Tyr Leu Ala Ser Leu Ser Glu Tyr Asp Gln
225                 230                 235                 240
Cys Leu Glu Glu Asn Asn Gln Glu Asn Arg Met Lys Glu Ser Leu Ala
```

```
                         245                 250                     255
Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
            290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Ala Ser Gly Asp Gly Arg
                325                 330                 335

His Tyr Cys Tyr Pro His Phe Thr Cys Ala Val Asp Thr Glu Asn Ile
                340                 345                 350

Arg Arg Val Phe Gln Asp Cys Arg Asp Ile Ile Glu Arg Met His Leu
                355                 360                 365

Arg Gln Tyr Glu Leu Leu
            370

<210> SEQ ID NO 80
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 80

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
    210                 215                 220
```

```
Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
                260                 265                 270

Ile Leu Phe Leu Asn Lys Thr Asp Ile Leu Glu Glu Lys Ile Pro Thr
                275                 280                 285

Ser His Leu Ala Thr Tyr Phe Pro Ser Phe Gln Gly Pro Lys Gln Asp
                290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Ala Ser Gly Asp Gly Arg
                325                 330                 335

His Tyr Cys Tyr Pro His Phe Thr Cys Ala Val Asp Thr Glu Asn Ile
                340                 345                 350

Arg Arg Val Phe Asp Asp Cys Arg Asp Ile Ile Asn Arg Met His Leu
                355                 360                 365

Arg Gln Tyr Glu Leu Leu
        370

<210> SEQ ID NO 81
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 81

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
                20                  25                  30

Leu Glu Gln Lys Lys Gln Asp Arg Gly Glu Leu Lys Leu Leu Leu Leu
            35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
                100                 105                 110

Ala Ser Leu Val Met Ser Gln Asp Pro Tyr Lys Val Thr Thr Phe Glu
            115                 120                 125

Lys Arg Tyr Ala Ala Ala Met Gln Trp Leu Trp Arg Asp Ala Gly Ile
130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205
```

```
Val Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Ala Ser Gly Asp Gly Arg
                325                 330                 335

His Tyr Cys Tyr Pro His Phe Thr Cys Ala Val Asp Thr Glu Asn Ile
            340                 345                 350

Arg Arg Val Phe Asp Asp Cys Arg Asp Ile Ile Asp Arg Met His Leu
            355                 360                 365

Arg Gln Tyr Glu Leu Leu
    370

<210> SEQ ID NO 82
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 82

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
                20                  25                  30

Leu Glu Gln Lys Lys Gln Asp Arg Gly Glu Leu Lys Leu Leu Leu Leu
            35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
```

-continued

```
                180                 185                 190
Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Ala Ser Gly Asp Gly Arg
                325                 330                 335

His Tyr Cys Tyr Pro His Phe Thr Cys Ala Val Asp Thr Glu Asn Ile
            340                 345                 350

Arg Arg Val Phe Asp Asp Cys Arg Asp Ile Ile Glu Arg Met His Leu
        355                 360                 365

Arg Gln Tyr Glu Leu Leu
    370

<210> SEQ ID NO 83
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 83

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160
```

```
Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
                260                 265                 270

Ile Leu Phe Leu Asn Lys Thr Asp Ile Leu Glu Glu Lys Ile Pro Thr
                275                 280                 285

Ser His Leu Ala Thr Tyr Phe Pro Ser Phe Gln Gly Pro Lys Gln Asp
                290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Ala Ser Gly Asp Gly Arg
                325                 330                 335

His Tyr Cys Tyr Pro His Phe Thr Cys Ala Val Asp Thr Glu Asn Ile
                340                 345                 350

Arg Arg Val Phe Glu Asp Cys Arg Asp Ile Ile Asn Arg Met His Leu
                355                 360                 365

Arg Gln Tyr Glu Leu Leu
        370

<210> SEQ ID NO 84
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 84

Met Ala Arg Ser Leu Thr Trp Arg Cys Cys Pro Trp Cys Leu Thr Glu
  1               5                  10                  15

Asp Glu Lys Ala Ala Ala Arg Val Asp Gln Glu Ile Asn Arg Ile Leu
                20                  25                  30

Leu Glu Gln Lys Lys Gln Asp Arg Gly Glu Leu Lys Leu Leu Leu Leu
            35                  40                  45

Gly Pro Gly Glu Ser Gly Lys Ser Thr Phe Ile Lys Gln Met Arg Ile
     50                  55                  60

Ile His Gly Ala Gly Tyr Ser Glu Glu Glu Arg Lys Gly Phe Arg Pro
 65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140
```

```
Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
            165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
        210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Ala Ser Gly Asp Gly Arg
                325                 330                 335

His Tyr Cys Tyr Pro His Phe Thr Cys Ala Val Asp Thr Glu Asn Ile
                340                 345                 350

Arg Arg Val Phe Glu Asp Cys Arg Asp Ile Ile Asp Arg Met His Leu
            355                 360                 365

Arg Gln Tyr Glu Leu Leu
    370

<210> SEQ ID NO 85
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 85

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
```

-continued

```
                115                 120                 125
Lys Arg Tyr Ala Ala Ala Met Gln Trp Leu Trp Arg Asp Ala Gly Ile
        130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Ala Ser Gly Asp Gly Arg
                325                 330                 335

His Tyr Cys Tyr Pro His Phe Thr Cys Ala Val Asp Thr Glu Asn Ile
            340                 345                 350

Arg Arg Val Phe Glu Asp Cys Arg Asp Ile Ile Glu Arg Met His Leu
        355                 360                 365

Arg Gln Tyr Glu Leu Leu
    370

<210> SEQ ID NO 86
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 86

Met Ala Arg Ser Leu Thr Trp Arg Cys Cys Pro Trp Cys Leu Thr Glu
1               5                   10                  15

Asp Glu Lys Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95
```

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
            115                 120                 125

Lys Arg Tyr Ala Ala Ala Met Gln Trp Leu Trp Arg Asp Ala Gly Ile
            130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
            210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
            290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Ala Ser Gly Asp Gly Arg
                325                 330                 335

His Tyr Cys Tyr Pro His Phe Thr Cys Ala Val Asp Thr Asp Asn Ile
            340                 345                 350

Arg Arg Val Phe Gln Asp Cys Arg Asp Ile Ile Asn Arg Met His Leu
            355                 360                 365

Arg Gln Tyr Glu Leu Leu
        370

<210> SEQ ID NO 87
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 87

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

-continued

```
Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
            115                 120                 125

Lys Arg Tyr Ala Ala Met Gln Trp Leu Trp Arg Asp Ala Gly Ile
    130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Ala Ser Gly Asp Gly Arg
                325                 330                 335

His Tyr Cys Tyr Pro His Phe Thr Cys Ala Val Asp Thr Asp Asn Ile
            340                 345                 350

Arg Arg Val Phe Asp Asp Cys Arg Asp Ile Ile Asn Arg Met His Leu
        355                 360                 365

Arg Gln Tyr Glu Leu Leu
    370

<210> SEQ ID NO 88
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 88

Met Ala Arg Ser Leu Thr Trp Arg Cys Cys Pro Trp Cys Leu Thr Glu
  1               5                  10                  15

Asp Glu Lys Ala Ala Ala Arg Val Asp Gln Glu Ile Asn Arg Ile Leu
             20                  25                  30

Leu Glu Gln Lys Lys Gln Asp Arg Gly Glu Leu Lys Leu Leu Leu Leu
         35                  40                  45

Gly Pro Gly Glu Ser Gly Lys Ser Thr Phe Ile Lys Gln Met Arg Ile
```

```
        50                  55                  60
Ile His Gly Ala Gly Tyr Ser Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
                100                 105                 110

Ala Ser Leu Val Met Ser Gln Asp Pro Tyr Lys Val Thr Thr Phe Glu
                115                 120                 125

Lys Arg Tyr Ala Ala Met Gln Trp Leu Trp Arg Asp Ala Gly Ile
                130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
                180                 185                 190

Asn Glu Tyr Cys Phe Ser Val Gln Lys Thr Asn Leu Arg Ile Val Asp
                195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
                260                 265                 270

Ile Leu Phe Leu Asn Lys Thr Asp Ile Leu Glu Glu Lys Ile Pro Thr
                275                 280                 285

Ser His Leu Ala Thr Tyr Phe Pro Ser Phe Gln Gly Pro Lys Gln Asp
                290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Ala Ser Gly Asp Gly Arg
                325                 330                 335

His Tyr Cys Tyr Pro His Phe Thr Cys Ala Val Asp Thr Asp Asn Ile
                340                 345                 350

Arg Arg Val Phe Glu Asp Cys Arg Asp Ile Ile Asn Arg Met His Leu
                355                 360                 365

Arg Gln Tyr Glu Leu Leu
        370

<210> SEQ ID NO 89
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 89

Met Ala Arg Ser Leu Thr Trp Arg Cys Cys Pro Trp Cys Leu Thr Glu
  1               5                  10                  15

Asp Glu Lys Ala Ala Ala Arg Val Asp Gln Glu Ile Asn Arg Ile Leu
                 20                  25                  30
```

-continued

```
Leu Glu Gln Lys Lys Gln Asp Arg Gly Glu Leu Lys Leu Leu Leu
            35                  40                  45
Gly Pro Gly Glu Ser Gly Lys Ser Thr Phe Ile Lys Gln Met Arg Ile
 50                  55                  60
Ile His Gly Ala Gly Tyr Ser Glu Glu Arg Lys Gly Phe Arg Pro
 65                  70                  75                  80
Leu Val Tyr Gln Asn Ile Phe Val Ser Met Arg Ala Met Ile Glu Ala
                 85                  90                  95
Met Glu Arg Leu Gln Ile Pro Phe Ser Arg Pro Glu Ser Lys His His
                100                 105                 110
Ala Ser Leu Val Met Ser Gln Asp Pro Tyr Lys Val Thr Thr Phe Glu
            115                 120                 125
Lys Arg Tyr Ala Ala Met Gln Trp Leu Trp Arg Asp Ala Gly Ile
130                 135                 140
Arg Ala Cys Tyr Glu Arg Arg Arg Glu Phe His Leu Leu Asp Ser Ala
145                 150                 155                 160
Val Tyr Tyr Leu Ser His Leu Glu Arg Ile Thr Glu Glu Gly Tyr Val
                165                 170                 175
Pro Thr Ala Gln Asp Val Leu Arg Ser Arg Met Pro Thr Thr Gly Ile
            180                 185                 190
Asn Glu Tyr Cys Phe Ser Val Gln Lys Thr Asn Leu Arg Ile Val Asp
            195                 200                 205
Val Gly Gly Gln Lys Ser Glu Arg Lys Lys Trp Ile His Cys Phe Glu
210                 215                 220
Asn Val Ile Ala Leu Ile Tyr Leu Ala Ser Leu Ser Glu Tyr Asp Gln
225                 230                 235                 240
Cys Leu Glu Glu Asn Asn Gln Glu Asn Arg Met Lys Glu Ser Leu Ala
                245                 250                 255
Leu Phe Gly Thr Ile Leu Glu Leu Pro Trp Phe Lys Ser Thr Ser Val
            260                 265                 270
Ile Leu Phe Leu Asn Lys Thr Asp Ile Leu Glu Glu Lys Ile Pro Thr
            275                 280                 285
Ser His Leu Ala Thr Tyr Phe Pro Ser Phe Gln Gly Pro Lys Gln Asp
    290                 295                 300
Ala Glu Ala Ala Lys Arg Phe Ile Leu Asp Met Tyr Thr Arg Met Tyr
305                 310                 315                 320
Thr Gly Cys Val Asp Gly Pro Glu Gly Ser Ala Ser Gly Asp Gly Arg
                325                 330                 335
His Tyr Cys Tyr Pro His Phe Thr Cys Ala Val Asp Thr Asp Asn Ile
            340                 345                 350
Arg Arg Val Phe Asp Asp Cys Arg Asp Ile Ile Asp Arg Met His Leu
            355                 360                 365
Arg Gln Tyr Glu Leu Leu
    370

<210> SEQ ID NO 90
<211> LENGTH: 374
<212> TYPE: PRT
<213> ORGANISM: Artificial Sequence
<220> FEATURE:
<223> OTHER INFORMATION: Description of Artificial Sequence: G protein
      chimera

<400> SEQUENCE: 90

Met Ala Arg Ser Leu Thr Trp Arg Cys Cys Pro Trp Cys Leu Thr Glu
  1               5                  10                  15
```

```
Asp Glu Lys Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu
            35                  40                  45

Gly Pro Gly Glu Ser Gly Lys Ser Thr Phe Ile Lys Gln Met Arg Ile
            50                  55                  60

Ile His Gly Ala Gly Tyr Ser Glu Glu Arg Lys Gly Phe Arg Pro
 65                  70                  75                  80

Leu Val Tyr Gln Asn Ile Phe Val Ser Met Arg Ala Met Ile Glu Ala
                    85                  90                  95

Met Glu Arg Leu Gln Ile Pro Phe Ser Arg Pro Glu Ser Lys His His
                100                 105                 110

Ala Ser Leu Val Met Ser Gln Asp Pro Tyr Lys Val Thr Thr Phe Glu
            115                 120                 125

Lys Arg Tyr Ala Ala Met Gln Trp Leu Trp Arg Asp Ala Gly Ile
            130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
            290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Ala Ser Gly Asp Gly Arg
            325                 330                 335

His Tyr Cys Tyr Pro His Phe Thr Cys Ala Val Asp Thr Asp Asn Ile
            340                 345                 350

Arg Arg Val Phe Asp Asp Cys Arg Asp Ile Ile Glu Arg Met His Leu
            355                 360                 365

Arg Gln Tyr Glu Leu Leu
            370
```

<210> SEQ ID NO 91
<211> LENGTH: 374
<212> TYPE: PRT
<213> ORGANISM: Artificial Sequence
<220> FEATURE:
<223> OTHER INFORMATION: Description of Artificial Sequence: G protein chimera

```
<400> SEQUENCE: 91

Met Ala Arg Ser Leu Thr Trp Arg Cys Cys Pro Trp Cys Leu Thr Glu
 1               5                  10                  15

Asp Glu Lys Ala Ala Arg Val Asp Gln Glu Ile Asn Arg Ile Leu
             20                  25                  30

Leu Glu Gln Lys Lys Gln Asp Arg Gly Glu Leu Lys Leu Leu Leu
         35                  40                  45

Gly Pro Gly Glu Ser Gly Lys Ser Thr Phe Ile Lys Gln Met Arg Ile
 50                  55                  60

Ile His Gly Ala Gly Tyr Ser Glu Glu Arg Lys Gly Phe Arg Pro
 65                  70                  75                  80

Leu Val Tyr Gln Asn Ile Phe Val Ser Met Arg Ala Met Ile Glu Ala
                 85                  90                  95

Met Glu Arg Leu Gln Ile Pro Phe Ser Arg Pro Glu Ser Lys His His
             100                 105                 110

Ala Ser Leu Val Met Ser Gln Asp Pro Tyr Lys Val Thr Thr Phe Glu
         115                 120                 125

Lys Arg Tyr Ala Ala Met Gln Trp Leu Trp Arg Asp Ala Gly Ile
130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
                 165                 170                 175

Pro Thr Ala Gln Asp Val Leu Arg Ser Arg Met Pro Thr Thr Gly Ile
             180                 185                 190

Asn Glu Tyr Cys Phe Ser Val Gln Lys Thr Asn Leu Arg Ile Val Asp
         195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                 245                 250                 255

Leu Phe Gly Thr Ile Leu Glu Leu Pro Trp Phe Lys Ser Thr Ser Val
             260                 265                 270

Ile Leu Phe Leu Asn Lys Thr Asp Ile Leu Glu Glu Lys Ile Pro Thr
         275                 280                 285

Ser His Leu Ala Thr Tyr Phe Pro Ser Phe Gln Gly Pro Lys Gln Asp
290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Ala Ser Gly Asp Gly Arg
                 325                 330                 335

His Tyr Cys Tyr Pro His Phe Thr Cys Ala Val Asp Thr Asp Asn Ile
             340                 345                 350

Arg Arg Val Phe Glu Asp Cys Arg Asp Ile Ile Asp Arg Met His Leu
         355                 360                 365

Arg Gln Tyr Glu Leu Leu
         370

<210> SEQ ID NO 92
<211> LENGTH: 374
<212> TYPE: PRT
<213> ORGANISM: Artificial Sequence
```

<220> FEATURE:
<223> OTHER INFORMATION: Description of Artificial Sequence: G protein
      chimera

<400> SEQUENCE: 92

```
Met Ala Arg Ser Leu Thr Trp Arg Cys Cys Pro Trp Cys Leu Thr Glu
  1               5                  10                  15

Asp Glu Lys Ala Ala Arg Val Asp Gln Glu Ile Asn Arg Ile Leu
             20                  25                  30

Leu Glu Gln Lys Lys Gln Asp Arg Gly Glu Leu Lys Leu Leu Leu
         35                  40                  45

Gly Pro Gly Glu Ser Gly Lys Ser Thr Phe Ile Lys Gln Met Arg Ile
 50                  55                  60

Ile His Gly Ala Gly Tyr Ser Glu Glu Arg Lys Gly Phe Arg Pro
 65              70                  75                  80

Leu Val Tyr Gln Asn Ile Phe Val Ser Met Arg Ala Met Ile Glu Ala
             85                  90                  95

Met Glu Arg Leu Gln Ile Pro Phe Ser Arg Pro Glu Ser Lys His His
             100                 105                 110

Ala Ser Leu Val Met Ser Gln Asp Pro Tyr Lys Val Thr Thr Phe Glu
         115                 120                 125

Lys Arg Tyr Ala Ala Met Gln Trp Leu Trp Arg Asp Ala Gly Ile
 130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
             165                 170                 175

Pro Thr Ala Gln Asp Val Leu Arg Ser Arg Met Pro Thr Thr Gly Ile
         180                 185                 190

Asn Glu Tyr Cys Phe Ser Val Gln Lys Thr Asn Leu Arg Ile Val Asp
     195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
             245                 250                 255

Leu Phe Gly Thr Ile Leu Glu Leu Pro Trp Phe Lys Ser Thr Ser Val
         260                 265                 270

Ile Leu Phe Leu Asn Lys Thr Asp Ile Leu Glu Glu Lys Ile Pro Thr
     275                 280                 285

Ser His Leu Ala Thr Tyr Phe Pro Ser Phe Gln Gly Pro Lys Gln Asp
         290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Ala Ser Gly Asp Gly Arg
                 325                 330                 335

His Tyr Cys Tyr Pro His Phe Thr Cys Ala Val Asp Thr Asp Asn Ile
             340                 345                 350

Arg Arg Val Phe Glu Asp Cys Arg Asp Ile Ile Glu Arg Met His Leu
         355                 360                 365

Arg Gln Tyr Glu Leu Leu
 370
```

```
<210> SEQ ID NO 93
<211> LENGTH: 33
<212> TYPE: DNA
<213> ORGANISM: Artificial Sequence
<220> FEATURE:
<223> OTHER INFORMATION: Description of Artificial Sequence: PCR primer

<400> SEQUENCE: 93
cactacacat gtgccacaga caccagtaac atc                              33

<210> SEQ ID NO 94
<211> LENGTH: 33
<212> TYPE: DNA
<213> ORGANISM: Artificial Sequence
<220> FEATURE:
<223> OTHER INFORMATION: Description of Artificial Sequence: PCR primer

<400> SEQUENCE: 94
gatgttactg gtgtctgtgg cacatgtgta gtg                              33

<210> SEQ ID NO 95
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 95
ggccccgagg gcagcaaccg aaacaaggag                                  30

<210> SEQ ID NO 96
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 96
ctccttgttt cggttgctgc cctcggggcc                                  30

<210> SEQ ID NO 97
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 97
gctacctatt tccccgagta caagggtcag                                  30

<210> SEQ ID NO 98
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 98
ctgacccttg tactcgggga aataggtagc                                  30

<210> SEQ ID NO 99
<211> LENGTH: 30
<212> TYPE: DNA
<213> ORGANISM: Artificial Sequence
<220> FEATURE:
<223> OTHER INFORMATION: Description of Artificial Sequence: PCR primer
```

<400> SEQUENCE: 99
gagagccagc ggcagcgcgg ggagctgaag    30

<210> SEQ ID NO 100
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 100
cttcagctcc ccgcgctgcc gctggctctc    30

<210> SEQ ID NO 101
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 101
tacacatgtg ccacagacac tgagaacatc    30

<210> SEQ ID NO 102
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 102
gatgttctca gtgtctgtgg cacatgtgta    30

<210> SEQ ID NO 103
<211> LENGTH: 27
<212> TYPE: DNA
<213> ORGANISM: Artificial Sequence
<220> FEATURE:
<223> OTHER INFORMATION: Description of Artificial Sequence: PCR primer

<400> SEQUENCE: 103
ggccccgagg gcagcgctag tggagat    27

<210> SEQ ID NO 104
<211> LENGTH: 27
<212> TYPE: DNA
<213> ORGANISM: Artificial Sequence
<220> FEATURE:
<223> OTHER INFORMATION: Description of Artificial Sequence: PCR primer

<400> SEQUENCE: 104
atctccacta gcgctgccct cggggcc    27

<210> SEQ ID NO 105
<211> LENGTH: 374
<212> TYPE: PRT
<213> ORGANISM: Homo sapiens

<400> SEQUENCE: 105

Met Ala Arg Ser Leu Thr Trp Arg Cys Cys Pro Trp Cys Leu Thr Glu
1               5                  10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu

```
            35                  40                  45
Gly Pro Gly Glu Ser Gly Lys Ser Thr Phe Ile Lys Gln Met Arg Ile
 50                  55                  60
Ile His Gly Ala Gly Tyr Ser Glu Glu Arg Lys Gly Phe Arg Pro
 65                  70                  75                  80
Leu Val Tyr Gln Asn Ile Phe Val Ser Met Arg Ala Met Ile Glu Ala
                 85                  90                  95
Met Glu Arg Leu Gln Ile Pro Phe Ser Arg Pro Glu Ser Lys His His
             100                 105                 110
Ala Ser Leu Val Met Ser Gln Asp Pro Tyr Lys Val Thr Thr Phe Glu
             115                 120                 125
Lys Arg Tyr Ala Ala Met Gln Trp Leu Trp Arg Asp Ala Gly Ile
130                 135                 140
Arg Ala Cys Tyr Glu Arg Arg Glu Phe His Leu Leu Asp Ser Ala
145                 150                 155                 160
Val Tyr Tyr Leu Ser His Leu Glu Arg Ile Thr Glu Glu Gly Tyr Val
                 165                 170                 175
Pro Thr Ala Gln Asp Val Leu Arg Ser Arg Met Pro Thr Thr Gly Ile
             180                 185                 190
Asn Glu Tyr Cys Phe Ser Val Gln Lys Thr Asn Leu Arg Ile Val Asp
             195                 200                 205
Val Gly Gly Gln Lys Ser Glu Arg Lys Lys Trp Ile His Cys Phe Glu
210                 215                 220
Asn Val Ile Ala Leu Ile Tyr Leu Ala Ser Leu Ser Glu Tyr Asp Gln
225                 230                 235                 240
Cys Leu Glu Glu Asn Asn Gln Glu Asn Arg Met Lys Glu Ser Leu Ala
             245                 250                 255
Leu Phe Gly Thr Ile Leu Glu Leu Pro Trp Phe Lys Ser Thr Ser Val
             260                 265                 270
Ile Leu Phe Leu Asn Lys Thr Asp Ile Leu Glu Glu Lys Ile Pro Thr
             275                 280                 285
Ser His Leu Ala Thr Tyr Phe Pro Ser Phe Gln Gly Pro Lys Gln Asp
             290                 295                 300
Ala Glu Ala Ala Lys Arg Phe Ile Leu Asp Met Tyr Thr Arg Met Tyr
305                 310                 315                 320
Thr Gly Cys Val Asp Gly Pro Glu Gly Ser Lys Lys Gly Ala Arg Ser
                 325                 330                 335
Arg Arg Leu Phe Ser His Tyr Thr Cys Ala Thr Asp Thr Gln Asn Ile
             340                 345                 350
Arg Lys Val Phe Lys Asp Val Arg Asp Ser Val Leu Ala Arg Tyr Leu
             355                 360                 365
Asp Glu Ile Asn Leu Leu
    370

<210> SEQ ID NO 106
<211> LENGTH: 394
<212> TYPE: PRT
<213> ORGANISM: Rattus sp.

<400> SEQUENCE: 106

Met Gly Cys Leu Gly Asn Ser Lys Thr Glu Asp Gln Arg Asn Glu Glu
 1               5                  10                  15
Lys Ala Gln Arg Glu Ala Asn Lys Lys Ile Glu Lys Gln Leu Gln Lys
             20                  25                  30
```

```
Asp Lys Gln Val Tyr Arg Ala Thr His Arg Leu Leu Leu Leu Gly Ala
         35                  40                  45

Gly Glu Ser Gly Lys Ser Thr Ile Val Lys Gln Met Arg Ile Leu His
     50                  55                  60

Val Asn Gly Phe Asn Gly Glu Gly Gly Glu Glu Asp Pro Gln Ala Ala
 65                  70                  75                  80

Arg Ser Asn Ser Asp Gly Glu Lys Ala Thr Lys Val Gln Asp Ile Lys
                 85                  90                  95

Asn Asn Leu Lys Glu Ala Ile Glu Thr Ile Val Ala Ala Met Ser Asn
             100                 105                 110

Leu Val Pro Pro Val Glu Leu Ala Asn Pro Glu Asn Gln Phe Arg Val
         115                 120                 125

Asp Tyr Ile Leu Ser Val Met Asn Val Pro Asn Phe Asp Phe Pro Pro
130                 135                 140

Glu Phe Tyr Glu His Ala Lys Ala Leu Trp Glu Asp Glu Gly Val Arg
145                 150                 155                 160

Ala Cys Tyr Glu Arg Ser Asn Glu Tyr Gln Leu Ile Asp Cys Ala Gln
                165                 170                 175

Tyr Phe Leu Asp Lys Ile Asp Val Ile Lys Gln Ala Asp Tyr Val Pro
             180                 185                 190

Ser Asp Gln Asp Leu Leu Arg Cys Arg Val Leu Thr Ser Gly Ile Phe
         195                 200                 205

Glu Thr Lys Phe Gln Val Asp Lys Val Asn Phe His Met Phe Asp Val
210                 215                 220

Gly Gly Gln Arg Asp Glu Arg Arg Lys Trp Ile Gln Cys Phe Asn Asp
225                 230                 235                 240

Val Thr Ala Ile Ile Phe Val Val Ala Ser Ser Tyr Asn Met Val
                245                 250                 255

Ile Arg Glu Asp Asn Gln Thr Asn Arg Leu Gln Glu Ala Leu Asn Leu
             260                 265                 270

Phe Lys Ser Ile Trp Asn Asn Arg Trp Leu Arg Thr Ile Ser Val Ile
         275                 280                 285

Leu Phe Leu Asn Lys Gln Asp Leu Leu Ala Glu Lys Val Leu Ala Gly
290                 295                 300

Lys Ser Lys Ile Glu Asp Tyr Phe Pro Glu Phe Ala Arg Tyr Thr Thr
305                 310                 315                 320

Pro Glu Asp Ala Thr Pro Glu Pro Gly Glu Asp Pro Arg Val Thr Arg
                325                 330                 335

Ala Lys Tyr Phe Ile Arg Asp Glu Phe Leu Arg Ile Ser Thr Ala Ser
             340                 345                 350

Gly Asp Gly Arg His Tyr Cys Tyr Pro His Phe Thr Cys Ala Val Asp
         355                 360                 365

Thr Glu Asn Ile Arg Arg Val Phe Asn Asp Cys Arg Asp Ile Ile Gln
370                 375                 380

Arg Met His Leu Arg Gln Tyr Glu Leu Leu
385                 390

<210> SEQ ID NO 107
<211> LENGTH: 355
<212> TYPE: PRT
<213> ORGANISM: Mus sp.

<400> SEQUENCE: 107

Met Gly Cys Arg Gln Ser Ser Glu Glu Lys Glu Ala Ala Arg Arg Ser
 1               5                  10                  15
```

```
Arg Arg Ile Asp Arg His Leu Arg Ser Glu Ser Gln Arg Gln Arg Arg
             20                  25                  30

Glu Ile Lys Leu Leu Leu Gly Thr Ser Asn Ser Gly Lys Ser Thr
         35                  40                  45

Ile Val Lys Gln Met Lys Ile Ile His Ser Gly Gly Phe Asn Leu Glu
     50                  55                  60

Ala Cys Lys Glu Tyr Lys Pro Leu Ile Ile Tyr Asn Ala Ile Asp Ser
 65              70                  75                      80

Leu Thr Arg Ile Ile Arg Ala Leu Ala Ala Leu Arg Ile Asp Phe His
                 85                  90                  95

Asn Pro Asp Arg Ala Tyr Asp Ala Val Gln Leu Phe Ala Leu Thr Gly
             100                 105                 110

Pro Ala Glu Ser Lys Gly Glu Ile Thr Pro Glu Leu Leu Gly Val Met
         115                 120                 125

Arg Arg Leu Trp Ala Asp Pro Gly Ala Gln Ala Cys Phe Ser Arg Ser
     130                 135                 140

Ser Glu Tyr His Leu Glu Asp Asn Ala Ala Tyr Tyr Leu Asn Asp Leu
145                 150                 155                 160

Glu Arg Ile Ala Ala Asp Tyr Ile Pro Thr Val Glu Asp Ile Leu
                 165                 170                 175

Arg Ser Arg Asp Met Thr Thr Gly Ile Val Glu Asn Lys Phe Thr Phe
             180                 185                 190

Lys Glu Leu Thr Phe Lys Met Val Asp Val Gly Gln Arg Ser Glu
         195                 200                 205

Arg Lys Lys Trp Ile His Cys Phe Glu Gly Val Thr Ala Ile Ile Phe
     210                 215                 220

Cys Val Glu Leu Ser Gly Tyr Asp Leu Lys Leu Tyr Glu Asp Asn Gln
225                 230                 235                 240

Thr Ser Arg Met Ala Glu Ser Leu Arg Leu Phe Asp Ser Ile Cys Asn
             245                 250                 255

Asn Asn Trp Phe Ile Asn Thr Ser Leu Ile Leu Phe Leu Asn Lys Lys
             260                 265                 270

Asp Leu Leu Ala Glu Lys Ile Arg Arg Ile Pro Leu Thr Ile Cys Phe
         275                 280                 285

Pro Glu Tyr Lys Gly Gln Asn Thr Tyr Glu Glu Ala Ala Val Tyr Ile
     290                 295                 300

Gln Arg Gln Phe Glu Asp Leu Asn Arg Asn Lys Glu Thr Lys Glu Ile
305                 310                 315                 320

Tyr Ser His Phe Thr Cys Ala Thr Asp Thr Ser Asn Ile Gln Phe Val
             325                 330                 335

Phe Asp Ala Val Thr Asp Val Ile Ile Gln Asn Asn Leu Lys Tyr Ile
             340                 345                 350

Gly Leu Cys
        355

<210> SEQ ID NO 108
<211> LENGTH: 365
<212> TYPE: PRT
<213> ORGANISM: Artificial Sequence
<220> FEATURE:
<223> OTHER INFORMATION: Description of Artificial Sequence: G protein
      chimera

<400> SEQUENCE: 108

Met Gly Cys Arg Gln Ser Ser Glu Glu Lys Glu Ala Ala Arg Arg Ser
```

```
            1               5                   10                  15
Arg Arg Ile Asp Arg His Leu Arg Ser Glu Ser Gln Arg Gln Arg Arg
                20                  25                  30

Glu Ile Lys Leu Leu Leu Gly Pro Gly Glu Ser Gly Lys Ser Thr
            35                  40                  45

Phe Ile Lys Gln Met Arg Ile Ile His Gly Ala Gly Tyr Ser Glu Glu
            50                  55                  60

Glu Arg Lys Gly Phe Arg Pro Leu Val Tyr Gln Asn Ile Phe Val Ser
65                      70                  75                  80

Met Arg Ala Met Ile Glu Ala Met Glu Arg Leu Gln Ile Pro Phe Ser
                    85                  90                  95

Arg Pro Glu Ser Lys His His Ala Ser Leu Val Met Ser Gln Asp Pro
                100                 105                 110

Tyr Lys Val Thr Thr Phe Glu Lys Arg Tyr Ala Ala Ala Met Gln Trp
            115                 120                 125

Leu Trp Arg Asp Ala Gly Ile Arg Ala Cys Tyr Glu Arg Arg Arg Glu
130                 135                 140

Phe His Leu Leu Asp Ser Ala Val Tyr Tyr Leu Ser His Leu Glu Arg
145                 150                 155                 160

Ile Thr Glu Glu Gly Tyr Val Pro Thr Ala Gln Asp Val Leu Arg Ser
                165                 170                 175

Arg Met Pro Thr Thr Gly Ile Asn Glu Tyr Cys Phe Ser Val Gln Lys
                180                 185                 190

Thr Asn Leu Arg Ile Val Asp Val Gly Gly Gln Lys Ser Glu Arg Lys
            195                 200                 205

Lys Trp Ile His Cys Phe Glu Asn Val Ile Ala Leu Ile Tyr Leu Ala
            210                 215                 220

Ser Leu Ser Glu Tyr Asp Gln Cys Leu Glu Glu Asn Asn Gln Glu Asn
225                 230                 235                 240

Arg Met Lys Glu Ser Leu Ala Leu Phe Gly Thr Ile Leu Glu Leu Pro
                245                 250                 255

Trp Phe Lys Ser Thr Ser Val Ile Leu Phe Leu Asn Lys Thr Asp Ile
                260                 265                 270

Leu Glu Glu Lys Ile Pro Thr Ser His Leu Ala Thr Tyr Phe Pro Ser
            275                 280                 285

Phe Gln Gly Pro Lys Gln Asp Ala Glu Ala Ala Lys Arg Phe Ile Leu
            290                 295                 300

Asp Met Tyr Thr Arg Met Tyr Thr Gly Cys Val Asp Gly Pro Glu Gly
305                 310                 315                 320

Ser Lys Lys Gly Ala Arg Ser Arg Arg Leu Phe Ser His Tyr Thr Cys
                325                 330                 335

Ala Thr Asp Thr Gln Asn Ile Arg Lys Val Phe Lys Asp Val Arg Asp
                340                 345                 350

Ser Val Leu Ala Arg Tyr Leu Asp Glu Ile Asn Leu Leu
            355                 360                 365

<210> SEQ ID NO 109
<211> LENGTH: 362
<212> TYPE: PRT
<213> ORGANISM: Artificial Sequence
<220> FEATURE:
<223> OTHER INFORMATION: Description of Artificial Sequence: G protein
      chimera

<400> SEQUENCE: 109
```

```
Met Ala Arg Ser Leu Thr Trp Arg Cys Cys Pro Trp Cys Leu Thr Glu
 1               5                  10                  15

Asp Glu Lys Ala Ala Ala Arg Val Asp Gln Glu Ile Asn Arg Ile Leu
                20                  25                  30

Leu Glu Gln Lys Lys Gln Asp Arg Gly Glu Leu Lys Leu Leu Leu Leu
            35                  40                  45

Gly Pro Gly Glu Ser Gly Lys Ser Thr Phe Ile Lys Gln Met Arg Ile
        50                  55                  60

Ile His Gly Ala Gly Tyr Ser Glu Glu Glu Arg Lys Gly Phe Arg Pro
 65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
            245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Lys Gly Gln Asn Thr Tyr
            290                 295                 300

Glu Glu Ala Ala Val Tyr Ile Gln Arg Gln Phe Glu Asp Leu Asn Arg
305                 310                 315                 320

Asn Lys Glu Thr Lys Glu Ile Tyr Ser His Phe Thr Cys Ala Thr Asp
                325                 330                 335

Thr Ser Asn Ile Gln Phe Val Phe Asp Ala Val Thr Asp Val Ile Ile
            340                 345                 350

Gln Asn Asn Leu Lys Tyr Ile Gly Leu Cys
            355                 360

<210> SEQ ID NO 110
<211> LENGTH: 36
<212> TYPE: DNA
<213> ORGANISM: Artificial Sequence
<220> FEATURE:
<223> OTHER INFORMATION: Description of Artificial Sequence: PCR primer

<400> SEQUENCE: 110
```

```
gcgctctaga gttcagcaaa ggccgatctc gtccag                                36
```

<210> SEQ ID NO 111
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 111

```
gccaatgtac ttgaggtagc gggcgagcac                                       30
```

<210> SEQ ID NO 112
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 112

```
gtgctcgccc gctacctcaa gtacattggc                                       30
```

<210> SEQ ID NO 113
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 113

```
cttcagctcc ccgcgctgcc gctggctctc                                       30
```

<210> SEQ ID NO 114
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 114

```
gagagccagc ggcagcgcgg ggagctgaag                                       30
```

<210> SEQ ID NO 115
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 115

```
cttcagctcc ccgcgctgcc gctggctctc                                       30
```

<210> SEQ ID NO 116
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 116

```
gagagccagc ggcagcgcgg ggagctgaag                                       30
```

G PROTEIN

BACKGROUND OF THE INVENTION

Field of the Invention

The present invention concerns novel G protein chimeras, nucleotide sequences encoding same, host cells transformed or transfected with same, methods of determining GPCR response to a molecule, and kits for same.

The guanine nucleotide-binding proteins (G proteins) are responsible for the efficient transmission of signals from agonist-bound cell surface receptors to different intracellular effectors. Approximately 5000 G protein-coupled receptors (GPCRs) are encoded by the human genome, and most fall into the categories of being $G_q$-, $G_i$-, or $G_s$-coupled. Some G proteins are more promiscuous than others by possessing the ability to interact with a large panel of GPCRs. The most notable examples of promiscuous G proteins are the human $G_{16}$ and its murine homolog, $G_{15}$. Both $G_{15}$ and $G_{16}$ link a variety of $G_q$-, $G_i$-, and $G_s$-coupled receptors to stimulate phospholipase C (PLC); (Offermanns, S. and Simon, M., 1995, J. Biol. Chem., 270; 15175–15180; Lee, J. W. M. et al., 1998, J Neurochem., 70: 2203–2211).

G proteins are membrane-associated proteins that transduce signals from GPCRs to various intracellular effectors. G proteins within this class are heterotrimers, consisting of an $\alpha$ subunit responsible for binding guanine nucleotides, a $\beta$ subunit, and a $\gamma$ subunit. In mammalians, at least 16 distinct genes encode G protein $\alpha$ subunits. Furthermore, 5 distinct $\beta$ subunit genes as well as 12 $\gamma$ subunit genes have been identified (Clapham, D. E. and Neer, E. J., 1997, Annu. Rev. Pharmacol. Toxicol. 37, 167–203; Hildebrandt, J. D., 1997, Biochem. Pharmacol., 51, 325–339). In vivo, the $\beta$ and $\gamma$ subunits form high-affinity non-dissociating complexes, thus, a large number of $\beta\gamma$ combinations are possible. Over the past decade, both the $\alpha$ subunit and $\beta\gamma$ complexes have been shown to possess the ability to regulate effector systems (Clapham, D. E. and Neer, E. J., 1997, Annu. Rev. Pharmacol. Toxicol. 37, 167–203; Hildebrandt, J. D., 1997, Biochem. Pharmacol., 51, 325–339).

The G protein $\alpha$ subunit family is divided into four subgroups based on their amino acid sequence homology and functional diversity. The $G_s$ family, including $G\alpha_{sL}$, $G\alpha_{sS}$ and $G\alpha_{olf}$, is routinely classified as G protein $\alpha$ subunits able to mediate stimulatory regulation of adenylyl cyclase isoforms. The $G_q$ family of $\alpha$ subunits, including $G\alpha_q$, $G\alpha_{11}$, $G\alpha_{14}$ and $G\alpha_{16}$, promotes the activation of $\beta$-isoforms of PLC. $G\alpha_{12}$ and $G\alpha_{13}$ are recently identified as the regulators of $Na^+$-$H^+$ exchangers and small molecular weight-G protein signaling cascades through the interaction with at least two guanine nucleotide exchange factors of Rho. The $G_i$ family, which contains 10 members—$G\alpha_{i1}$, $G\alpha_{i2}$, $G\alpha_{i3}$, $G\alpha_{o1}$, $G\alpha_{o2}$, $G\alpha_{o3}$, $G\alpha_{t1}$, $G\alpha_{t2}$, $G\alpha_{gust}$ ($G\alpha_{t3}$), and $G\alpha_z$—was originally defined as the G protein $\alpha$ subunits closely related to those able to mediate inhibition of adenylyl cyclase (which is true of all $G\alpha_i$ subtypes, as well as $G\alpha_z$). $G\alpha_o$ subtypes mainly regulate calcium ion channels, while $G\alpha_t$ subtypes activate cGMP phosphodiesterases.

Because of their promiscuity, $G_{15}$ and $G_{16}$ have to date been recognised as being ideal candidates for linking "orphan" receptors (cloned receptors without a known ligand) to PLC and its downstream effectors. Hence, $G_{16}$ has received considerable attention as a potential tool for drug discovery (Milligan, G. et al., 1996, Trends in Pharmacol. Sci., 17: 235–237). Although $G_{15}$ and $G_{16}$ are more promiscuous than other G proteins, they are not true universal adapters for GPCRs. For example, the CCR2a chemokine receptor (Kuang, Y. et al., 1996, J. Biol. Chem., 271: 3975–3978), the $\alpha_{1A}$- and $\alpha_{1C}$-adrenoceptors (Wu, D. et al., 1992, J. Biol. Chem., 267: 25798–25802) are unable to recognize $G_{16}$. Indeed, of thirty-three different GPCR examined to date (Offermanns, S. and Simon, M., 1995, supra; Lee, J. W. M. et al., 1998, supra; Kuang, Y. et al., 1996, supra; Wu, D. et al., 1992, supra; Wu, D. et al., 1993, Science, 261: 101–103; Zhu, X. and Birnbaumer, L., 1996, PNAS USA, 93: 2827–2831; Parmentier, M. L. et al., 1998, Mol. Pharmacol., 53: 778–786), at least six receptors are incapable of activating $G_{16}$.

Most of the GPCRs that fail to activate $G_{16}$ belong to the $G_i$-coupled receptor subfamily. The term $G_i$-coupled receptors stands for a group of seven transmembrane receptors that can interact with all three subtypes of $G\alpha_i$ ($G\alpha_{i1-3}$) as well as $G\alpha_z$. Binding of a proper agonist to the receptor triggers the activation of the associated $\alpha$ subunits by promoting the release of GDP and the uptake of GTP. These receptors are widely distributed in different receptor categories, including aminergic, hormonal, peptidergic, purinergic, and chemokine. The $G_i$-coupled receptors constitute an exceedingly large GPCR subfamily which encompass many newly discovered receptors such as those for chemokines, however, approximately 15% of the $G_i$-coupled receptors examined to date cannot activate $G_{16}$. As previously mentioned, this poses a serious concern for using $G_{16}$ as an adapter of orphan receptors in drug screening protocols due to the large number of receptors which may not couple to or effectively couple to $G\alpha_{16}$.

The underlying rationale for the intense interest in orphan GPCRs is based in their history of being excellent therapeutic targets. Over the past several decades, drug discovery programs world-wide have combined to produce greater than 200 novel drugs that possess activity or antagonizing properties towards GPCRs. As an example, it is estimated that the majority of drug discovery initiatives within the pharmaceutical industry are focused on this signalling pathway (Roush, W., 1996, Science, 271, 1056–1058). Likewise, the significance and complexity of GPCRs is readily apparent in the number of cases of genetic diseases that are known to be linked to various defects in these receptors (Dryja, T. P., et al., 1990, Nature, 343, 364–366; Sung, C-H. et al., 1991, Proc. Nal. Acad. Sci. U.S.A., 88, 6481–6485; Parma, J. et al., 1993, Nature, 365, 649–651; Shenker, A., et al., 1993, Nature, 365, 652–654; van den Oiweland, A. M., et al., 1992, Nat. Genet, 2, 99–102; Pan, Y., et al., 1992, Nat. Genet., 2, 103–106; Rosenthal, W. et al., 1993, J. Biol. Chem., 268, 13030–13033; Pollak, M. R., et al., 1993, Cell, 75, 1297–1303; Pollak, M. R., et al., 1994, Nat. Genet., 8, 303–307; Schipsni, E., et al., 1995, Science, 268, 98–100; Walston, J. et al., 1995, New Engl. J. Med., 333, 343–347; Widen, E., et al., 1995, New Engl. J. Med., 333, 348–351; Clement, K., et al., 1995, New Engl. J. Med., 333 352–354; Wajnrajch, M. P., et al., 1996, Nat. Genet., 12, 88–90; Clark, A. J. L., et al., 1993, Lancet, 341,461–462; Hager, J., et al., 1995, Nat Genet., 9, 299–304). As a result of the proven link of GPCRs to a wide variety of diseases and the historical success of drugs that target these receptors, characterisation of orphan GPCRs are among the most promising molecular targets for future drug discovery platforms. The ability to couple orphan GPCRs to down stream effectors via a small number of discriminating G proteins would greatly accelerate validation of GPCRs as potential drug targets and hence, further accelerate the discovery of novel therapeutics.

In light of the exceedingly large number of GPCRs, the characterisation of this class of proteins in toti is impractical, yet it remains necessary to identify ligands, particularly therapeutically effective ligands, for orphan receptors. Thus there is a need for an improved G protein with an increased promiscuity for binding to GPCRs (particularly $G_i$-coupled receptors) in order to link them to PLC and other downstream effectors. In theory, this would provide the means to identify useful ligands that bind to orphan receptors and result in the activation of an engineered G protein (possessing increased promiscuity) which would then allow the coupling of the receptor to a measurable downstream effector. If such ligands demonstrated high binding specificities towards a putative GPCR, they would become extremely useful research tools for delineating the receptor's function and signal transduction pathway(s). Thus, identification of such ligands could play an important role in the validation of orphan receptors as viable drug targets, if such receptors were ultimately linked to discernible human disease states.

Several studies have indicated that distributed on the Gα subunit are multiple domains which confer specificity to GPCRs (Conklin, B. R. et al., 1993, Nature, 363: 274–276; Lee, C. H. et al., 1995, Mol. Pharmacol., 47: 218–223; Liu, J. et al., 1995, PNAS USA, 92: 11642–11646; Conklin, B. R. et al., 1996, Mol. Pharmacol., 50: 858–890; Kostenis, E. et al., 1997, J. Biol. Chem., 272: 23675–23681; Kostenis, E. et al., 1998, J. Biol. Chem., 273: 17886–17892). Modification of either amino or carboxyl-termini of Gα proteins has demonstrated the importance of such domains. The present invention, however, by using novel chimera Gα proteins, provides improved G proteins with greatly increased and enhanced promiscuity for GPCRs, particularly for $G_i$- and $G_s$-coupled receptors.

BRIEF SUMMARY OF THE INVENTION

Experiments (below) have shown that Gα proteins having such substitutions have an increased promiscuity for GPCRs. Previously constructed chimeric Gα proteins (Chang, H. L. et al., 1995, Molecular Pharmacology, 47: 218–223), which included carboxyl-terminal substitutions, failed to increase G protein promiscuity and provided no suggestion as to how promiscuity might be improved. The difficulties experienced in improving G protein promiscuity are demonstrated by the large number of constructs made by the investigators which failed to improve promiscuity.

Thus according to the present invention there is provided a chimera comprising a Gα protein other than $G\alpha_z$ having substituted at least one of the group of its carboxyl-terminal β-sheet and/or α5-helix by that of $G\alpha_z$.

Also provided according to the present invention there is a chimera comprising a Gα protein other than $G\alpha_s$ having substituted at least one of the group of its carboxyl-terminal β-sheet and/or α5-helix by that of $G\alpha_s$.

In particular, the Gα protein which is substituted may comprise $G\alpha_{16}$.

Also provided are nucleotide sequences encoding chimeras of the present invention, host cells transformed or transfected with same, methods of determining GPCR response to a molecule, and kits for same.

BRIEF DESCRIPTION OF THE FIGURES

FIG. 3 shows alignment of amino acid sequences of $G\alpha_{16}$, $G\alpha_z$ and their chimeras. The amino acid sequences of the N- and C-termini of $G\alpha_{16}$ and $G\alpha_z$ are aligned using the Clustal X program. Gaps introduced for better alignment of the sequences are hyphenated. Residues of $G\alpha_z$ that are identical to $G\alpha_{16}$ are shown as a dot. Numbers shown represent the relative positions of the amino acids of $G\alpha_{16}$ and $G\alpha_z$. Shaded horizontal bars depict sequences of the chimeras that are identical to $G\alpha_{16}$. Putative secondary structures based on the $G\alpha_{t1}$ crystal structure are indicated by striped (α helix) and solid (β strand) horizontal bars above the $G\alpha_z$ sequence. The full sequence for 30z16 is SEQ ID NO: 108. The sequence for 16z66 is SEQ ID NO: 109. 16z25 is SEQ ID NO: 1 (above). 16z44 is SEQ ID NO: 2 (above).

DETAILED DESCRIPTION OF THE INVENTION

As detailed below, a series of chimeras were constructed (utilizing the nucleotide sequences encoding $G\alpha_{16}$, $G\alpha_z$ and $G\alpha_s$) by means of the polymerase chain reaction (PCR) where human $G\alpha_{16}$, rat $G\alpha_z$ and mouse $G\alpha_s$ cDNAs served as templates for the reactions. Subsequently, these chimeras were subcloned into the pcDNA3 mammalian expression vector. Experiments were performed to test the ability of the chimera constructs to mediate receptor-induced stimulation of the reporter enzyme PLC. With respect to the $G\alpha_{16/z}$ chimeras, immunodetection and functional analysis of their constitutively activated mutants verified expression of the proteins. Two $G\alpha_{16/z}$ chimeras altered at their carboxyl termini (designated 16z25 and 16z44, respectively) were capable of responding to all fourteen G$_i$-proteins coupled receptors tested, including those receptors unable to associate with native $G\alpha_{16}$. Moreover, these responses were more efficiently mediated (higher maximal and lower EC$_{50}$) by 16z44 than by $G\alpha_{16}$. Interactions between our GCPR test panel and all other chimera constructs used in these studies, which were modified either at their carboxyl terminus, amino terminus or both termini were significantly diminished or abolished.

Chimeras of the invention may for example comprise $G\alpha_{16}$ having their carboxyl terminal α5-helix substituted by that of $G\alpha_z$ or $G\alpha_s$. For example, this may be achieved by substituting the 25 carboxyl-terminal residues of $G\alpha_{16}$ with approximately the last 25 carboxyl-terminal residues of $G\alpha_z$ or $G\alpha_s$. Such chimeras would have the sequences of SEQ ID NO: 1 or SEQ ID NO: 3 and are designated as 16Z25 and 16S25, respectively.

Additionally, chimeras having their carboxyl-terminal D-sheet and a-helix substituted by those of $G\alpha_z$ or $G\alpha_s$ may also be generated. This would be achieved by for example substituting the 44 carboxyl-terminal residues of $G\alpha_{16}$ with approximately the last 44 carboxyl-terminal residues of $G\alpha_z$ or $G\alpha_s$. Such chimeras may have the sequences of SEQ ID NO: 2 or SEQ ID NO: 4 and are designated as 16Z44 and 16S44, respectively.

Figure 1:
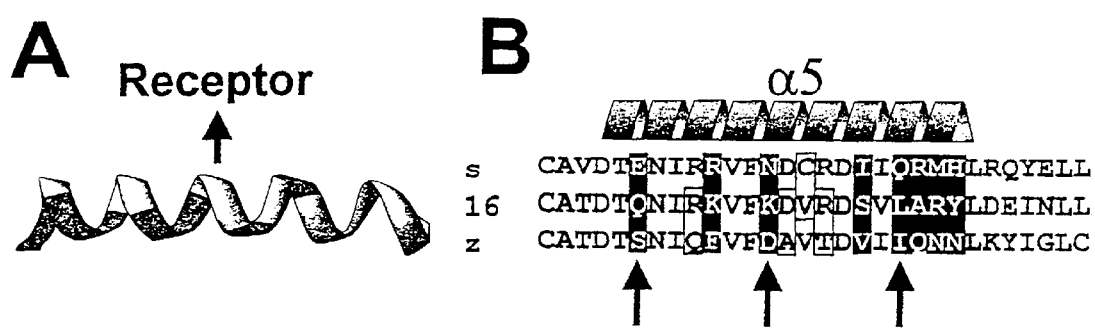
FIGS. 1A & 1B show (A) a putative model of the C-terminal α5 helix of $G\alpha_{16}$. Positions in light gray are those of non-conserved residues when compared with the corresponding helical regions of $G\alpha_S$ and $G\alpha_Z$. Most of these residues are located on the putative receptor-facing side of the α5 helix. (B) shows alignment of the amino acid sequence of the putative α5 helices of $G\alpha_{16}$ (residues 349–369 of SEQ ID NO: 105), $G\alpha_S$ (residues 368–388 of SEQ ID NO: 106) and $G\alpha_Z$ (residues 330–350 of SEQ ID NO: 107) using the program Clustal W. The inverted colour residues are those not conserved among all three candidates. Boxed residues are divergent between $G\alpha_{16}$ and $G\alpha_S$ or between $G\alpha_{16}$ and $G\alpha_Z$. The 3 residues indicated by arrows have been examined for their potential roles towards receptor specificity.

It is well accepted that the receptor coupling specificity of G protein α subunits is correlated to the identity of the C-terminus. Homologous mutations of this region from the identity of one G protein α subunit to another may alter the receptor coupling profile specifically. Furthermore, a wider spectrum of G protein coupled receptors is anticipated to transmit signals to a composite mutant of G protein α subunit which acquires various molecular determinants for recognizing different receptors. By using $G\alpha_{16}$ as the backbone structure, subsequent replacement of its C-terminal helical region (and the tail) with the corresponding sequence of $G\alpha_z$ or $G\alpha_s$ has increased the coupling of these chimeras to G$_i$-coupled and G$_s$-coupled receptors. Interestingly, the replacement of the last 6 residues of $G\alpha_{16}$ to either those of $G\alpha_{i2}$ or $G\alpha_s$ cannot redirect the coupling specificity. The results suggest that the identity of the C-terminal α5 helix is important for determining the receptor coupling profile of $G\alpha_{16}$. Alignment of the C-terminal regions of $G\alpha_s$, $G\alpha_z$ and $G\alpha_{16}$ shows that clusters of amino acids are not conserved between the three homologues. Although the differences between two particular individuals are not exactly the same as in the other pairs, particular amino acid positions are divergent in all three sequences (FIG. 1B). According to the amino acid sequence of $G\alpha_{16}$, they are Gln-350, Lys-357 and a small cluster (Leu-364 to Tyr-367), which are all facing outwards from the core structure of the G protein α subunit (FIG. 1A) and occurred every 7 residues, about two turns of the helix. Point mutants of the $G\alpha_{16/z}$ and $G\alpha_{16/s}$ chimeras that result in the conservative substitution(s) (either in isolation or various combinations) of amino acids at positions 350, 357 and 364 of the putative α5 helix are predicted to retain the structural integrity of the said helix and thus, the functional coupling properties of the chimeras as well. Such mutants may be formed from the molecules of SEQ ID NOs: 1–4. Thus also provided according to the present invention is a chimera according to the present invention possessing at least one conservative amino acid substitution selected from the group of those at positions 350, 357 and 364 that conserve the structural integrity of the α5 helix, the chimera having the amino acid sequence of any one of SEQ ID NOs: 5–92.

Of the nucleotide sequences encoding the chimeras of the present invention, the coding sequences of the various chimeras may be operatively linked to an expression control sequence sufficient to drive expression. Recombinant DNA in accordance with the invention may be in the form of a vector, for example a plasmid, cosmid or phage. A vector may include at least one selectable marker to enable selection of cells transfected (or transformed) with the vector. Such a marker or markers may enable selection of cells harbouring vectors incorporating heterlogous DNA. The vector may contain appropriate start and stop signals. The vector may be an expression vector having regulatory sequences to drive expression. Vectors not having regulatory sequences may be used as cloning vectors (as may expression vectors).

Cloning vectors can be introduced into suitable hosts that facilitate their manipulation. The host cells transfected or transformed with DNA according to the present invention may be prokaryotic or eukaryotic. Eukaryotic hosts may include yeast, insect and mammalian cell lines. Expression hosts may be stably transformed. Transient and cell-free expression systems may also be used. Expression hosts may contain other exogenous DNA to facilitate the expression, assembly, secretion and other aspects of the biosynthesis of molecules of the invention.

DNA according to the present invention may be prepared by any convenient method involving coupling together successive nucleotides, and/or ligating oligo- and/or poly-nucleotides, including in vitro processes, as well as by the more usual recombinant DNA technology.

Cells transformed or transfected such that they express the protein of the present invention may express it as part of an assay system to detect the GPCR response or to detect orphan GPCR response. Such receptor assay systems are well know in the art (see Milligan, G. et al., 1996, supra and references therein).

A method of determining GPCR response to a molecule comprises the steps of:
  i) contacting a cell according to the present invention with said molecule;
  ii) detecting any reporter assay system response; and
  iii) correlating the results of detection step (ii) with G protein-coupled receptor response to said molecule.

The molecule may for example be a ligand for the receptor, although of course in for example mass-screening of molecules, some may not be ligands and so may not bind the receptor, thus providing a negative result.

Naturally, such methods provide an excellent basis for screening receptor agonists.

A kit for performing a method according to the present invention may include a cell according to the present invention which expresses an assay system for detecting GPCR response.

The DNA manipulation techniques employed in the present invention include those known to a person skilled in the art, for example: PCR (McPherson, M. J. et al., 1991, PCR: A practical approach, Oxford University Press, Oxford); DNA cloning and analysis (Sambrook, J. et al., 1989, Molecular cloning: a laboratory manual, Cold Spring Harbour Laboratory, New York); DNA sequencing (Sanger, F. et al., 1977, PNAS USA 74(12): 5463–5467; PCR (Volume 1): A practical approach. Eds. M. J. McPherson, P. Quirke and G. R. Taylor. Oxford University Press, 1991; Harlow, E. and Lane, D., "Using Antibodies: A Laboratory Manual", Cold Spring Harbor Laboratory Press, New York, 1998).

EXAMPLE 1

The rat $G\alpha_z$ cDNA was used for construction of the various $G\alpha_{16/z}$ chimeras due to its availability and the fact that the corresponding nucleotide sequence associated with the N- and C-termini of $G\alpha_z$, and which were used in the construction of the various chimeras, encodes the identical amino acid sequence regardless of whether the $G\alpha_z$ origin is that of human or of rat.

Materials

The $G\alpha_{16}$ cDNA is as detailed in Amatruda III, T. T. et al. (1991, Proc. Natl. Acad. Sci. USA, 88:5587–5591). The $G\alpha_s$ cDNA is as detailed in Sullivan, K. A. etal. (1986, Proc. Natl. Acad. Sci. USA, 83, 6687–6691). All other cDNAs used were constructed or obtained as previously described (Lee, J. W. M. et al., 1998, supra; Wong, Y. H. et al., 1992, Science, 255: 339–342; Tsu, R. C. and Wong, Y. H., 1996, J. Neurosci., 16: 1317–1323). Simian kidney fibroblast COS-7 cells were obtained from the American Tissue Type Culture Collection (ATCC CRL-1651). Receptor agonists were purchased from Research Biochemicals Inc. (Natick, Mass.), Sigma (St. Louis, Mo.) or Tocris Cookson (Bristol, U.K.). Antisera against $G\alpha_{16}$ and $G\alpha_z$ were from Calbiochem (San Diego, Calif.). Sequenase Version 2.0 DNA sequencing kit and ECL chemiluminescence detection kits were purchased from Amersham Pharmacia Biotech. [$^3$H] myo-inositol was from NEN Dupont Inc. (Boston, Mass.). Plasmid DNA purification columns were obtained from Qiagen (Hilden, Germany). $G\alpha_z$-specific antisera 3A-170 (C-terminal) and 3–18 (N-terminal) were obtained from Gramsch Laboratories (Schwabhausen, Germany) and Calbiochem (La Jolla, Calif.), respectively. Taq DNA polymerase, restriction endonucleases, custom mutation primers and cell culture reagents were obtained from Life Technologies Inc. (Grand Island, N.Y.) and all other chemicals were purchased from Sigma (St. Louis, Mo.).

Methods

Construction of Chimeras and Mutants

All chimeras described hereinafter were constructed using PCR methodology. The chimeras constructed were 16z25, 16z44, 16z66 and 30z16. The first three comprised $G\alpha_{16}$ having its C-terminal 25, 44 and 66 amino acids respectively replaced by those of Gα$_z$. 30z16 comprises Gα$_{16}$ having its 30 N-terminal amino acids replaced by those of Gα$_z$. Human Gα$_{16}$ and rat Gα$_z$ cDNAs (subdloned in the XbaI and EcoRI sites of pcDNAI, respectively) served as the templates for the various reactions with T7 and SP6 promoter sequences providing the outer flanking priming regions. A pair of chimera primers covering both the nucleotide sequences of Gα$_{16}$ and Gα$_z$ were designed as appropriate for each chimera construct. Firstly, two overlapping fragments that corresponded to the portions of Gα$_{16}$ and Gα$_z$ were generated. The 5' fragment was made with T7 primer and the reversed chimera primer, while the 3' fragment was made with the forward chimera primer and a primer annealed to the SP6 promoter on the vector sequence (SP6 primer). The two PCR products were annealed together and the full-length fragments were made using the T7 and SP6 primers. A general overview of this technique is provided in FIG. 2. Specific primers used for the construction of the various chimeras are listed in Table 3 with the nucleotide sequences of Gα$_z$ underlined, each primer being composed of Gα$_{16}$- and Gα$_z$-specific sequences. Numbers in brackets in Table 3 refer to the position of the nucleotides in the open reading frame of Gα$_{16}$ or Gα$_z$. For the construction of 16z3, a termination codon (small letters in Table 3, nucleotides 13–15) and an artificial XbaI site (bold letters in Table 3, nucleotides 5–10) were engineered into the primer. 1.5 mM MgCl$_2$ was included in the PCR reaction mixture and the PCR products were amplified with thermal cycling at 94° C.(60 seconds)/50° C. (90 seconds)/72° C. (90 seconds) for 30 cycles using Robocycler 40 from Stratagene (La Jolla, Calif.). The 30z16z44 and 30z16z66 chimeras were constructed in a similar manner except one of the half products was amplified by PCR using either the 16z44 or 16z66 chimera as the template. Full-length chimera α subunit cDNAs were subcloned into either pcDNA3 or pcDNA3.1Zeo(+) mammalian expression vectors (Invitrogen, San Diego, Calif.). DNA sequences of the mutants were checked by dideoxynucleotide sequencing method using Sequenase V2.0 kit and restriction mapping.

A GTPase-deficient mutant of Gα$_{16}$ (Gα$_{16}$QL) with Gln-212 mutated into Leu was constructed essentially as described previously (Qian et al., .1994, J. Biol. Chem., 269: 17417–17423). Functional constitutive activity of Gα$_{16}$QL was confirmed by transiently expressing the construct in COS-7 cells and determining the basal PLC activity in the transfectants. A Hind III/Xcm I fragment from Gα$_{16}$QL was used to construct the GTPase-deficient mutants of 16z25, 16z44 and 16z66. The resultant mutant chimera constructs were verified by restriction mapping.

Construction of the Gα$_{16/s}$ chimeras was achieved using a similar PCR methodology as described for the construction of the Gα$_{16/z}$ chimeras except for the modifications that follow. In the case of the Gα$_{16/s}$ chimeras, human Gα$_{16}$ and mouse Gα$_S$ cDNAs (subcloned in the XbaI site of mammalian expression vector pcDNA3) served as the templates for the various reactions. A pair of chimera primers covering both the nucleotide sequences of Gα$_{16}$ and Gα$_S$ were designed as appropriate for each chimera construct. The specific primers used for the construction of the two Gα$_{16/s}$ chimeras are listed below with the nucleotide sequences of Gαs underlined: 16s25/S: TAC ACA TGT GCC ACA GAC ACT GAG AAC ATC (SEQ ID NO: 101); 16s25/AS: GAT GTT CTCAGT GTC TGT GGC ACA TGT GTA (SEQ ID NO: 102); 16s44/S: GGC CCC GAG GGC AGC GCT AGT GGA GAT (SEQ ID NO: 103); 16s44/AS: ATC TCC ACT AGC GCT GCC CTC GGG GCC (SEQ ID NO: 104). (Note: the same nomenclature has been employed to designate the Gα$_{16/s}$ chimeras as that used to described the Gα$_{16/z}$ chimeras.) All PCR products pertaining to the Gα$_{16/s}$ chimeras were amplified with thermal cycling at 95° C. (60 seconds)/50° C. (60 seconds)/72° C. (60 seconds) for 30 cycles using Robocycler 40 from Stratagene (La Jolla, Calif.). The corresponding chimera PCR products were then subdloned into the XbaI site of pcDNA3 mammalian expression vector (Invitrogen, San Diego, Calif.) prior to sequence verification. Veri thermal cycling at 95° C. (60 seconds)/50° C. (60 seconds)/72° C. (60 seconds) for 30 cycles using Robocycler 40 from Stratagene (La Jolla, Calif.). Identification of the chimera sequences was performed by the dideoxynucleotide sequencing method using Sequence V2.0 kit, as well as restriction mapping.

Transfection of COS-7 Cells

Simian kidney fibroblast COS-7 cells were cultured with Dulbecco's modified Eagle's medium (DMEM) supplemented with 10% fetal calf serum (FCS) (vol/vol), 50 units/ml penicillin and 50 μg/ml streptomycin at 37° C. in humidified air with 5% $CO_2$. $1\times10^5$ cells/well were seeded onto 12-well plates the day before transfection. DEAE-dextran mediated transfection was performed as described by Wong, Y. H. (1994, Methods Enzymol., 238: 81–94). Briefly, appropriate amounts of various DNA samples purified by Qiagen column chromatography were mixed with growth medium containing 250 μg/ml DEAE-dextran and 100 μM chloroquine. Cells were incubated with the transfection cocktails for approximately 3.5 hours and then shocked for 1 minute at room temperature in PBS containing 10% dimethylsulfoxide (vol/vol). After rinsing with PBS, the cells were returned to growth media for 24 hours. Approximately 50% of the cell population took up the cDNAs as indicated by cotransfecting a plasmid DNA encoding β-galactosidase as a reporter.

Inositol Phosphates (IP) Accumulation Assay

750 μl of inositol-free DMEM containing 5% FCS and 2.5 μCi/ml [$^3$H]myo-inositol was added to each well of transfected COS-7 cells and incubated for 18–24 hours. The labelling media was subsequently replaced by 1 ml of inositol phosphate assay medium (DMEM buffered with 20 mM 4-(2-hydroxyethyl)-1-piperazine ethanesulfonic acid (HEPES), pH 7.5, and 20 mM LiCl) for 10 minutes and then 1 ml of IP assay medium containing the appropriate agonist was added to the cells for an additional hour at 37° C. Reactions were stopped by adding 750 μl of ice-cold 20 mM formic acid and stored at 4° C. for 30 minutes. [$^3$H]inositol phosphates were separated from other labeled inositol species by sequential ion-exchange chromatography as described by Tsu, R. C. et al. (1995a, J. Neurochem., 64: 2700–2707).

Membrane Protein Preparation and Immunodetection of Recombinant Proteins

COS-7 cells were grown on 150-mm dishes to 70–80% confluence. Transfection of the cells was performed as essentially described using a 12-well plate format except that proper adjustments were made to the volumes and amounts of the various reagents used. After 48 hours under normal growth conditions, cells were washed with $Ca^{2+}$/$Mg^{2+}$-free PBS (PBS-CMF) and harvested using 5 ml PBS-CMF containing 10 mM EDTA. The following procedures were performed at 4° C. Cells were spun down briefly (200×g, 5 minutes), resuspended in hypotonic lysis buffer (50 mM Tris-HCl, 2.5 mM MgCl$_2$, 1 mM EGTA, 0.1 mM phenylmethylsulfonylfluoride, 1 mM benzamidine-HCl, 1 mM dithiothreitol; pH 7.4) and lysed by one cycle of freeze-thawing followed by 10 passages through a 27-gauge needle. Nuclei were removed from the lysed sample by centrifugation. Membranes from the resultant supernatants were then collected by spinning at 15,000×g for 15 minutes. The membrane pellets were finally resuspended in lysis buffer. Protein concentrations were determined using the Bio-Rad Protein Assay Kit. For immunodetection, 50 μg of each membrane protein sample was resolved on a 10% SDS-polyacrylamide gel and transferred to PVDF membranes utilizing electroblotting technology. Protein molecular weight markers were visualized by Coomassie Blue staining. Several chimeras were detected by the $G\alpha_z$-specific antiserum purchased from Calbiochem and with the chemiluminescence ECL kit, purchased from Amersham.

Data Analysis

[$^3$H]IP was estimated by determining the ratios of [$^3$H]IP to [$^3$H]inositol plus [$^3$H]IP as described by Tsu, R. C. et al. (1995a, supra). Absolute values for IP accumulation varied between experiments, but variability within a given experiment was less than 10% in general. Unless otherwise stated, data shown in the figures and tables represent the mean±SEM of three or more independent experiments performed in triplicate. Bonferroni t-test with 95% confidence was adopted to verify the significance between different treatment groups within the experiments.

RESULTS

Design of C-terminal Chimeras

Although multiple regions in the primary structure of $G\alpha_{16}$ are required for receptor coupling (Lee, C. H. et al., 1995, supra), the molecular determinants for the promiscuous property of $G\alpha_{16}$ have not been fully delineated. Numerous studies on other α subunits have implicated the C-terminal tail of the α chain as one of the major receptor contact regions (Conklin, B. R. et al., 1993, supra; Conklin, B. R. et al., 1996, supra; Sullivan, K. A. etal., 1987, Nature, 330: 758–760; Tsu, R. C. etal., 1997, Mol. Pharmacol., 52: 38–45). As a first step towards enhancing the ability of $G\alpha_{16}$ to recognize $G_i$-coupled receptors, a series of $G\alpha_{16/z}$ chimeras were constructed by incorporating different lengths of the $G\alpha_z$ sequence at the C-terminus of $G\alpha_{16}$. $G\alpha_z$ recognizes most $G_i$-coupled receptors (Chan, J. S. C. et al., 1995, J. Neurochem., 65: 2682–2689; Chan, J. S. C. et al., 1998, J. Neurochem., 71: 2203–2210; Lai, H. W. L. et al., 1995, FEBS Lett., 360: 97–99; Tsu, R. C. et al., 1995a, supra; Tsu, R. C. et al., 1995b, Biochem. J., 309: 331–339; Shum, J. K. et al., 1995, Biochem. Biophys. Res. Commun., 208: 223–229; Yung, L. Y. et al., 1995, FEBS Lett., 372: 99–102; Wong, Y. H. et al., 1992, supra) but is insensitive to pertussis toxin (PTX). Signals transduced by chimeras of $G\alpha_{16/z}$ can be easily discerned from non-specific $G_i$-coupled receptor mediated signals with the use of PTX.

Because the α5 helix is a known contact region for receptors (Lichtarge et al., 1996, Proc. Nat. Acad. Sci. USA, X, 7507–7511), we replaced the entire α5 helix of $G\alpha_{16}$ with that of $G\alpha_z$. Based on the crystal structures of $G\alpha_{t1}$ (Lambright et al., 1996, Nature, 379: 311–319) and $G\alpha_{i1}$ (Wall et al., 1995, Cell, 83: 1047–1058), the α5 helix of $G\alpha_{16}$ is predicted to be composed of the last twenty-five residues. The resultant chimera was therefore named 16z25; for 16z25 and subsequent chimeras, the number following the letter "z" (or "s" in the case of $G\alpha_{16/s}$ chimeras) indicates the number of $G\alpha_z$ (or $G\alpha_s$ in the case of $G\alpha_{16/s}$ chimeras) residues present in the C-terminus of the construct.

A unique structural feature of $G\alpha_{16}$ is an insertion of eleven residues (amino acids 325–336; based on the alignment of all mammalian Gα subunits using the Clustal X sequence analysis program), which are absent in all other Gα subunits. Furthermore, the inserted amino acid residues are positioned between the $\alpha^4$ helix and the β6 strand secondary structures of this G protein. To test whether this insertion is critical for the promiscuity of $G\alpha_{16}$, the 16z44 chimera was constructed. In this chimera, half of the α4/β6 insertion was replaced by $G\alpha_z$ residues without shortening the insertion (FIG. 3). Lastly, the α4/β6/α5 domains of $G\alpha_{16}$ were replaced with the cognate regions of $G\alpha_z$ by creating a 16z66 chimera with a junctional site between the αG and α4 helices (FIG. 3). The 16z66 chimera is derived by the substitution of approximately 20% of the C-terminal residue sequence of $G\alpha_{16}$ with residues derived from $G\alpha_z$ which in turn created a recombinant species which is shorter than $G\alpha_{16}$ by twelve amino acids. No epitope tag was engineered into the various chimeras as it may potentially disrupt receptor recognition.

Functional Coupling of $G\alpha_{16/z}$ Chimeras to the δ-opioid Receptor

Figure 4:
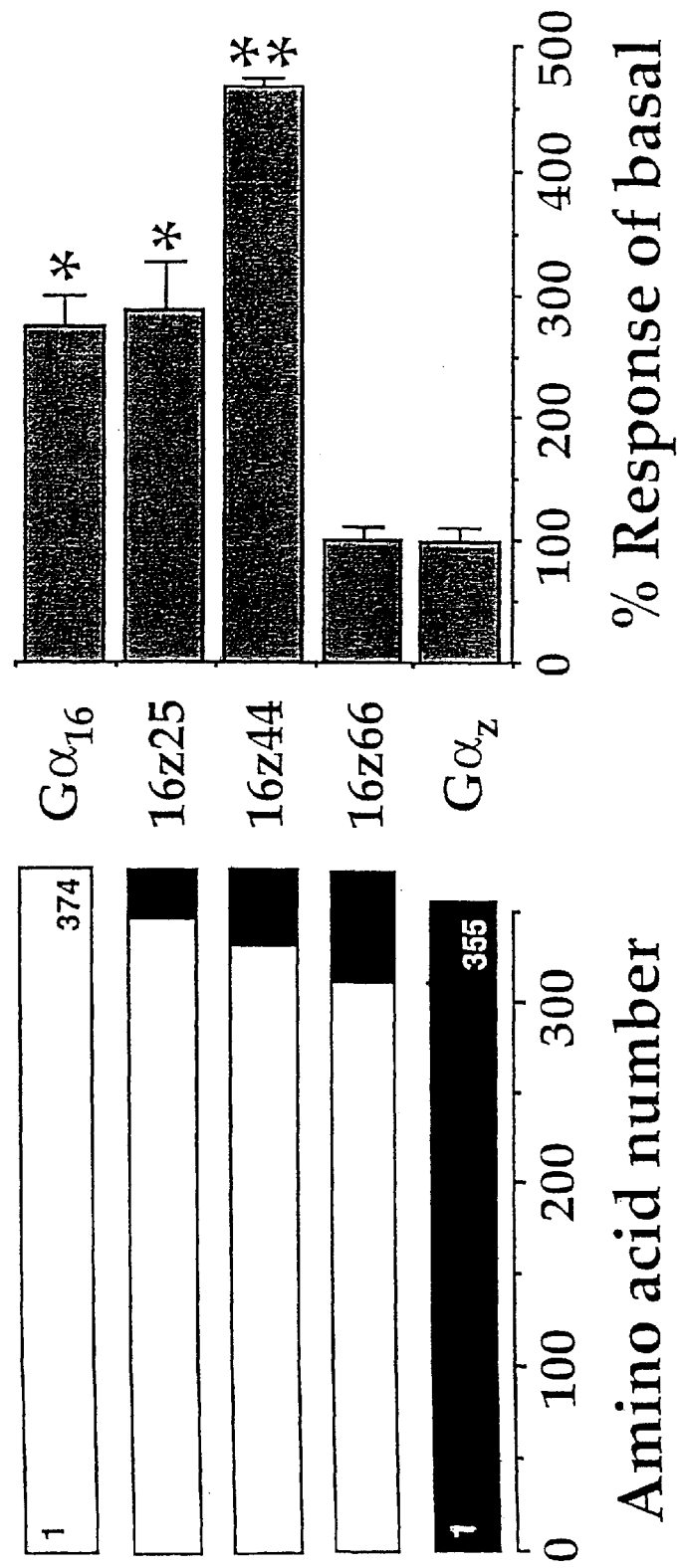
FIG. 4 shows stimulation of PLC by the δ-opioid receptor via the 16z25 and 16z44 chimeras. $G\alpha_{16/z}$ chimeras were constructed as described in Materials and Methods. Schematic representation of the chimeras are shown on the left. Activation of PLC was determined by transfecting COS-7 cells with cDNAs (0.25 μg/ml each) encoding the δ-opioid receptor and one of the five chimera G proteins: 16z3, 16z6, 16z25, 16z44 or 16z66. Additional transfections with the wild-type $G\alpha_{16}$ and $G\alpha_z$ were carried out as controls. Transfected cells were labelled with 2.5 μCi/ml [$^3$H]inositol 20–24 hours prior to the assay. Formation of IP was measured in the absence and presence of 100 nM DPDPE. Results are expressed as percentage stimulation of IP production as compared to basal activity. Basal values expressed as the ratio (×10$^3$) of IP to total inositols ranged from 6.55±0.52 to 9.24±0.43. *DPDPE-induced IP formation was significantly higher than basal levels. **DPDPE-stimulated IP accumulation was significantly higher than that observed in the $G\alpha_{16}$ transfected cells; Bonferroni t-test, $P<0.05$.

A well-established transient expression system was used to examine the ability of the $G\alpha_{16/z}$ chimeras to interact with $G_i$-coupled receptors. It has previously been shown that co-expression of the δ-opioid receptor (a typical $G_i$-coupled receptor) and $G\alpha_{16}$ in COS-7 cells permits the δ-selective opioid agonist, [D-Pen$^2$,D-Pen$^5$]enkephalin (DPDPE), to stimulate the formation of IP (Lee, J. W. M. et al., 1998, supra). The same approach was adopted to study the $G\alpha_{16/z}$ chimeras. In accordance with Lee, J. W. M. et al. (1998, supra), 100 nM DPDPE stimulated IP formation by 3-fold in COS-7 cells coexpressing the $G\alpha_{16}$ and the δ-opioid receptor (FIG. 4). In contrast, agonist treatment failed to evoke formation of IP in COS-7 cells cotransfected with cDNAs encoding the δ-opioid receptor and $G\alpha_z$ (FIG. 4). In COS-7 cells co-expressing the δ-opioid receptor with either 16z25 or 16z44, 100 nM DPDPE stimulated the formation of IP by 3–4.5 folds (FIG. 4). Interestingly, the DPDPE response was significantly higher in cells transfected with the 16z44 cDNA than those expressing 16z25 or $G\alpha_{16}$ (FIG. 4 and Table 1). These results indicate that too little or too extensive substitution of the carboxy terminal sequence of $G\alpha_{16}$ by $G\alpha_z$ residues impairs the ability of the resultant chimeras to interact with the δ-opioid receptor. Three of the chimeras (16z3, 16z6 and 16z66) also failed to mediate the DPDPE response under identical experimental conditions (FIG. 4), despite the fact that they were indeed expressed in the transfected COS-7 cells (see below). Alterations of the last three to six amino acids of $G\alpha_{16}$ appears to prevent the resultant chimeras from recognizing the δ-opioid receptor, and thus, the carboxy terminal 20% of $G\alpha_{16}$ may be required for its promiscuity.

Figure 5:
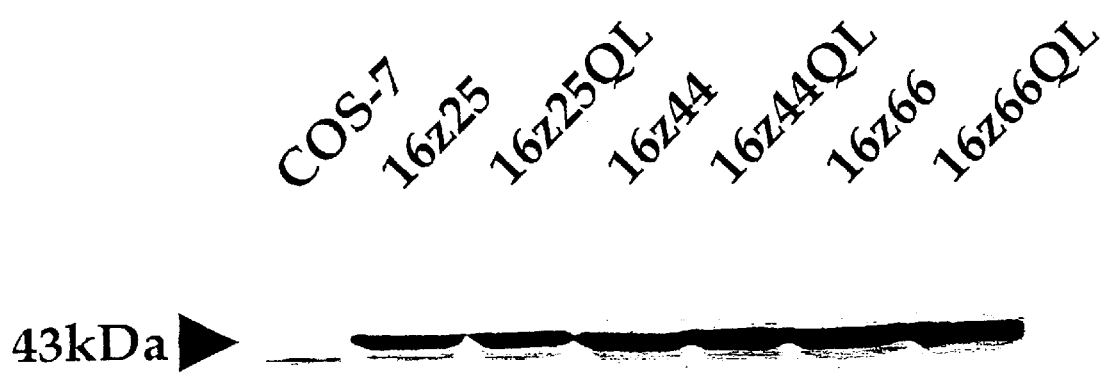
FIG. 5 shows immunodetection of chimera $G\alpha_{16/z}$ subunits. COS-7 cells were transiently transfected with cDNAs encoding the wild-type or constitutively active mutants of 16z25, 16z44, and 16z66. Plasma membranes were prepared 48 hours post-transfection. 50 μg of membrane proteins were separated on a 12.5% polyacrylamide SDS gel and electrophoretically transferred to PVDF membranes. Protein markers were localized by Ponceau S staining and the chimeras were immunodetected with the 3A-170 antiserum against the C-terminus of $G\alpha_z$. Two independent experiments with different batches of membrane proteins yielded similar results.
Figure 6:
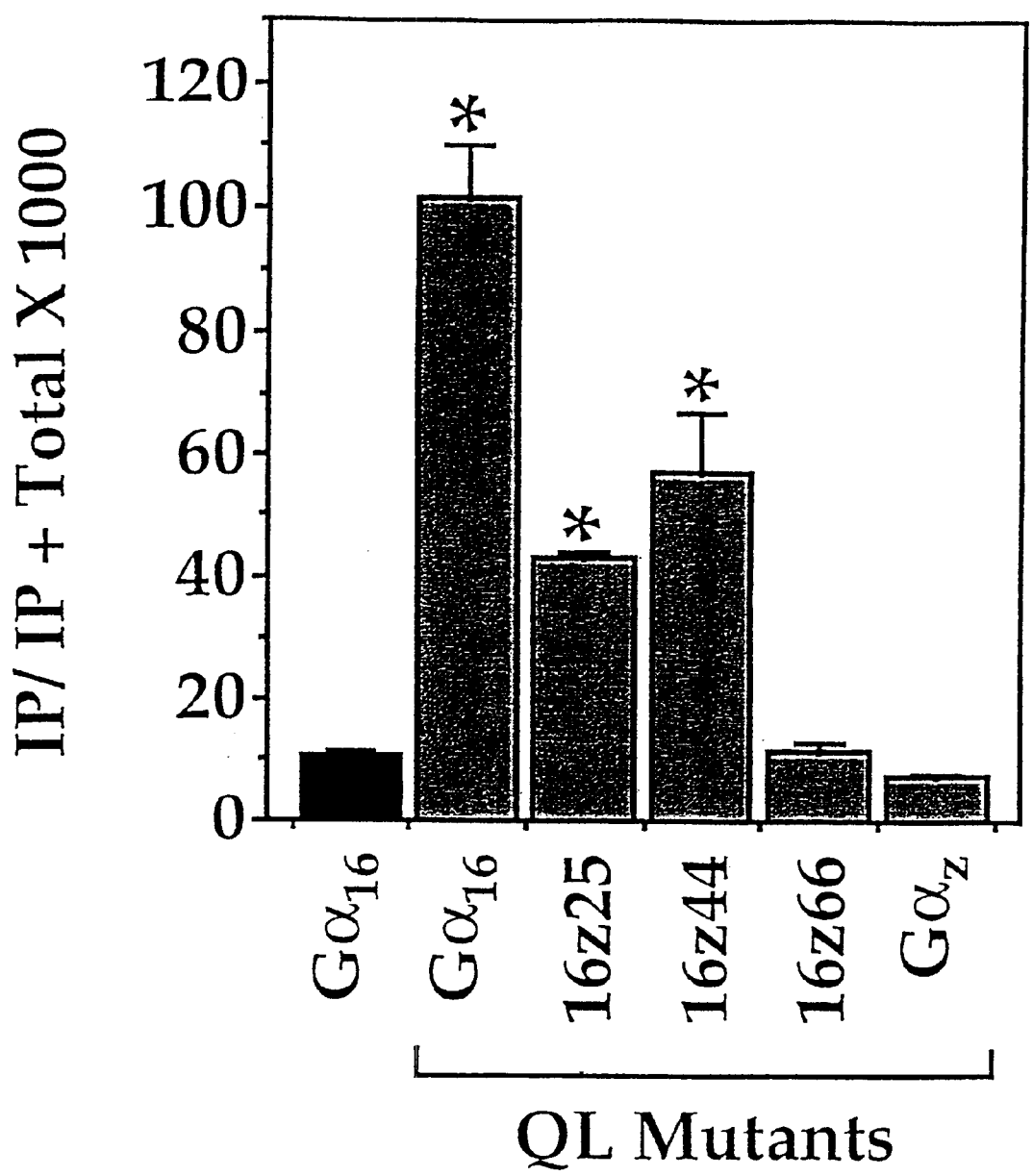
FIG. 6 shows constitutively activated $G\alpha_{16/z}$ chimeras stimulate PLC except for 16z66QL. Wildtype $G\alpha_{16}$ and $G\alpha_{16/z}$ chimeras were constitutively activated by altering the amino acid at position 212 from Q (Gln) to L (Leu). The cDNAs (0.25 µg/ml) encoding the mutant chimeras were transiently expressed in COS-7 cells. $G\alpha_{16}$ and $G\alpha_z$QL were included as negative controls. Transfected cells were labelled with [$^3$H]inositol and assayed for IP accumulation in the absence of agonist as in the legend to FIG. 4. *Basal IP formation was significantly higher than that obtained with wild-type $G\alpha_{16}$ Bonferroni t-test, P<0.05.

Because most of the $G\alpha_{16/z}$ chimeras contained $G\alpha_z$ C-terminal sequences, it was not possible to use commercially available $G\alpha_{16}$-specific C-terminal antiserum to verify the expression of these chimeras. Instead, a $G\alpha_z$-specific antiserum was used for the immunodetection of the 16z25, 16z44, and 16z66 chimeras. As shown in FIG. 5, all three chimeras were detected by the $G\alpha_z$-specific antiserum 3A-170 in membranes prepared from COS-7 cells transfected with the chimeras. However, both 16z3 and 16z6 contained insufficient $G\alpha_z$-sequence specificity to be detected by 3A-170. Thus, an alternative approach was taken to assess the functional expression of these chimeras by introducing an activating point mutation into the constructs. A mutation at codon 212 of $G\alpha_{16}$ has been shown to constitutively activate PLC in Swiss 3T3 cells (Qian, N. et al., 1994, supra). Expression of $G\alpha_{16}$QL (harboring the Q212L mutation) in COS-7 cells also led to increased basal accumulation of IP, while the expression of $G\alpha_{16}$ or $G\alpha_z$QL (Wong, Y. H. et al., 1992, supra) did not affect the PLC activity (FIG. 6). The constitutively active mutants of the $G\alpha_{16/z}$ chimeras were similarly expressed in COS-7 cells. Except for 16z66QL, all $G\alpha_{16/z}$ chimeras harboring the Q212L mutation constitutively stimulated PLC activity by a factor of 3–6 times the values obtained for their corresponding wild-type chimeras (FIG. 6). Although their constitutive activities were lower than that of $G\alpha_{16}$QL, the fact that 16z3QL and 16z6QL were functionally expressed in COS-7 cells suggested that their wild-type counterparts could also be expressed. The inability of 16z3 and 16z6 to transduce the DPDPE response may reflect a true incompatibility of these chimeras to associate with the δ-opioid receptor. The lack of constitutive activity of 16z66QL (FIG. 4) was not due to a deficiency in expression because 16z66QL was expressed to the same level as 16z25QL and 16z44QL.

Promiscuity of 16z25 and 16z44

The ability of 16z25 and 16z44 to interact productively with the δ-opioid receptor resulted in a further investigation into their capacity to functionally associate with other $G_i$- and $G_s$-coupled receptors. COS-7 cells were cotransfected with either 16z25 or 16z44 and a receptor (0.25 µg/ml per construct) chosen from a panel of $G_i$- or $G_s$-coupled receptors that were available in our laboratory. The selected receptors include the adenosine $A_1$, $\alpha_2$- and $\beta_2$-adrenergic, complement C5a, dopamine $D_1$ and $D_2$, formyl peptide (fMLP), luteinizing hormone, opioid receptor-like ($ORL_1$), prostanoid DP, vasopressin $V_2$, somatostatin-1 and -2 ($SSTR_1$ and SSTR2), three subtypes each of melatonin (1a, 1b and 1c) and opioid (µ, δ, and κ) receptors (Table 1). Transfected cells were assayed for IP formation in the absence or presence of saturating concentrations of the appropriate agonists. All fourteen $G_i$-coupled receptors examined were capable of activating 16z25 and elicit agonist-induced PLC activation (Table 1). The magnitude of PLC stimulation by the various receptors ranged from 1.5-fold to 4.5-fold. Activation of 16z25 by aminergic receptors (dopamine and melatonin receptors) resulted in up to 3.5-fold stimulation of PLC activity. The receptors for peptide ligands gave slightly higher responses in general. Similar results were obtained with the 16z44 chimera (Table 1). All of the $G_i$-coupled receptors tested were effeciently coupled to 16z44 and stimulated PLC. The 16z44-mediated PLC responses ranged from 1.7 to 5.5-fold stimulation. It should be noted that none of the $G_i$-coupled receptors, except SSTR2, was capable of stimulating IP production in the absence of 16z25 or 16z44 (Lee, J. W. M. et al., 1998, supra). Collectively, these results indicate that both 16z25 and 16z44 are capable of linking a large variety of $G_i$-coupled receptors to the stimulation of PLC. When $G_i$-coupled receptors such as the fMLP, melatonin Mel1a, and $ORL_1$ receptors were tested against the 16z3, 16z6, or 16z66 chimeras, no functional coupling could be detected.

As compared to $G\alpha_{16}$, the 16z25 and 16z44 chimeras exhibited an enhanced capability to interact with $G_i$-coupled receptors. Most notable was their ability to interact productively with the melatonin Mel1c receptor. Using a series of chimera melatonin receptors, it has been found that the bulky C-terminal tail of the melatonin Mel1c receptor may prohibit its coupling to $G\alpha_{16}$. Under experimental conditions identical to the present study, the Mel1c was unable to activate $G\alpha_{16}$ while both Mel1a and Mel1b receptors stimulated PLC via $G\alpha_{16}$. Other examples of enhanced linkage to $G_i$-coupled receptors by the 16z25 and 16z44 chimeras included the µ-opioid receptor and SSTR1. Amongst the three opioid receptor subtypes, activation of $G\alpha_{16}$ by the µ-opioid receptor is relatively weak (Lee, J. W. M. et al., 1998, supra). Both in terms of absolute activity and degree of stimulation, µ-opioid receptor-induced responses were more robust with the 16z25 and 16z44 chimeras (Table 1). As for SSTR1, 100 nM somatostatin stimulated IP formation by only 2-fold in COS-7 cells coexpressing $G\alpha_{16}$, while the same concentration of agonist elicited 3.5-fold of stimulation in cells coexpressing either 16z25 or 16z44 (Table 1).

Figure 7:
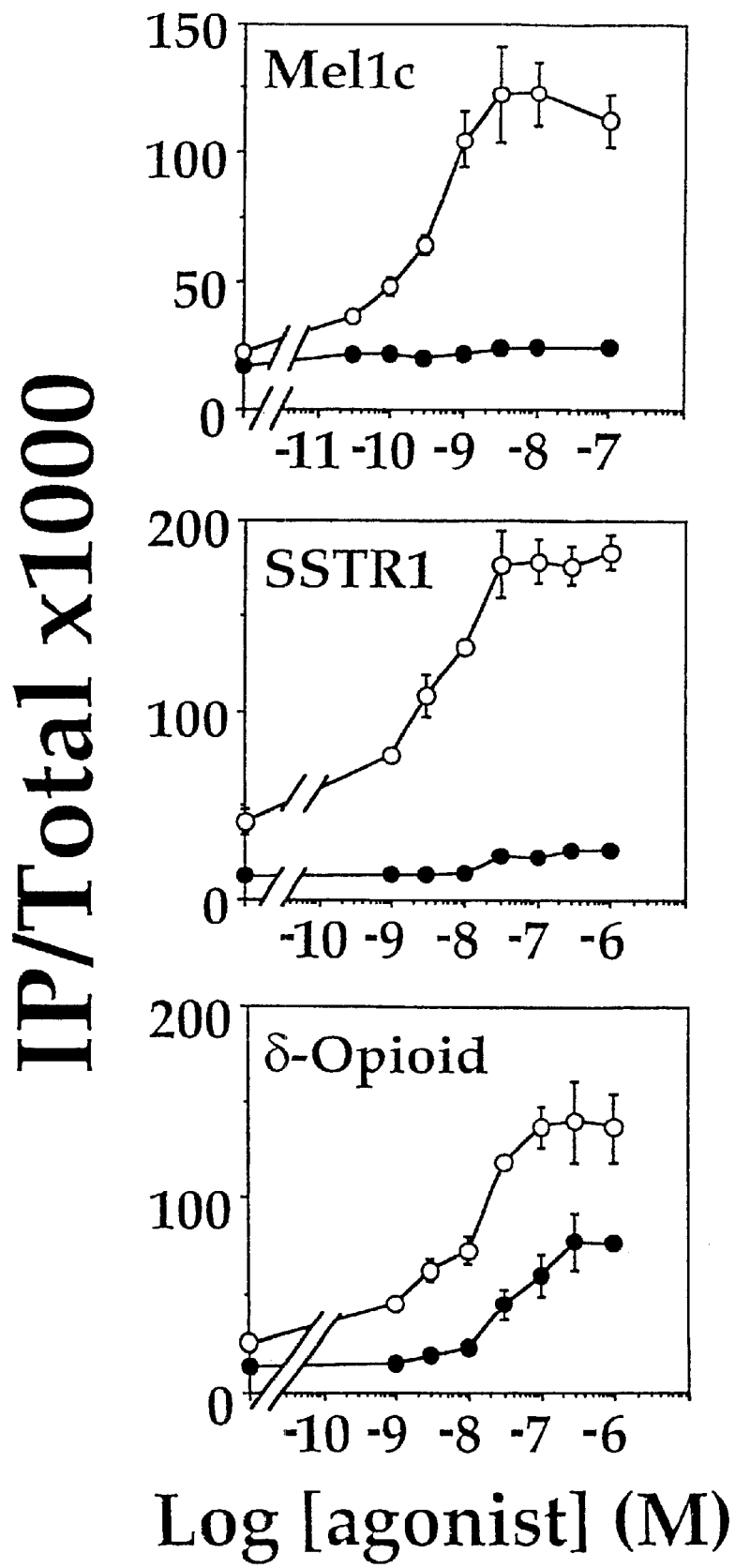
FIG. 7 shows dose-dependent agonist stimulation of PLC by the Mel1c, SSTR1, and δ-opioid receptors via $G\alpha_{16}$ or 16z44. COS-7 cells were transiently cotransfected with the cDNAs encoding $G\alpha_{16}$ (solid circles) or 16z44 (open circles) and one of the three selected receptors: Mel1c, SSTR1, or δ-opioid (at 0.25 µg/ml per construct). Transfected cells were then labelled with [$^3$H]inositol and assayed for IP formation in the absence or presence of various concentrations of 2-iodomelatonin (0.03–100 nM), somatostatin (1 nM to 1 µM), or DPDPE (1 nM to 1 µM).

As compared to $G\alpha_{16}$ or 16z25, the 16z44 chimera seemed to produce greater stimulations of PLC activity upon receptor activation (FIG. 4 and Table 1). The magnitudes of the agonist-induced responses mediated via 16z44 were generally higher than those obtained with $G\alpha_{16}$ or 16z25. Hence, the efficiency of coupling between 16z44 and several $G_i$-coupled receptors was examined. The melatonin Mel1c, SSTR1 and δ-opioid receptors were chosen on the basis of their varying abilities to associate with $G\alpha_{16}$. Each receptor was coexpressed with either $G\alpha_{16}$ or the 16z44 chimera in COS-7 cells and assayed for IP accumulation in response to increasing concentrations of the corresponding agonist. Activation of the melatonin Mel1c receptor by 2-iodomelatonin did not stimulate PLC activity in cells coexpressing the receptor and $G\alpha_{16}$ (FIG. 7). In the presence of 16z44, however, 2-iodomelatonin stimulated the formation of IP in a dose-dependent manner with an $EC_{50}$ of ~0.4 nM (FIG. 7). Likewise, the SSTR1 was weakly coupled to $G\alpha_{16}$ (FIG. 7 and in ref. 4) while it efficiently stimulated the PLC activity in the presence of 16z44 with an $EC_{50}$ of ~3 nM somatostatin (FIG. 7); the $EC_{50}$ of somatostatin for $G\alpha_{16}$ cotransfected cells was ~20 nM. The δ-opioid receptor has been shown to activate $G\alpha_{16}$ in a dose-dependent manner (Lee, J. W. M. et al., 1998, supra). Replacement of $G\alpha_{16}$ by the 16z44 chimera resulted in a more efficient stimulation of PLC by DPDPE (FIG. 7). The 16z44-mediated DPDPE response gave a higher maximal stimulation (twice that of the $G\alpha_{16}$-mediated response) and a reduced $EC_{50}$ (10 nM versus 40 nM). Taken together, these studies showed that the 16z44 chimera exhibited enhanced linkage to $G_i$-coupled receptors as compared to its parental $G\alpha_{16}$. Preliminary results suggest that such enhanced linkage can be extended to include the CCR1, CCR2b, and CCR5 chemokine receptors.

Coupling of 16z25 and 16z44 to $G_s$- and $G_q$-linked Receptors

A distinguishing feature of $G\alpha_{16}$ is its ability to link a large number of GPCR to the stimulation of PLC, including those receptors that normally utilize $G_s$ for signal propagation. To confirm that the $G\alpha_{16/z}$ chimeras can also recognize $G_s$-coupled receptors, we assessed the ability of 16z25 and 16z44 to interact productively with five different $G_s$-linked receptors. COS-7 cells were transiently cotransfected with either 16z25 or 16z44 and a $G_s$-coupled receptor ($\beta_2$-adrenergic, dopamine $D_1$, luteinizing hormone, prostanoid DP or vasopressin $V_2$). Transfected cells were subsequently challenged with the appropriate agonists. In cells coexpressing the $\beta_2$-adrenergic, dopamine $D_1$ or vasopressin $V_2$ receptors with either 16z25 or 16z44, activation of the receptor led to increased production of IP (Table 1). Among these three receptors, only the vasopressin $V_2$ receptor has the ability to utilize endogenous $G_q$ to weakly stimulate IP formation (66.5±17.8% over basal, n=6). The magnitudes of agonist-induced stimulations mediated via 16z25 or 16z44 were all around 3-fold above basal levels, and were generally lower than those observed with $G\alpha_{16}$ in previous reports (Offermanns, S. and Simon, M., 1995, supra; Lee, J. W. M. et al., 1998, supra). In contrast, activation of prostanoid DP or luteinizing hormone receptors did not significantly stimulate IP formation in the presence of either 16z25 or 16z44 (Table 1).

Inability of the prostanoid DP and luteinizing hormone receptors to interact with 16z25 and 16z44 was unlikely to be due to lack of receptor expression, because both receptors were functionally associated with stimulation of adenylyl cyclase in the transfectants (data not shown). Moreover, under identical experimental conditions, coexpression of luteinizing hormone receptor and $G\alpha_{16}$ allowed the transfected cells to produce a 3-fold stimulation of PLC in response to 1 μg/ml of human choriogonadotropin (Lee, J. W. M. et al., 1998, supra). The lack of coupling of 16z25 and 16z44 to the prostanoid DP and luteinizing hormone receptors suggest that even though these chimeras exhibited enhanced ability to recognize $G_i$-coupled receptors, their linkage to $G_s$-coupled receptors seemed to be impaired. The ability of 16z3, 16z6, and 16z66 to interact with the $G_s$-coupled $\beta_2$-adrenergic receptor was also examined. The $\beta_2$-adrenergic receptor was coexpressed with one of the three chimeras in COS-7 cells. None of these three chimeras were able to stimulate IP formation in response to 10 μM isoproterenol, despite the fact that the same concentration of agonist potently stimulated cAMP accumulation.

Productive coupling of $G\alpha_{16}$ to $G_q$-linked receptors usually leads to a potentiation of agonist-induced stimulation of PLC when $G\alpha_{16}$ is coexpressed (Offermanns, S. and Simon, M., 1995, supra). We adopted the same approach to examine the ability of 16z25 and 16z44 to recognize $G_q$-coupled receptors and selected the bombesin, $5HT_{1c}$, and muscarinic m1 receptors for the study. Each of the three $G_q$-coupled receptor was transiently expressed in COS-7 cells in the absence or presence of 16z44. Agonist-induced activation of these receptors significantly increased IP formation even in the absence of 16z44 (Table 2). Such stimulations were mediated through endogenous $G_{q/11}$ proteins. The magnitude of the agonist-induced responses increased by 35–55% in cells coexpressing the 16z44 chimera (Table 2). Similar results were obtained for the 16z25 chimera (data not shown). These studies demonstrated that both 16z25 and 16z44 chimeras retained the ability to interact with $G_q$-coupled receptors.

Construction and Characterisation of N-terminal $G\alpha_{z/16}$ Chimeras

Recent studies (Kostenis, E. et al., 1997, supra; Kostenis, E. et al., 1998, supra) have focused on the extreme N-terminal region of $G\alpha_q$ as a determinant for the selectivity of receptor coupling. As compared with the α subunits of the $G_i$ subfamily, $G\alpha_q$ and $G\alpha_{11}$ are longer by six residues at their N-termini. Progressive deletion or substitution with alanine of these N-terminal residues produced $G\alpha_q$ mutants that can effectively interact with $G_i$-coupled receptors (Kostenis E., et al., 1998, J. Biol. Chem., 273, 17886–17892). Alignment of the $G\alpha_{16}$ and $G\alpha_z$ sequences revealed that their predicted N-terminal a helices share little homology and the $G\alpha_{16}$ N-terminus is longer than that of $G\alpha_z$ by nine residues (FIG. 3). To assess whether the N-terminus of $G\alpha_z$ is required for efficient coupling to $G_i$-linked receptors, the entire αN helix was replaced with that of the first 30 residues of $G\alpha_z$. The resultant 30z16 chimera is shorter than $G\alpha_{16}$ by nine residues (FIG. 3).

Figure 8:
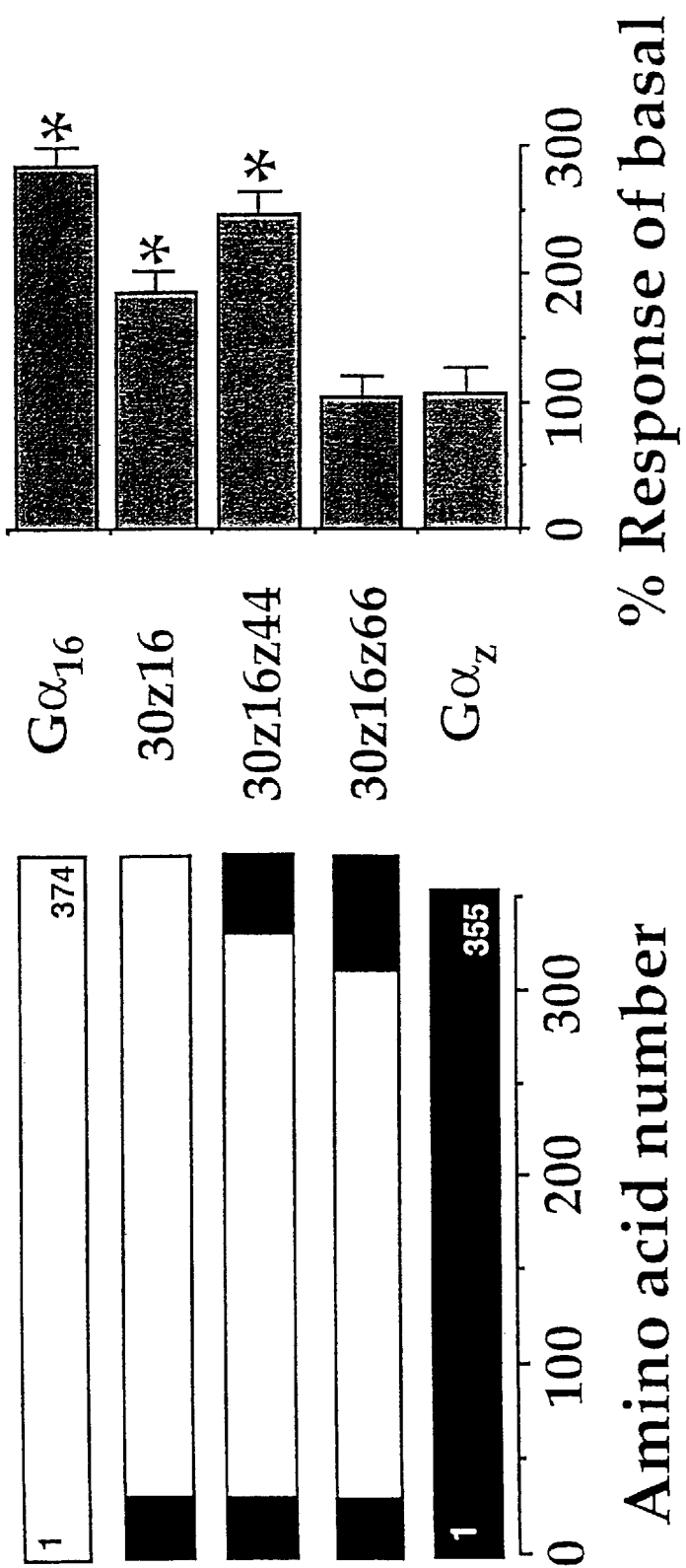
FIG. 8 shows stimulation of PLC by the δ-opioid receptor via the 30z16 and 30z16z44 chimeras. $G\alpha_{z/16}$ chimeras were constructed as described in Materials and Methods. Schematic representation of the chimeras are shown on the left. COS-7 cells were cotransfected with cDNAs (0.25 µg/ml each) encoding the δ-opioid receptor and $G\alpha_{16}$, $G\alpha_z$, or one of three $G\alpha_{z/16}$ chimeras: 30z16, 30z16z44, or 30z16z66. Transfected cells were assayed as in the legend to FIG. 4. Results are expressed as percentage stimulation of IP production as compared to basal activity. Basal values expressed as the ratio (×10$^3$) of IP to total inositols ranged from 6.55±0.52 to 9.24±0.43. *DPDPE-induced IP formation was significantly higher than basal levels; Bonferroni t-test, P<0.05.
Figure 9:
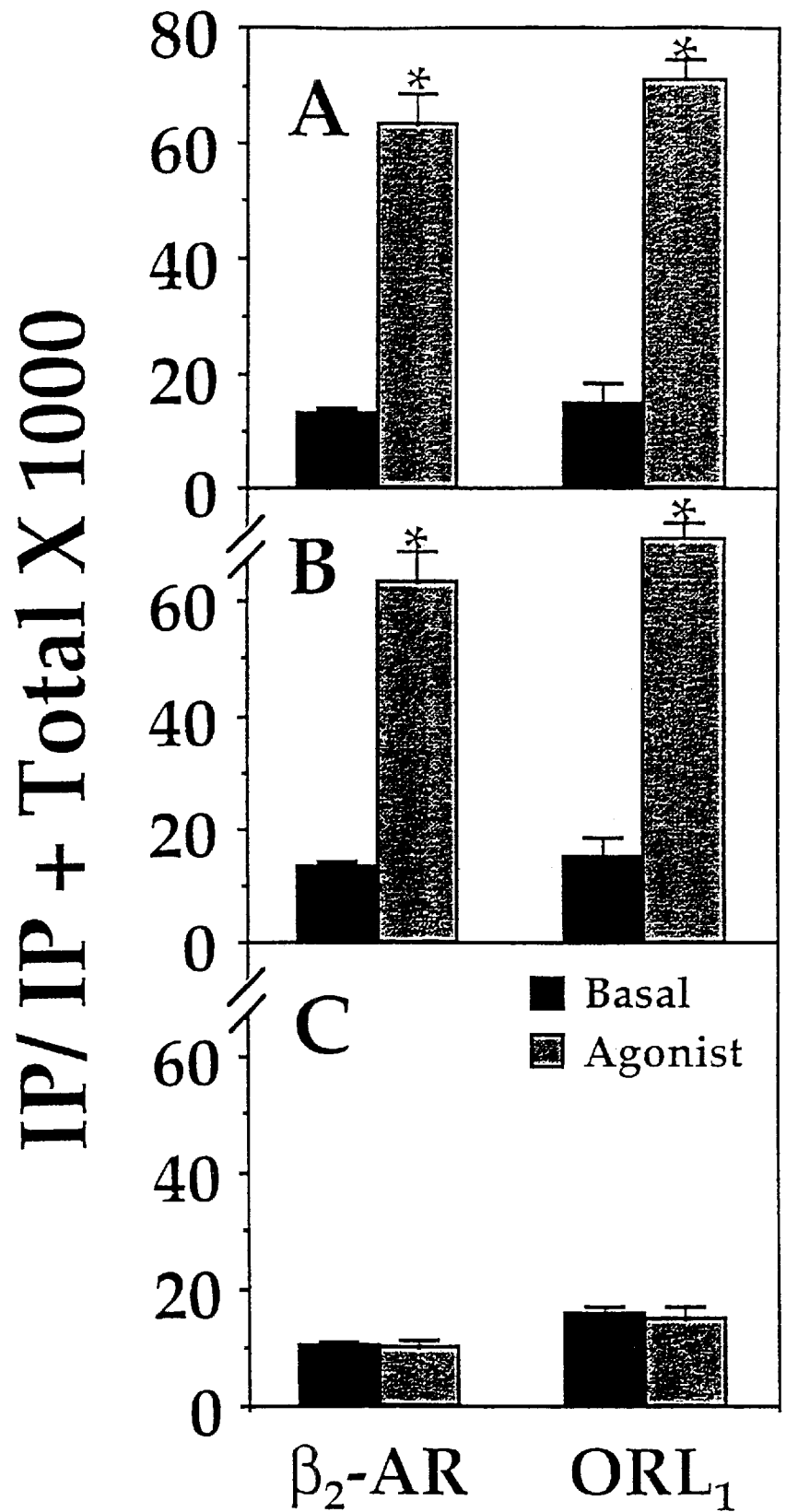
FIGS. 9A–9C show coupling of β$_2$-adrenergic and ORL$_1$ receptors to the 30z16 and 30z16z44 chimeras. COS-7 cells were cotransfected with cDNAs (0.25 µg/ml each) encoding the β$_2$-adrenergic or ORL1 receptor with one of three $G\alpha_{z/16}$ chimeras: 30z16 (A), 30z16z44 (B), or 30z16z66 (C). Transfected cells were assayed for IP formation in the absence or presence of agonist (1 µM isoproterenol or 100 nM nociceptin). *Agonist-induced IP formation was significantly higher than the corresponding basal values; Bonferroni t-test, P<0.05.

As with the $G\alpha_{16/z}$ C-terminal chimeras, the ability of the 30z16 chimera to interact with the δ-opioid receptor in COS-7 cells was tested. The δ-agonist, DPDPE, doubled the IP formation in COS-7 cells coexpressing the δ-opioid receptor and 30z16 (FIG. 8). The 30z16-mediated stimulation was lower than that obtained with $G\alpha_{16}$. Replacement of the αN helix of $G\alpha_{16}$ by the cognate region of $G\alpha_z$ seemed to impair the ability of the chimera to interact with the δ-opioid receptor. Additional experiments showed that 30z16 was also capable of transducing stimulatory signals from the $ORL_1$ and β2-adrenergic receptors to PLC (FIG. 9). However, GPCRs such as the melatonin Mel1c and μ-opioid receptors, which are weak or ineffective activators of $G\alpha_{16}$, could not stimulate PLC via 30z16 (data not shown). Although the 30z16 chimera could interact with both $G_i$- and $G_s$-coupled receptors, its promiscuity was compromised.

Figure 10:
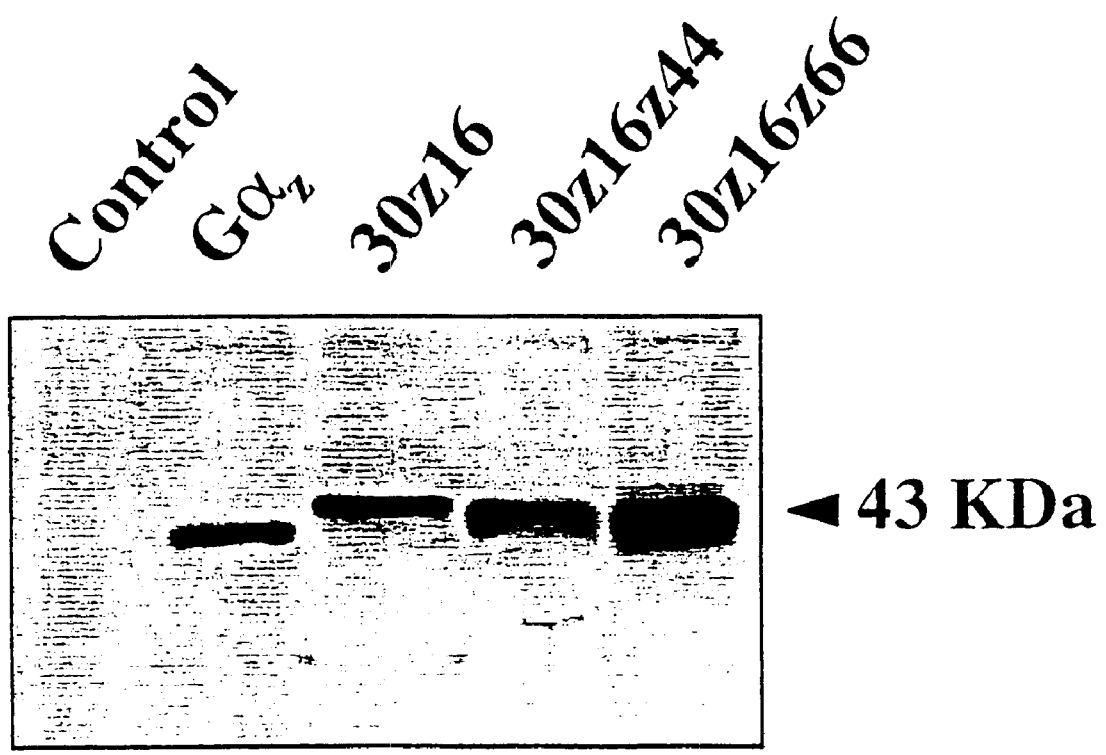
FIG. 10 shows immunodetection of chimera $G\alpha_{z/16}$ subunits. COS-7 cells were transiently transfected with cDNAs encoding the wild-type $G\alpha_z$, 30z16, 30z16z44, or 30z16z66 chimeras. Immunodetection of the various chimeras was performed as described in the legend to FIG. 5, except that a $G\alpha_z$ N-terminal specific antiserum 3–18 was used.

Because the N- and C-termini of the Gα subunit are in close proximity, the ability of $G\alpha_{16/z}$ chimeras to recognize $G_i$-coupled receptors may be enhanced by having $G\alpha_z$-specific sequences at both termini of the chimera. The 30z16z44 and 30z16z66 chimeras were constructed to determine whether the inclusion of a $G\alpha_z$-specific αN helix could enhance or rescue the ability of 16z44 and 16z66 to recognize $G_i$-coupled receptors. The 30z16z44 chimera behaved like $G\alpha_{16}$, while 30z16z66 remained unable to respond to agonist-activated δ-opioid receptor (FIG. 8). Results show that the 30z16z44 chimera was no more efficient than $G\alpha_{16}$ in coupling to the δ-opioid receptor, but was markedly better than the 30z16 chimera. The magnitude of DPDPE-induced PLC stimulation was actually lower with 30z16z44 than when it was mediated via 16z44 (cf. FIG. 4). Further experiments showed that the 30z16z44 chimera could interact productively with the $ORL_1$ and $\beta_2$-adrenergic receptors (FIG. 9), as well as the μ-opioid, κ-opioid and the three melatonin receptors (data not shown). The expression of 30z16, 30z16z44 and 30z16z66 was confirmed by immunoblot analysis using a $G\alpha_z$-specific N-terminal antiserum (FIG. 10). Thus, the inability of 30z16z66 to interact with GPCR was not due to a lack of expression. Overall, replacement of the αN helix of $G\alpha_{16}$ by $G\alpha_z$-specific sequence did not enhance the specificity of coupling to $G_i$-linked receptors.

Effects of Inverse Agonists on Receptors Coupled to 16z44

A notable feature of cells coexpressing a GPCR and 16z25 or 16z44 was their elevated basal IP production. The increased basal IP accumulation can be seen with the vast majority of the receptors tested (Table 1) and it resembles the constitutive activity of GPCRs. This interpretation is supported by the fact that no elevation of basal activities could be observed in COS-7 cells expressing 16z44 alone; coexpression with a $G_i$- or $G_s$-coupled receptor is required. If the enhanced linkage of the chimeras to GPCRs promotes the formation of constitutively active receptors, it may offer an opportunity to identify inverse agonists which act at various GPCRs. To test this hypothesis, COS-7 cells were cotransfected with cDNAs encoding 16z44 and either the δ-opioid or $\beta_2$-adrenergic receptor, and the ability of known inverse agonists to suppress the elevated basal IP levels of the transfectants was examined. As compared to cells coexpressing the δ-opioid receptor and $G\alpha_{16}$, 16z44 transfectants exhibited increased basal IP production (FIG. 9) but neither ICI-174,864 (an inverse agonist) nor naloxone (a neutral antagonist) affected the elevated basal levels. The expression of δ-opioid receptors in the transfectants was confirmed by the DPDPE-induced stimulation of PLC (FIG. 9). Similar results were obtained with cells coexpressing the $\beta_2$-adrenergic receptor and 16z44. Two inverse agonists of $p_2$-adrenergic receptor, ICI-118,551 and timolol, were incapable of reducing the elevated basal level associated with the coexpression of 16z44 (FIG. 9). These results suggest that although 16z44 may provide enhanced linkage to GPCRs, it does not necessarily promote the formation of constitutively active GPCRs.

DISCUSSION

Constituting one of the largest protein families found in nature, it is estimated that several thousand different GPCRs may exist in the human genome. The recent discovery of over 1,000 genes encoding known and orphan GPCRs in the *Caenorhabditis elegans* genome further supports this estimation. The molecular mechanism by which GPCRs select and activate different G proteins has not been fully discerned. The human $G\alpha_{16}$ possesses the rare ability to recognize a wide spectrum of GPCRs, and this property can facilitate the characterisation of orphan GPCRs. Numerous biochemical, structural, and molecular genetic studies have revealed that the docking site for receptors is composed of multiple regions on the $G\alpha$ subunit (reviewed in Bourne, H. R., 1997, Curr. Opin. Cell Biol., 9: 134–142). The five regions of the $G\alpha$ subunit believed to be involved in receptor recognition are the α2 helix, the β6-α5 loop, the α5 helix, and the two extreme termini. By replacing one or more of these regions in $G\alpha_{16}$ with sequences from $G\alpha_z$, chimera $G\alpha_{16/z}$ proteins that exhibit enhanced linkage to $G_i$-coupled receptors have been successfully created. Likewise, replacing one or more of these regions in $G\alpha_{16}$ with sequences from $G\alpha_s$, chimera $G\alpha_{16/s}$ proteins that exhibit enhanced linkage to $G_s$-coupled receptors have been successfully created (data not shown). With respect to the $G\alpha_{16/z}$ and $G\alpha_s$ chimeras, the 16z44 and 16s25 chimeras appeared to be particularly effective in these respects.

Since approximately 15% of the total number of $G_i$-coupled receptors examined to date can not activate $G_{16}$ (Kuang, Y. et al., 1996, supra; Wu, D. et al., 1992, supra), the molecular structure of $G\alpha_{16}$ may not be optimal for association to GPCRs with a high preference for $G_i$ proteins. This is perhaps unavoidable if $G\alpha_{16}$ were to possess the ability to recognize $G_q$- and $G_s$-coupled receptors as well. A previous study utilizing chimeras between $G\alpha_{16}$ and $G\alpha_{i1}$ has shown that multiple regions of $G\alpha_{16}$ are required for coupling to the $G_i$-linked C5a receptor (Lee, C. H. et al., 1995, supra). However, there are no well defined "specificity regions for $G_i$-coupled receptors" on $G\alpha_{16}$. The present experiments involved the alteration of the extreme N- and C-termini of $G\alpha16$ in an attempt to improve the specificity of coupling to $G_i$-linked receptors. Of the various chimeras constructed in this study, 16z25 and 16z44 can indeed recognize more $G_i$-coupled receptors than the wild-type $G\alpha_{16}$.

Unlike $G\alpha_q$, substitution of the last few residues of $G\alpha_{16}$ with $G\alpha_z$ sequence did not produce any enhancement of receptor recognition. On the contrary, 16z3 and 16z6 were incapable of mediating receptor-induced stimulation of PLC. Surprisingly, minor changes in the C-terminus of $G\alpha_{16}$ completely abolished its ability to interact with GPCR. The 16z3 chimera differed from $G\alpha_{16}$ by only two residues at the −1 and −3 positions. Given that the last five residues of $G\alpha_z$ have been shown to confer upon $G\alpha_q$ and $G\alpha_{12}$ the ability to recognize $G_i$-coupled receptors, it is difficult to comprehend the present finding. Notably, both 16z25 and 16z44 contained the same substitution as 16z3 and 16z6 at their extreme C-termini but they were fully capable of interacting with a large panel of GPCRs. However, it is not possible to entirely exclude the possibility that 16z3 and 16z6 were not expressed sufficiently to associate with receptors.

Figure 2:
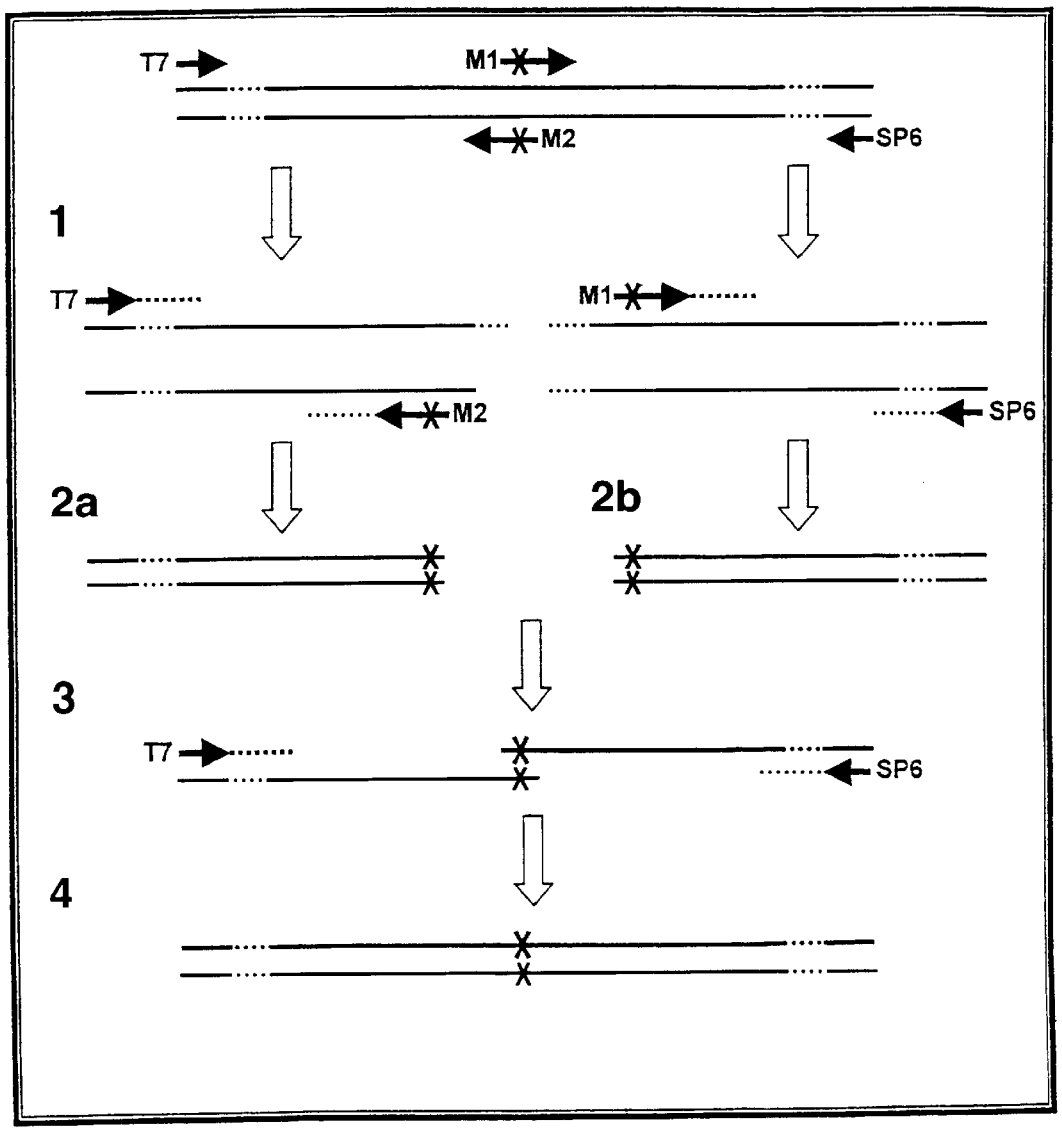
FIG. 2 shows an illustration of the polymerase chain reaction-mediated site-directed mutagenesis methodology. M1 and M2 represent two sequence-specific primers bearing the desired mutations (cross marks). T7 and SP6 are two terminal primers flanking the cDNA (T7 and SP6 are specific sequences found in the expression vector pcDNAI). Sense and antisense strands of the DNA template are indicated as the black and light gray horizontal lines. Step 1 is the annealing of primers with template cDNA. Step 2a is the amplification of the N-terminal portion. Step 2b is the amplification of the C-terminal portion. Step 3 is the annealing of the half products and the terminal primers. Step 5 is amplification of the full-length cDNA.
Figure 11:
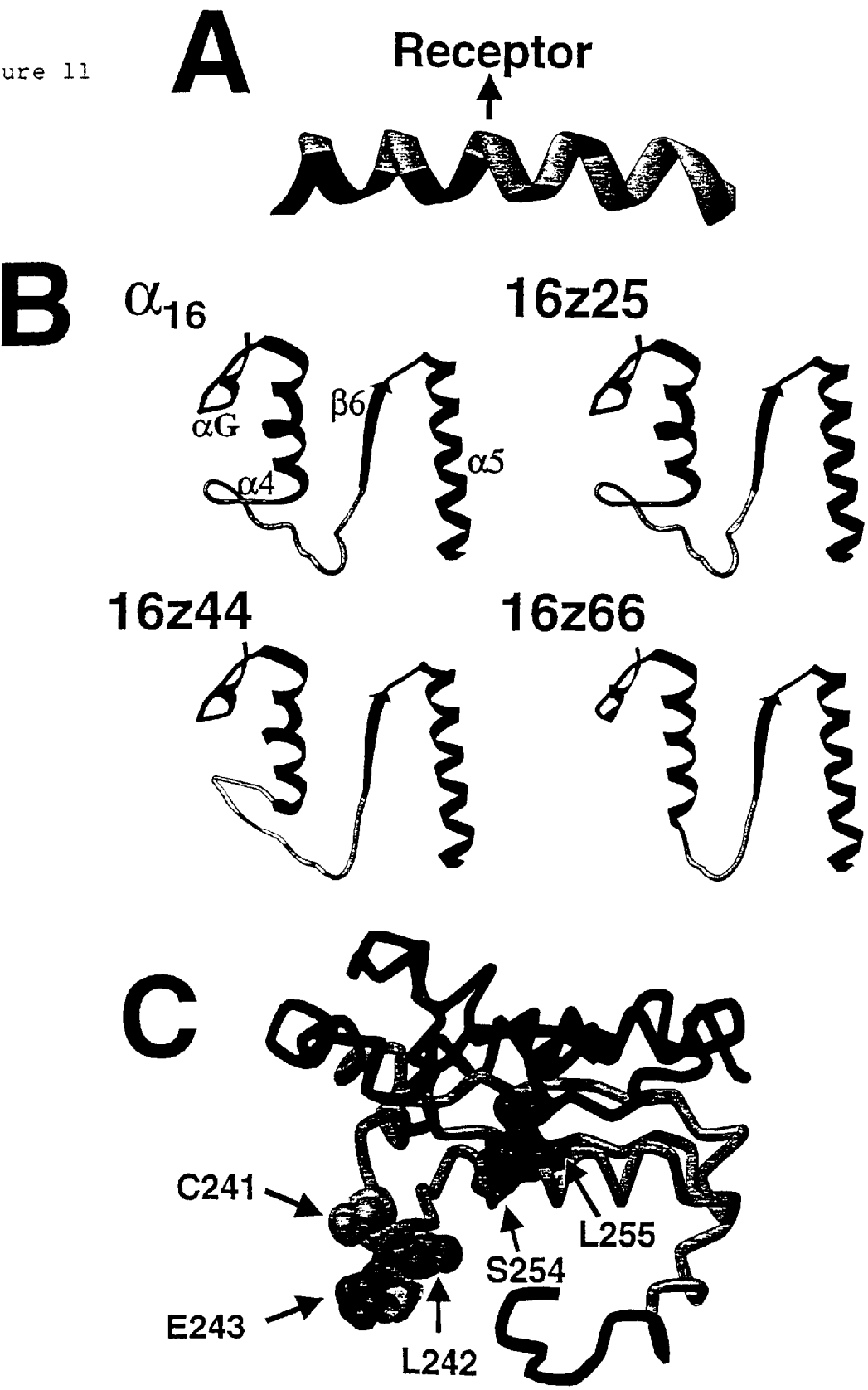
FIGS. 11A–C show molecular models of $G\alpha_{16/z}$ chimeras. Coordinates of the hypothetical structural models of various Gα subunits were generated by Swiss-Model modeling service available from the Swiss-Model website using $G\alpha_{t1}$ and $G\alpha_{i1}$ complexed with βγ subunits as template structures (coordinate codes 1GOT and 1GP2; obtained from the Protein Data Bank of Brookhaven National Laboratory. Models were visualized by Swiss-PDB Viewer v3.1 and rendered by POV-Ray for Windows v3.1. A, The α5 helix of $G\alpha_{16}$ is shown with the putative receptor-facing side on top. The last 7 residues have not been mapped to the structure due to the lack of the corresponding residues in the template. Light gray patches correspond to the residues different from $G\alpha_z$ in their nature. B, The structures from αG to α5 of 16z25, 16z44 and 16z66 are displayed. Receptor-facing side of α5 helix is inside the plane. The α4/β6 loops of 16z25 and 16z44 are longer than that of the template structures and thus are not in well-defined structures. C, The GTPase domain of $G\alpha_{16}$ is in the same orientation as in B. The putative PLC-activating domain is marked in light gray according to the study of Medina et al (1996) and the 5 residues important for PLC activation are shown in balls (Venkatakrishnan and Exton, 1996).

As compared to $G\alpha_{16}$, the 16z25 chimera can additionally couple to the melatonin Mel1c receptor and produce higher magnitudes of PLC stimulation with some of the $G_i$-coupled receptors (e.g., μ-opioid and SSTR1). In the 16z25 chimera, the α5 helix of $G\alpha_{16}$ was replaced by that of $G\alpha_z$. Various studies have demonstrated the functioning of the α5 helix in receptor coupling. Amino acids within the α5 helix of $G\alpha_s$ (Conklin, B. R. et al., 1996, supra; Sullivan K. A. et al., 1987, supra), $G\alpha_t$ (Tsu, R. C. et al., 1997, supra), $G\alpha_{i1}$ (Martin, E. L. et al., 1996, J. Biol. Chem., 271: 361–366), and $G\alpha_q$ (Conklin, B. R. et al., 1993, 1996, supra) have been shown to alter the specificity of receptor coupling. The α5 helix of $G\alpha_z$ is quite different from that of $G\alpha_{16}$ with less than 35% homology (FIGS. 2 and 3). Alignment of the α5 helices of $G\alpha_{16}$ and $G\alpha_z$ shows that, starting from position −1 (Leu$^{374}$ of $G\alpha_{16}$ and Cys$^{355}$ of $G\alpha_z$), every third or fourth amino acids are different between the two $G\alpha$ subunits. If these residues were to lie along one plane on the α5 helix, they may provide different contact surfaces for GPCRs. Using the crystal structures of $G\alpha_{t1}$ and $G\alpha_{i1}$ as template structures, we generated a molecular model to highlight the structural differences in the α5 helices of $G\alpha_{16}$ and $G\alpha_z$ (FIG. 11A). When the $G\alpha_z$-specific amino acids are superimposed on the α5 helix of $G\alpha_{16}$, the receptor-facing plane are predominantly composed of $G\alpha_z$-specific residues. Moreover, the majority of amino acid differences are concentrated in the distal two-thirds of the α5 helix. Interestingly, the same region has been proposed to constitute the interface for receptors based on evolutionary trace analysis of the $G\alpha$ subunits (Lichtarge, O. et al., 1996, PNAS USA 93: 7507–1711).

Like 16z25, the 16z44 chimera has an expanded capability to interact with $G_i$-coupled receptors. Moreover, these studies show that several chemokine receptors can stimulate PLC in cells coexpressing the 16z44 chimera, despite their inability to activate $G\alpha_{16}$. Not only did 16z44 recognize more $G_i$-coupled receptors than $G\alpha_{16}$, but the magnitudes of the stimulations were also greater. Comparison of the $EC_{50}$ values obtained with 16z44 and $G\alpha_{16}$ transfectants reflected that 16z44 was more efficient in linking the $G_i$-coupled receptors to the activation of PLC. Another notable feature of 16z44 is its elevated basal activities. Cells coexpressing 16z44 generally exhibited basal PLC activities that were much higher than those coexpressing $G\alpha_{16}$ (Table 1). This elevation in basal IP accumulation resembles the constitutive activity of GPCRs. If 16z44 couples tightly to the $G_i$-linked receptors, stable receptor-16z44 complexes may facilitate the formation of spontaneously active receptors that will then produce higher basal PLC activities. This interpretation is supported by the fact that no elevation of basal activities could be observed in COS-7 cells expressing 16z44 alone; coexpression with a $G_i$- or $G_s$-coupled receptor is required. As a result of elevated basal activities, 16z44-mediated stimulations of PLC were not significantly better than those mediated by $G\alpha_{16}$ when expressed as a percentage of the basal activity. However, the absolute levels of IP accumulation transduced by 16z44 were always greater than those of $G\alpha_{16}$. Basal IP accumulation was also higher in cells coexpressing the 16z25 chimera, albeit to a lesser extent. As reflected by the absolute amount of IP formation, 16z25 was generally less efficient than 16z44 in transducing signals from $G_i$-coupled receptors.

Structural differences between 16z25 and 16z44 are primarily located in the α4/β6 loop (residues 318–335 of $G\alpha_{16}$). The α4/β6 loop is one of several secondary structures forming the contact surface for receptors (part of the A1 cluster as described by Lichtarge, O. et al., 1996, supra). The α4 helix and α4/β6 loop region of $G\alpha_{i1}$ are important for specific recognition of receptors (Bae, H. et al., 1997, J. Biol. Chem., 272: 32071–32077). The α4/β6 loop of 16z25 is identical to that of $G\alpha_{16}$ because there is no substitution of $G\alpha_z$-specific residues in this region of 16z25 (FIG. 3). Based on the crystal structure coordinates of trimeric $G_{t1}$ (Lambright, D. G. et al., 1996, supra) and $G_{i1}$ (Wall, M. A. et al., 1995, supra), the α4/β6 loop of 16z44 is predicted to be a more flexible structure with an energy level higher than those of 16z25 and $G\alpha_{16}$ (FIG. 11B). This increased flexibility may partially account for the enhanced potency of 16z44 to transduce signals from $G_i$-coupled receptors. The model generated for 16z66 (FIG. 11B) fitted well to the known structures of $G\alpha_{t1}$ and $G\alpha_{i1}$. As compared to $G\alpha_{16}$, 16z66 has a smaller α4/β6 loop and a tighter α4 helix. One would presume the close resemblance of 16z66 to $G\alpha_{t1}$ and $G\alpha_{i1}$ implies enhanced capability of the chimera to interact with $G_i$-coupled receptors, yet our results were contrary to such a prediction.

Since 16z66 was expressed to the same extent as the other chimeras, its inability to mediate receptor-induced stimulation of PLC might be due to the disruption of effector recognition domains like the α4/β6 region. The α4 and the α4/β6 loop of $G\alpha_q$ are known to be involved in the activation of PLC (Arkinstall, S. et al., 1995, FEBSLett., 364: 45–50; Medina, R. et al., 1996, J. Biol. Chem., 271: 24720–24727). When the putative PLC regulatory domains of $G\alpha_q$ are mapped onto a molecular model of $G\alpha_{16}$ (shown in blue, FIG. 11C), these regions were not substituted by $G\alpha_z$-specific residues in 16z66. Several residues around the switch III region of $G\alpha_q$ have also been shown to be critical for the regulation of PLC (Venkatakrishnan, G. and Exton, J. H., 1996, J. Biol. Chem., 271: 5066–5072), and they are conserved in $G\alpha_{16}$; residues 241–243 and 254–255 (FIG. 11C). We used molecular modeling of $G\alpha_{16}$ to identify amino acids distal to or in the α4 helix that may interact with these PLC-activating residues. Residue $Leu^{254}$ is predicted to interact with several amino acids in the α4 helix ($Ile^{312}$, $Met^{315}$, $Tyr^{316}$, and $Thr^{317}$) and the α4/β6 loop ($Asp^{325}$). Four out of these five potential sites (except $Ile^{312}$) were actually replaced by $G\alpha_z$-specific residues in 16z66 (FIG. 3). Like mutating $Leu^{254}$ itself, the disruption of intramolecular interactions may severely curtail the ability of 16z66 to stimulate PLC, resulting in a lack of constitutive activity of 16z66QL. Another possibility is that 16z66 can not adopt the GTP-bound active form. Further experiments are needed to distinguish the molecular basis for the lack of function of 16z66.

Although an extensive study was not made to determine the importance of N-terminal sequences of $G\alpha_z$ in receptor recognition, the present study shows that the αN helix of $G\alpha_z$ alone could not confer specificity for $G_i$-coupled receptors. This is in stark contrast to results obtained in similar studies where the N-terminus of $G\alpha_z$ alone was sufficient to allow a $G\alpha_{z/t1}$ chimera to respond to the δ-opioid receptor (Tsu, R. C. et al., 1997, supra). Close proximity of the two termini in the crystal structures of $G\alpha_{t1}$ (Lambright et al., 1996, Nature, 379, 311–319) and $G\alpha_{i1}$ (Wall et al., 1995, Cell, 83, 1047–1058) supports the involvement of the N-terminus in receptor recognition. Biochemical evidence are also available to substantiate this notion for the coupling of receptors to $G\alpha_o$ (Denker et al., 1995, Biochemistry, 34, 5544–5553) and $G\alpha_{t1}$ (Dratz et al., 1993, Nature, 363, 276–281), two members of the $G_i$ subfamily. Hence, an intact N-terminus may be required for $G\alpha_{16}$ to efficiently associate with GPCRs. In this respect, results given here are in accordance with those reported by Lee and co-workers (Lee et al., 1995, Mol. Pharmacol, 47, 218–223), where the N-terminal 209 residues of $G\alpha_{16}$ were found to be essential for activation by the $G_i$-coupled C5a receptor.

Despite their enhanced linkage to $G_i$-coupled receptors, neither 16z25 nor 16z44 can be considered as a universal adapter for GPCRs. As compared to $G\alpha_{16}$, the ability of 16z25 and 16z44 to recognize the luteinizing hormone receptor was actually diminished. Naturally, one would expect that when the specificity for $G_i$-coupled receptors increases in a $G\alpha$ subunit, its specificity for $G_s$-linked receptors will be inversely affected because the two sets of GPCRs are designed to produce opposite effects on adenylyl cyclase. Perhaps it is impractical to engineer a universal G protein adapter for GPCRs even though such a construct is highly desirable for the characterisation of orphan receptors. Nonetheless, the present invention shows the improvement of recognition of specific subsets of GPCRs by altering receptor contact regions on $G\alpha_{16}$. With the recent explosion in the number of orphan receptors being cloned, the chimeras described herein may be invaluable tools for their characterisation. For example, the 16z44 chimera can be incorporated into a variety of cell-based assays for the rapid detection of receptor activation. Furthermore, the ability of $G\alpha_{16}$ to recognize $G_s$-coupled receptors can be similarly enhanced by incorporating $G\alpha_s$-specific regions on a $G\alpha_{16}$ backbone. Several chimeric $G\alpha_{16}$ with expanded capability of receptor recognition may collectively serve as a true "universal adapter" for orphan GPCRS.

Table Legends:

Table 1: Coupling of $G\alpha_{16}$, 16z25 and 16z44 to various $G_i$- or $G_s$-coupled receptors. COS-7 cell were cotransfected with cDNAs encoding 16z25 or 16z44 and the indicated receptors (0.25 μg/ml per construct). Transfected cells were labeled with 2.5 μCi/ml [$^3$H]inositol 20–24 hours prior to assay. IP formations were determined in the absence (basal) or presence of specific agonists for the indicated receptors. DAGO, [D-Ala$^2$,N-Me-Phe$^4$,Gly$^5$-ol]enkephalin; DPDPE, [D-Pen$^2$,D-Pen$^5$]enkephalin; fMLP, N-formylmethionyl-leucyl-phenylalanine; hCG, human choriogonadotropin; LHR, luteinizing hormone receptor; PIA, (+)-N$^6$-(2-phenylisopropyl)-adenosine. N.D., not determined. *Agonist treatments significantly increased IP formation over basal levels; Bonferroni t-test, p<0.05. $^a$ Data were extracted from Lee et al. 1998, supra.

Table 2: COS-7 cells were cotransfected with cDNAs encoding one of the three receptors indicated, with or without (control) 16z44 (0.25 μg/ml per construct). Transfected cells were labeled with [$^3$H]inositol (2.5 μCi/ml) 20–24 hours prior to assay. IP formations were determined in the absence (basal) or presence of specific agonists for the indicated receptors. Agonists used were 100 nM bombesin, 1 μM serotonin, and 200 μM carbachol. Data represent the mean±S.D. of triplicate determinations of a single representative experiment; two additional experiments yielded similar results. *Agonist treatments significantly increased IP formation over basal levels. **Agonist-induced responses mediated via 16z44 were significantly greater than those mediated via endogenous Gq/11 proteins; Bonferroni t-test, P<0.05.

|  |  | IP Formation | | | | | | | | |
| --- | --- | --- | --- | --- | --- | --- | --- | --- | --- | --- |
|  |  | $G_\alpha 16$ | | | 16z25 chimera | | | 16z44 chimera | | |
| Receptor | Ligand | Basal | Agonist | % Res. | Basal | Agonist | % Res. | Basal | Agonist | % Res. |
| $G_i$-coupled | | | | | | | | | | |
| Adenosine $A_1$ | 10 μM PIA | 11.7 ± 0.9 | 90.3 ± 11.4* | 766a | 30.3 ± 1.4 | 59.7 ± 5.3* | 197 | 49.9 ± 3.2 | 93.9 ± 7.8* | 188 |
| $\alpha_2$-adrenergic | 1 μM UK14,304 | 14.7 ± 1.6 | 107.4 ± 9.6* | 730 | 31.8 ± 2.5 | 116.1 ± 8.8* | 365 | 42.6 ± 0.9 | 126.7 ± 1.5* | 297 |
| C5a | 100 nM C5a | 11.1 ± 1.2 | 67.5 ± 8.1* | 608 | 18.4 ± 3.0 | 79.6 ± 6.5* | 432 | 19.1 ± 1.1 | 87.4 ± 7.2* | 457 |
| Dopamine $D_2$ | 10 μM dopamine | 11.6 ± 1.5 | 24.0 ± 2.3* | 207a | 12.3 ± 0.9 | 40.1 ± 0.9* | 324 | 28.0 ± 3.4 | 84.5 ± 6.2* | 302 |
| fMLP | 200 nM fMLP | 12.1 ± 0.9 | 68.6 ± 5.4* | 566 | 16.6 ± 2.5 | 58.4 ± 5.1* | 352 | 21.4 ± 1.6 | 91.6 ± 7.2* | 428 |
| Melatonin MelIa | 1 μM 2-iodomelatonin | 15.4 ± 1.2 | 45.6 ± 6.0* | 296 | 53.4 ± 2.9 | 80.4 ± 4.0* | 150 | 53.7 ± 5.8 | 91.9 ± 8.8* | 171 |
| Melatonin MelIb | 1 μM 2-iodomelatonin | 16.2 ± 2.6 | 31.7 ± 2.3* | 195 | 69.7 ± 3.8 | 108.3 ± 3.6* | 155 | 63.6 ± 2.0 | 113.2 ± 7.3* | 177 |
| Melatonin MelIc | 1 μM 2-iodomelatonin | 13.9 ± 1.4 | 16.1 ± 3.7 | 115 | 15.7 ± 1.3 | 42.5 ± 6.7* | 270 | 28.2 ± 3.0 | 86.8 ± 7.0* | 307 |
| δ-opioid | 100 nM DPDPE | 10.1 ± 1.5 | 42.2 ± 6.1* | 417 | 23.2 ± 4.1 | 66.8 ± 7.1* | 287 | 22.2 ± 1.4 | 121.8 ± 9.1* | 548 |
| κ-opiod | 100 nM U50,488 | 10.3 ± 2.6 | 33.7 ± 3.4* | 327 | 23.5 ± 3.6 | 44.2 ± 3.6* | 188 | 27.3 ± 3.8 | 70.3 ± 5.2* | 257 |
| μ-opioid | 100 nM DAGO | 11.9 ± 1.5 | 16.0 ± 0.8* | 134 | 32.9 ± 2.0 | 74.0 ± 3.7* | 224 | 25.4 ± 4.6 | 68.5 ± 8.7* | 269 |
| ORL1 | 100 nM nociceptin/OFQ | 10.2 ± 1.3 | 64.1 ± 8.7* | 628 | 18.2 ± 1.1 | 74.3 ± 6.7* | 408 | 29.3 ± 0.5 | 111.5 ± 10.8* | 380 |
| SSTR1 | 100 nM somatostatin | 12.6 ± 1.6 | 24.2 ± 2.6* | 198a | 17.5 ± 0.2 | 60.7 ± 7.4* | 347 | 32.7 ± 1.8 | 121.8 ± 4.0* | 372 |
| SSTR2 | 100 nM somatostatin | 16.5 ± 2.5 | 106.4 ± 10.8* | 645a | 13.3 ± 1.3 | 62.2 ± 5.5* | 467 | 36.6 ± 0.4 | 169.1 ± 5.5* | 462 |
| $G_s$-coupled | | | | | | | | | | |
| $\beta_2$-adrenergic | 10 μM isoproterenol | 16.1 ± 1.5 | 127.0 ± 5.9* | 784a | 15.5 ± 2.1 | 55.9 ± 5.0* | 360 | 30.6 ± 0.4 | 94.2 ± 5.8* | 307 |
| Dopamine $D_1$ | 10 μM dopamine | 10.8 ± 1.7 | 98.3 ± 8.1* | 904a | 16.3 ± 3.4 | 34.9 ± 0.3* | 214 | 32.7 ± 0.8 | 94.0 ± 2.2* | 287 |
| LHR | 1 μg/ml hCG | 10.2 ± 1.1 | 30.6 ± 1.2* | 300a | 13.7 ± 0.3 | 16.1 ± 0.8 | 117 | 19.3 ± 0.3 | 22.7 ± 1.9 | 117 |
| Vasopressin V2 | 100 nM vasopressin | 11.8 ± 1.0 | 39.2 ± 1.5* | 332 | 14.5 ± 1.6 | 42.2 ± 2.5* | 291 | 18.6 ± 1.2 | 59.8 ± 4.9* | 321 |

TABLE 2

| | IP Formation | | | | |
| --- | --- | --- | --- | --- | --- |
| | Control | | 16z44 chimera | | Enhance- |
| Receptor | Basal | Agonist | Basal | Agonist | ment |
| Bombesin | 7.6 ± 0.2 | 148.9 ± 4.8* | 41.1 ± 0.5 | 233.9 ± 11.1* | 57% |
| 5-HT$_{1C}$ | 26.0 ± 2.2 | 145.9 ± 8.5* | 87.0 ± 0.9 | 208.6 ± 9.6* | 43% |
| Muscarinic m1 | 20.3 ± 1.9 | 182.8 ± 1.1* | 77.3 ± 4.9 | 245.0 ± 0.3* | 34% |

TABLE 3

| Chimera | Primers | SEQ ID NO | Priming regions | Templates |
| --- | --- | --- | --- | --- |
| 16z3 | T7 + GCGCTCTAGAGTtca GCAAAGGCCGATCTCGTCCAG | 110 | Gα$_{16}$(1102–1113) + Gα$_z$(1057–1065) | Gα$_{16}$-pcDNAI |
| 16z7 | 5': T7 + GCCAATGTACTTGAGGTAGCGGGCGAGCAC<br>3': GTGCTCGCCCGCTACCTCAAGTACATTGGC + SP6 | 111<br>112 | Gα$_{16}$(1087–1101) + Gα$_z$(1045–1059) | 5': Gα$_{16}$-pcDNAI<br>3': Gα$_z$-pcDNAI |
| 16z25 | 5': T7 + GATGTTACTGGTGTCTGTGGCACATGTGTAGTG<br>3': CACTACACATGTGCCACAGACACCAGTAACATC + SP6 | 94<br>93 | Gα$_{16}$(1029–1041) + Gα$_z$(985–999) | 5': Gα$_{16}$-pcDNAI<br>3': Gα$_z$-pcDNAI |

TABLE 3-continued

| Chimera | Primers | SEQ ID NO | Priming regions | Templates |
|---|---|---|---|---|
| 16z44 | 5': T7 + CTCCTTGTTTCGGTTGCTGCCCTCGGGGCC | 95 | $G\alpha_{16}$(976–990) | 5': $G\alpha_{16}$-pcDNAI |
| | 3': GGCCCCGAGGGCAGCAACCGAAACAAGGAG + SP6 | 96 | + $G\alpha_z$(934–948) | 3': $G\alpha_z$-pcDNAI |
| 16z66 | 5': T7 + CTGACCCTTGTACTCGGGGAAATAGGTAGC | 98 | $G\alpha_{16}$(874–888) | 5': $G\alpha_{16}$-pcDNAI |
| | 3': GCTACCTATTTCCCCGAGTACAAGGGTCAG + SP6 | 97 | + $G\alpha_z$(868–882) | 3': $G\alpha_z$-pcDNAI |
| 30z16 | 5': T7 + CTTCAGCTCCCCGCGCTGCCGCTGGCTCTC | 100 | $G\alpha_z$(76–90) | 5': $G\alpha_z$-pcDNAI |
| | 3': GAGAGCCAGCGGCAGCGCGGGGAGCTGAAG + SP6 | 99 | + $G\alpha_{16}$(118–131) | 3': $G\alpha_{16}$-pcDNAI |
| 30z16z44 | 5': T7 + CTTCAGCTCCCCGCGCTGCCGCTGGCTCTC | 113 | $G\alpha_z$(76–90) | 5': $G\alpha_z$-pcDNAI |
| | 3': GAGAGCCAGCGGCAGCGCGGGGAGCTGAAG + SP6 | 114 | + $G\alpha_{16}$(118–131) | 3': 16z44-pcDNA3 |
| 30z16z66 | 5': T7 + CTTCAGCTCCCCGCGCTGCCGCTGGCTCTC | 115 | $G\alpha_z$(76–90) | 5': $G\alpha_z$-pcDNAI |
| | 3': GAGAGCCAGCGGCAGCGCGGGGAGCTGAAG + SP6 | 116 | + $G\alpha_{16}$(118–131) | 3': 16z66-pcDNA3 |

What is claimed is:

1. A chimera protein comprising a $G_{\alpha 16}$ protein which includes all ortholog protein sequences and having substituted at least one of the group of its carboxyl-terminal β6-sheet or α5 helix by that of Gα.

2. A chimera protein according to claim 1, wherein said Gα has its 25 carboxyl-terminal residues substituted by the 25 carboxyl-terminal residues of $G\alpha_z$.

3. A chimera protein according to claim 2, having the amino acid sequence of SEQ ID NO:1.

4. A chimera protein according to claim 1, wherein said Gα has its α5 helix replaced by that of $G\alpha_z$.

5. A chimera protein according to claim 1, wherein said Gα has its 44 carboxyl-terminal residues substituted by the 44 carboxyl-terminal residues of $G\alpha_z$.

6. A chimera protein according to claim 5, having the amino acid sequence of SEQ ID NO:2.

7. A chimera protein according to claim 1, wherein said Gα has its β6-sheet and α5 helix replaced by those of $G\alpha_z$.

8. A chimera protein according to claim 1 wherein the carboxyl-terminal β-sheet and α5-helix are substituted by $G\alpha_s$.

9. A non-constitutively active chimera protein comprising a Gα protein other than $G\alpha_s$ having substituted at least one of the group of its carboxyl-terminal β-sheet or α5 helix by that of $G\alpha_s$.

10. A chimera protein according to claim 9, the Gα protein other than $G\alpha_s$ comprising $G\alpha_{16}$.

11. A chimera protein according to claim 10, comprising $G\alpha_{16}$ having its 25 carboxyl-terminal residues substituted by the 25 carboxyl-terminal residues of $G\alpha_s$.

12. A chimera protein according to claim 11, having the amino acid sequence of SEQ ID NO:3.

13. A chimera protein according to claim 10, comprising $G\alpha_{16}$ having its α5 helix replaced by that of $G\alpha_s$.

14. A chimera protein according to claim 10, comprising $G\alpha_{16}$ having its 44 carboxyl-terminal residues substituted by the 44 carboxyl-terminal residues of $G\alpha_s$.

15. A chimera protein according to claim 14, having the amino acid sequence of SEQ ID NO:4.

16. A chimera protein according to claim 10, comprising $G\alpha_{16}$ having its β6-sheet and α5 helix replaced by those of $G\alpha_s$.

17. A chimera protein according to any one of claims 4, 7, 12, and 15 possessing at least one amino acid substitution selected from the group of those at positions 350, 357 and 364 that conserve the structural integrity of the α5 helix, the chimera having the amino acid sequence of SEQ ID NO: 5.

* * * * *

UNITED STATES PATENT AND TRADEMARK OFFICE
CERTIFICATE OF CORRECTION

PATENT NO.    : 6,462,178 B1
DATED         : October 8, 2002
INVENTOR(S)   : Yung Hou Wong It is certified that error appears in the above-identified patent and that said Letters Patent is hereby corrected as shown below:

<u>Title page,</u>
Item [73], correct Assignee to read:
      -- Yung Hou Wong --

Signed and Sealed this

First Day of July, 2003

JAMES E. ROGAN
*Director of the United States Patent and Trademark Office*